US012066426B1

(12) United States Patent
Lapotko et al.

(10) Patent No.: US 12,066,426 B1
(45) Date of Patent: Aug. 20, 2024

(54) PULSED MICRO-CHIP LASER FOR MALARIA DETECTION

(71) Applicant: Masimo Corporation, Irvine, CA (US)

(72) Inventors: Dmitri O. Lapotko, Dana Point, CA (US); Aidas Aleknavicius, Irvine, CA (US)

(73) Assignee: Masimo Corporation, Irvine, CA (US)

( * ) Notice: Subject to any disclaimer, the term of this patent is extended or adjusted under 35 U.S.C. 154(b) by 0 days.

(21) Appl. No.: 18/483,083

(22) Filed: Oct. 9, 2023

Related U.S. Application Data

(63) Continuation of application No. 17/662,559, filed on May 9, 2022, now abandoned, which is a continuation of application No. 16/742,247, filed on Jan. 14, 2020, now abandoned.

(60) Provisional application No. 62/793,247, filed on Jan. 16, 2019.

(51) Int. Cl.
*H01S 3/06* (2006.01)
*G01N 33/49* (2006.01)
*H01S 3/113* (2006.01)

(52) U.S. Cl.
CPC ........... *G01N 33/49* (2013.01); *H01S 3/0627* (2013.01); *H01S 3/113* (2013.01); *G01N 2800/26* (2013.01)

(58) Field of Classification Search
CPC .. G01N 33/49; G01N 2800/26; H01S 3/0627; H01S 3/113
See application file for complete search history.

(56) References Cited

U.S. PATENT DOCUMENTS

| | | | |
|---|---|---|---|
| 4,174,504 A | * | 11/1979 | Chenausky ........... H01S 3/1103 372/99 |
| 4,960,128 A | | 10/1990 | Gordon et al. |
| 4,964,408 A | | 10/1990 | Hink et al. |
| 5,319,355 A | | 6/1994 | Russek |
| 5,337,744 A | | 8/1994 | Branigan |

(Continued)

FOREIGN PATENT DOCUMENTS

| | | |
|---|---|---|
| WO | WO 2007/104098 | 9/2007 |
| WO | WO 2013/109722 | 7/2013 |
| WO | WO 2019/224822 | 11/2019 |

OTHER PUBLICATIONS

Anderson et al., "Optically Guided Controlled Release from Liposomes with Tubable Plasmonic Nanobubbles," Journal of Controlled Release, vol. 144, Issue 2, Jun. 1, 2010, in 22 pages.

(Continued)

*Primary Examiner* — Roy M Punnoose
(74) *Attorney, Agent, or Firm* — Knobbe, Martens, Olson & Bear, LLP

(57) ABSTRACT

A laser suitable for use under field conditions to generate pulsed laser for detecting malaria using transient vapor nanobubbles can include a frequency doubled passively Q-switched microchip laser. The passively Q-switched microchip lasers can include suppression techniques for the unwanted fundamental wavelength in addition to using anti-reflective coatings. The pulsed laser disclosed herein can generate pulses with a high peak power as a result of high energy in conjunction with short pulse duration in the range of hundreds of picoseconds. The high peak power can be enough to generate the photo-thermal transient vapor nanobubbles for malaria detection and/or treatment.

20 Claims, 26 Drawing Sheets

(56) References Cited

U.S. PATENT DOCUMENTS

| | | |
|---|---|---|
| 5,341,805 A | 8/1994 | Stavridi et al. |
| 5,377,676 A | 1/1995 | Vari et al. |
| 5,431,170 A | 7/1995 | Mathews |
| 5,436,499 A | 7/1995 | Namavar et al. |
| 5,456,252 A | 10/1995 | Vari et al. |
| 5,479,934 A | 1/1996 | Imran |
| 5,482,036 A | 1/1996 | Diab et al. |
| 5,494,043 A | 2/1996 | O'Sullivan et al. |
| 5,533,511 A | 7/1996 | Kaspari et al. |
| 5,590,649 A | 1/1997 | Caro et al. |
| 5,602,924 A | 2/1997 | Durand et al. |
| 5,638,816 A | 6/1997 | Kiani-Azarbayjany et al. |
| 5,638,818 A | 6/1997 | Diab et al. |
| 5,645,440 A | 7/1997 | Tobler et al. |
| 5,671,914 A | 9/1997 | Kalkhoran et al. |
| 5,726,440 A | 3/1998 | Kalkhoran et al. |
| D393,830 S | 4/1998 | Tobler et al. |
| 5,743,262 A | 4/1998 | Lepper, Jr. et al. |
| 5,747,806 A | 5/1998 | Khalil et al. |
| 5,750,994 A | 5/1998 | Schlager |
| 5,758,644 A | 6/1998 | Diab et al. |
| 5,760,910 A | 6/1998 | Lepper, Jr. et al. |
| 5,890,929 A | 4/1999 | Mills et al. |
| 5,919,134 A | 7/1999 | Diab |
| 5,987,343 A | 11/1999 | Kinast |
| 5,997,343 A | 12/1999 | Mills et al. |
| 6,002,952 A | 12/1999 | Diab et al. |
| 6,010,937 A | 1/2000 | Karam et al. |
| 6,027,452 A | 2/2000 | Flaherty et al. |
| 6,040,578 A | 3/2000 | Malin et al. |
| 6,066,204 A | 5/2000 | Haven |
| 6,115,673 A | 9/2000 | Malin et al. |
| 6,124,597 A | 9/2000 | Shehada et al. |
| 6,128,521 A | 10/2000 | Marro et al. |
| 6,129,675 A | 10/2000 | Jay |
| 6,144,868 A | 11/2000 | Parker |
| 6,152,754 A | 11/2000 | Gerhardt et al. |
| 6,184,521 B1 | 2/2001 | Coffin, IV et al. |
| 6,232,609 B1 | 5/2001 | Snyder et al. |
| 6,241,683 B1 | 6/2001 | Macklem et al. |
| 6,253,097 B1 | 6/2001 | Aronow et al. |
| 6,255,708 B1 | 7/2001 | Sudharsanan et al. |
| 6,280,381 B1 | 8/2001 | Malin et al. |
| 6,285,896 B1 | 9/2001 | Tobler et al. |
| 6,308,089 B1 | 10/2001 | von der Ruhr et al. |
| 6,317,627 B1 | 11/2001 | Ennen et al. |
| 6,321,100 B1 | 11/2001 | Parker |
| 6,334,065 B1 | 12/2001 | Al-Ali et al. |
| 6,360,114 B1 | 3/2002 | Diab et al. |
| 6,368,283 B1 | 4/2002 | Xu et al. |
| 6,411,373 B1 | 6/2002 | Garside et al. |
| 6,415,167 B1 | 7/2002 | Blank et al. |
| 6,430,437 B1 | 8/2002 | Marro |
| 6,430,525 B1 | 8/2002 | Weber et al. |
| 6,463,311 B1 | 10/2002 | Diab |
| 6,470,199 B1 | 10/2002 | Kopotic et al. |
| 6,487,429 B2 | 11/2002 | Hockersmith et al. |
| 6,505,059 B1 | 1/2003 | Kollias et al. |
| 6,525,386 B1 | 2/2003 | Mills et al. |
| 6,526,300 B1 | 2/2003 | Kiani et al. |
| 6,534,012 B1 | 3/2003 | Hazen et al. |
| 6,542,764 B1 | 4/2003 | Al-Ali et al. |
| 6,580,086 B1 | 6/2003 | Schulz et al. |
| 6,584,336 B1 | 6/2003 | Ali et al. |
| 6,587,196 B1 | 7/2003 | Stippick et al. |
| 6,587,199 B1 | 7/2003 | Luu |
| 6,597,932 B2 | 7/2003 | Tian et al. |
| 6,606,511 B1 | 8/2003 | Ali et al. |
| 6,635,559 B2 | 10/2003 | Greenwald et al. |
| 6,639,668 B1 | 10/2003 | Trepagnier |
| 6,640,116 B2 | 10/2003 | Diab |
| 6,640,117 B2 | 10/2003 | Makarewicz et al. |
| 6,658,276 B2 | 12/2003 | Kiani et al. |
| 6,661,161 B1 | 12/2003 | Lanzo et al. |
| 6,697,656 B1 | 2/2004 | Al-Ali |
| 6,697,658 B2 | 2/2004 | Al-Ali |
| RE38,476 E | 3/2004 | Diab et al. |
| RE38,492 E | 4/2004 | Diab et al. |
| 6,738,652 B2 | 5/2004 | Mattu et al. |
| 6,760,607 B2 | 7/2004 | Al-Ali |
| 6,788,965 B2 | 9/2004 | Ruchti et al. |
| 6,816,241 B2 | 11/2004 | Grubisic |
| 6,822,564 B2 | 11/2004 | Al-Ali |
| 6,850,787 B2 | 2/2005 | Weber et al. |
| 6,850,788 B2 | 2/2005 | Al-Ali |
| 6,876,931 B2 | 4/2005 | Lorenz et al. |
| 6,920,345 B2 | 7/2005 | Al-Ali et al. |
| 6,934,570 B2 | 8/2005 | Kiani et al. |
| 6,943,348 B1 | 9/2005 | Coffin IV |
| 6,956,649 B2 | 10/2005 | Acosta et al. |
| 6,961,598 B2 | 11/2005 | Diab |
| 6,970,792 B1 | 11/2005 | Diab |
| 6,985,764 B2 | 1/2006 | Mason et al. |
| 6,990,364 B2 | 1/2006 | Ruchti et al. |
| 6,998,247 B2 | 2/2006 | Monfre et al. |
| 7,003,338 B2 | 2/2006 | Weber et al. |
| 7,015,451 B2 | 3/2006 | Dalke et al. |
| 7,027,849 B2 | 4/2006 | Al-Ali |
| D526,719 S | 8/2006 | Richie, Jr. et al. |
| 7,096,052 B2 | 8/2006 | Mason et al. |
| 7,096,054 B2 | 8/2006 | Abdul-Hafiz et al. |
| D529,616 S | 10/2006 | Deros et al. |
| 7,133,710 B2 | 11/2006 | Acosta et al. |
| 7,142,901 B2 | 11/2006 | Kiani et al. |
| 7,225,006 B2 | 5/2007 | Al-Ali et al. |
| RE39,672 E | 6/2007 | Shehada et al. |
| 7,230,708 B2 | 6/2007 | Lapotko et al. |
| 7,254,429 B2 | 8/2007 | Schurman et al. |
| 7,254,431 B2 | 8/2007 | Al-Ali et al. |
| 7,254,434 B2 | 8/2007 | Schulz et al. |
| 7,274,955 B2 | 9/2007 | Kiani et al. |
| D554,263 S | 10/2007 | Al-Ali et al. |
| 7,280,858 B2 | 10/2007 | Al-Ali et al. |
| 7,289,835 B2 | 10/2007 | Mansfield et al. |
| 7,292,883 B2 | 11/2007 | De Felice et al. |
| 7,341,559 B2 | 3/2008 | Schulz et al. |
| 7,343,186 B2 | 3/2008 | Lamego et al. |
| D566,282 S | 4/2008 | Al-Ali et al. |
| 7,356,365 B2 | 4/2008 | Schurman |
| 7,371,981 B2 | 5/2008 | Abdul-Hafiz |
| 7,373,193 B2 | 5/2008 | Al-Ali et al. |
| 7,377,794 B2 | 5/2008 | Al-Ali et al. |
| 7,395,158 B2 | 7/2008 | Monfre et al. |
| 7,415,297 B2 | 8/2008 | Al-Ali et al. |
| 7,438,683 B2 | 10/2008 | Al-Ali et al. |
| 7,483,729 B2 | 1/2009 | Al-Ali et al. |
| D587,657 S | 3/2009 | Al-Ali et al. |
| 7,500,950 B2 | 3/2009 | Al-Ali et al. |
| 7,509,494 B2 | 3/2009 | Al-Ali |
| 7,510,849 B2 | 3/2009 | Schurman et al. |
| 7,514,725 B2 | 4/2009 | Wojtczuk et al. |
| 7,519,406 B2 | 4/2009 | Blank et al. |
| D592,507 S | 5/2009 | Wachman et al. |
| 7,530,942 B1 | 5/2009 | Diab |
| 7,593,230 B2 | 9/2009 | Abul-Haj et al. |
| 7,596,398 B2 | 9/2009 | Al-Ali et al. |
| 7,606,608 B2 | 10/2009 | Blank et al. |
| 7,620,674 B2 | 11/2009 | Ruchti et al. |
| D606,659 S | 12/2009 | Kiani et al. |
| 7,629,039 B2 | 12/2009 | Eckerbom et al. |
| 7,640,140 B2 | 12/2009 | Ruchti et al. |
| 7,647,083 B2 | 1/2010 | Al-Ali et al. |
| D609,193 S | 2/2010 | Al-Ali et al. |
| D614,305 S | 4/2010 | Al-Ali et al. |
| 7,697,966 B2 | 4/2010 | Monfre et al. |
| 7,698,105 B2 | 4/2010 | Ruchti et al. |
| RE41,317 E | 5/2010 | Parker |
| RE41,333 E | 5/2010 | Blank et al. |
| 7,729,733 B2 | 6/2010 | Al-Ali et al. |
| 7,761,127 B2 | 7/2010 | Al-Ali et al. |
| 7,764,982 B2 | 7/2010 | Dalke et al. |
| D621,516 S | 8/2010 | Kiani et al. |
| 7,791,155 B2 | 9/2010 | Diab |
| RE41,912 E | 11/2010 | Parker |

(56) References Cited

U.S. PATENT DOCUMENTS

| | | |
|---|---|---|
| 7,880,626 B2 | 2/2011 | Al-Ali et al. |
| 7,909,772 B2 | 3/2011 | Popov et al. |
| 7,919,713 B2 | 4/2011 | Al-Ali et al. |
| 7,937,128 B2 | 5/2011 | Al-Ali |
| 7,937,129 B2 | 5/2011 | Mason et al. |
| 7,941,199 B2 | 5/2011 | Kiani |
| 7,957,780 B2 | 6/2011 | Lamego et al. |
| 7,962,188 B2 | 6/2011 | Kiani et al. |
| 7,976,472 B2 | 7/2011 | Kiani |
| 7,990,382 B2 | 8/2011 | Kiani |
| 7,999,161 B2 | 8/2011 | Oraevsky et al. |
| 8,008,088 B2 | 8/2011 | Bellott et al. |
| RE42,753 E | 9/2011 | Kiani-Azarbayjany et al. |
| 8,028,701 B2 | 10/2011 | Al-Ali et al. |
| 8,048,040 B2 | 11/2011 | Kiani |
| 8,050,728 B2 | 11/2011 | Al-Ali et al. |
| RE43,169 E | 2/2012 | Parker |
| 8,118,620 B2 | 2/2012 | Al-Ali et al. |
| 8,130,105 B2 | 3/2012 | Al-Ali et al. |
| 8,182,443 B1 | 5/2012 | Kiani |
| 8,190,223 B2 | 5/2012 | Al-Ali et al. |
| 8,203,438 B2 | 6/2012 | Kiani et al. |
| 8,203,704 B2 | 6/2012 | Merritt et al. |
| 8,219,172 B2 | 7/2012 | Schurman et al. |
| 8,224,411 B2 | 7/2012 | Al-Ali et al. |
| 8,229,532 B2 | 7/2012 | Davis |
| 8,233,955 B2 | 7/2012 | Al-Ali et al. |
| 8,255,026 B1 | 8/2012 | Al-Ali |
| 8,265,723 B1 | 9/2012 | McHale et al. |
| 8,274,360 B2 | 9/2012 | Sampath et al. |
| 8,280,473 B2 | 10/2012 | Al-Ali |
| 8,315,683 B2 | 11/2012 | Al-Ali et al. |
| RE43,860 E | 12/2012 | Parker |
| 8,346,330 B2 | 1/2013 | Lamego |
| 8,353,842 B2 | 1/2013 | Al-Ali et al. |
| 8,355,766 B2 | 1/2013 | MacNeish, III et al. |
| 8,374,665 B2 | 2/2013 | Lamego |
| 8,388,353 B2 | 3/2013 | Kiani et al. |
| 8,401,602 B2 | 3/2013 | Kiani |
| 8,414,499 B2 | 4/2013 | Al-Ali et al. |
| 8,418,524 B2 | 4/2013 | Al-Ali |
| 8,428,967 B2 | 4/2013 | Olsen et al. |
| 8,430,817 B1 | 4/2013 | Al-Ali et al. |
| 8,437,825 B2 | 5/2013 | Dalvi et al. |
| 8,455,290 B2 | 6/2013 | Siskavich |
| 8,457,707 B2 | 6/2013 | Kiani |
| 8,471,713 B2 | 6/2013 | Poeze et al. |
| 8,473,020 B2 | 6/2013 | Kiani et al. |
| 8,509,867 B2 | 8/2013 | Workman et al. |
| 8,515,509 B2 | 8/2013 | Bruinsma et al. |
| 8,523,781 B2 | 9/2013 | Al-Ali |
| D692,145 S | 10/2013 | Al-Ali et al. |
| 8,571,617 B2 | 10/2013 | Reichgott et al. |
| 8,571,618 B1 | 10/2013 | Lamego et al. |
| 8,571,619 B2 | 10/2013 | Al-Ali et al. |
| 8,577,431 B2 | 11/2013 | Lamego et al. |
| 8,584,345 B2 | 11/2013 | Al-Ali et al. |
| 8,588,880 B2 | 11/2013 | Abdul-Hafiz et al. |
| 8,630,691 B2 | 1/2014 | Lamego et al. |
| 8,641,631 B2 | 2/2014 | Sierra et al. |
| 8,652,060 B2 | 2/2014 | Al-Ali |
| 8,666,468 B1 | 3/2014 | Al-Ali |
| 8,670,811 B2 | 3/2014 | O'Reilly |
| RE44,823 E | 4/2014 | Parker |
| RE44,875 E | 4/2014 | Kiani et al. |
| 8,688,183 B2 | 4/2014 | Bruinsma et al. |
| 8,690,799 B2 | 4/2014 | Telfort et al. |
| 8,702,627 B2 | 4/2014 | Telfort et al. |
| 8,712,494 B1 | 4/2014 | MacNeish, III et al. |
| 8,715,206 B2 | 5/2014 | Telfort et al. |
| 8,723,677 B1 | 5/2014 | Kiani |
| 8,740,792 B1 | 6/2014 | Kiani et al. |
| 8,755,535 B2 | 6/2014 | Telfort et al. |
| 8,755,872 B1 | 6/2014 | Marinow |
| 8,764,671 B2 | 7/2014 | Kiani |
| 8,768,423 B2 | 7/2014 | Shakespeare et al. |
| 8,771,204 B2 | 7/2014 | Telfort et al. |
| 8,781,544 B2 | 7/2014 | Al-Ali et al. |
| 8,790,268 B2 | 7/2014 | Ai-Ali |
| 8,801,613 B2 | 8/2014 | Al-Ali et al. |
| 8,821,397 B2 | 9/2014 | Al-Ali et al. |
| 8,821,415 B2 | 9/2014 | Al-Ali et al. |
| 8,830,449 B1 | 9/2014 | Lamego et al. |
| 8,840,549 B2 | 9/2014 | Al-Ali et al. |
| 8,852,094 B2 | 10/2014 | Al-Ali et al. |
| 8,852,994 B2 | 10/2014 | Wojtczuk et al. |
| 8,897,847 B2 | 11/2014 | Al-Ali |
| 8,911,377 B2 | 12/2014 | Al-Ali |
| 8,989,831 B2 | 3/2015 | Al-Ali et al. |
| 8,998,809 B2 | 4/2015 | Kiani |
| 9,066,666 B2 | 6/2015 | Kiani |
| 9,066,680 B1 | 6/2015 | Al-Ali et al. |
| 9,095,316 B2 | 8/2015 | Welch et al. |
| 9,106,038 B2 | 8/2015 | Telfort et al. |
| 9,107,625 B2 | 8/2015 | Telfort et al. |
| 9,131,881 B2 | 9/2015 | Diab et al. |
| 9,138,180 B1 | 9/2015 | Coverston et al. |
| 9,153,112 B1 | 10/2015 | Kiani et al. |
| 9,155,497 B1 | 10/2015 | Plumley et al. |
| 9,192,329 B2 | 11/2015 | Al-Ali |
| 9,192,351 B1 | 11/2015 | Telfort et al. |
| 9,195,385 B2 | 11/2015 | Al-Ali et al. |
| 9,211,095 B1 | 12/2015 | Al-Ali |
| 9,218,454 B2 | 12/2015 | Kiani et al. |
| 9,245,668 B1 | 1/2016 | Vo et al. |
| 9,267,572 B2 | 2/2016 | Barker et al. |
| 9,277,880 B2 | 3/2016 | Poeze et al. |
| 9,307,928 B1 | 4/2016 | Al-Ali et al. |
| 9,323,894 B2 | 4/2016 | Kiani |
| D755,392 S | 5/2016 | Hwang et al. |
| 9,326,712 B1 | 5/2016 | Kiani |
| 9,392,945 B2 | 7/2016 | Al-Ali et al. |
| 9,408,542 B1 | 8/2016 | Kinast et al. |
| 9,436,645 B2 | 9/2016 | Al-Ali et al. |
| 9,445,759 B1 | 9/2016 | Lamego et al. |
| 9,474,474 B2 | 10/2016 | Lamego et al. |
| 9,480,435 B2 | 11/2016 | Olsen |
| 9,510,779 B2 | 12/2016 | Poeze et al. |
| 9,517,024 B2 | 12/2016 | Kiani et al. |
| 9,532,722 B2 | 1/2017 | Lamego et al. |
| 9,560,996 B2 | 2/2017 | Kiani |
| 9,579,039 B2 | 2/2017 | Jansen et al. |
| 9,622,692 B2 | 4/2017 | Lamego et al. |
| D788,312 S | 5/2017 | Al-Ali et al. |
| 9,649,054 B2 | 5/2017 | Lamego et al. |
| 9,697,928 B2 | 7/2017 | Al-Ali et al. |
| 9,717,458 B2 | 8/2017 | Lamego et al. |
| 9,724,016 B1 | 8/2017 | Al-Ali et al. |
| 9,724,024 B2 | 8/2017 | Al-Ali |
| 9,724,025 B1 | 8/2017 | Kiani et al. |
| 9,749,232 B2 | 8/2017 | Sampath et al. |
| 9,750,442 B2 | 9/2017 | Olsen |
| 9,750,461 B1 | 9/2017 | Telfort |
| 9,775,545 B2 | 10/2017 | Al-Ali et al. |
| 9,778,079 B1 | 10/2017 | Al-Ali et al. |
| 9,782,077 B2 | 10/2017 | Lamego et al. |
| 9,787,568 B2 | 10/2017 | Lamego et al. |
| 9,808,188 B1 | 11/2017 | Perea et al. |
| 9,839,379 B2 | 12/2017 | Al-Ali et al. |
| 9,839,381 B1 | 12/2017 | Weber et al. |
| 9,847,749 B2 | 12/2017 | Kiani et al. |
| 9,848,800 B1 | 12/2017 | Lee et al. |
| 9,861,298 B2 | 1/2018 | Eckerbom et al. |
| 9,861,305 B1 | 1/2018 | Weber et al. |
| 9,877,650 B2 | 1/2018 | Muhsin et al. |
| 9,891,079 B2 | 2/2018 | Dalvi |
| 9,924,897 B1 | 3/2018 | Abdul-Hafiz |
| 9,936,917 B2 | 4/2018 | Poeze et al. |
| 9,955,937 B2 | 5/2018 | Telfort |
| 9,965,946 B2 | 5/2018 | Al-Ali et al. |
| D820,865 S | 6/2018 | Muhsin et al. |
| 9,986,952 B2 | 6/2018 | Dalvi et al. |
| D822,215 S | 7/2018 | Al-Ali et al. |
| D822,216 S | 7/2018 | Barker et al. |

(56) References Cited

U.S. PATENT DOCUMENTS

| | | |
|---|---|---|
| 10,010,276 B2 | 7/2018 | Al-Ali et al. |
| 10,086,138 B1 | 10/2018 | Novak, Jr. |
| 10,111,591 B2 | 10/2018 | Dyell et al. |
| D833,624 S | 11/2018 | DeJong et al. |
| 10,123,729 B2 | 11/2018 | Dyell et al. |
| D835,282 S | 12/2018 | Barker et al. |
| D835,283 S | 12/2018 | Barker et al. |
| D835,284 S | 12/2018 | Barker et al. |
| D835,285 S | 12/2018 | Barker et al. |
| 10,149,616 B2 | 12/2018 | Al-Ali et al. |
| 10,154,815 B2 | 12/2018 | Al-Ali et al. |
| 10,159,412 B2 | 12/2018 | Lamego et al. |
| 10,188,348 B2 | 1/2019 | Al-Ali et al. |
| RE47,218 E | 2/2019 | Al-Ali |
| RE47,244 E | 2/2019 | Kiani et al. |
| RE47,249 E | 2/2019 | Kiani et al. |
| 10,205,291 B2 | 2/2019 | Scruggs et al. |
| 10,226,187 B2 | 3/2019 | Al-Ali et al. |
| 10,231,657 B2 | 3/2019 | Al-Ali et al. |
| 10,231,670 B2 | 3/2019 | Blank et al. |
| RE47,353 E | 4/2019 | Kiani et al. |
| 10,279,247 B2 | 5/2019 | Kiani |
| 10,292,664 B2 | 5/2019 | Al-Ali |
| 10,299,720 B2 | 5/2019 | Brown et al. |
| 10,327,337 B2 | 6/2019 | Schmidt et al. |
| 10,327,713 B2 | 6/2019 | Barker et al. |
| 10,332,630 B2 | 6/2019 | Al-Ali |
| 10,383,520 B2 | 8/2019 | Wojtczuk et al. |
| 10,383,527 B2 | 8/2019 | Al-Ali |
| 10,388,120 B2 | 8/2019 | Muhsin et al. |
| D864,120 S | 10/2019 | Forrest et al. |
| 10,441,181 B1 | 10/2019 | Telfort et al. |
| 10,441,196 B2 | 10/2019 | Eckerbom et al. |
| 10,448,844 B2 | 10/2019 | Al-Ali et al. |
| 10,448,871 B2 | 10/2019 | Al-Ali et al. |
| 10,456,038 B2 | 10/2019 | Lamego et al. |
| 10,463,340 B2 | 11/2019 | Telfort et al. |
| 10,471,159 B1 | 11/2019 | Lapotko et al. |
| 10,505,311 B2 | 12/2019 | Al-Ali et al. |
| 10,524,738 B2 | 1/2020 | Olsen |
| 10,532,174 B2 | 1/2020 | Al-Ali |
| 10,537,285 B2 | 1/2020 | Shreim et al. |
| 10,542,903 B2 | 1/2020 | Al-Ali et al. |
| 10,555,678 B2 | 2/2020 | Dalvi et al. |
| 10,568,553 B2 | 2/2020 | O'Neil et al. |
| 10,608,817 B2 | 3/2020 | Haider et al. |
| D880,477 S | 4/2020 | Forrest et al. |
| 10,617,302 B2 | 4/2020 | Al-Ali et al. |
| 10,617,335 B2 | 4/2020 | Al-Ali et al. |
| 10,637,181 B2 | 4/2020 | Al-Ali et al. |
| D886,849 S | 6/2020 | Muhsin et al. |
| D887,548 S | 6/2020 | Abdul-Hafiz et al. |
| D887,549 S | 6/2020 | Abdul-Hafiz et al. |
| 10,667,764 B2 | 6/2020 | Ahmed et al. |
| D890,708 S | 7/2020 | Forrest et al. |
| 10,721,785 B2 | 7/2020 | Al-Ali |
| 10,736,518 B2 | 8/2020 | Al-Ali et al. |
| 10,750,984 B2 | 8/2020 | Pauley et al. |
| D897,098 S | 9/2020 | Al-Ali |
| 10,779,098 B2 | 9/2020 | Iswanto et al. |
| 10,827,961 B1 | 11/2020 | Iyengar et al. |
| 10,828,007 B1 | 11/2020 | Telfort et al. |
| 10,832,818 B2 | 11/2020 | Muhsin et al. |
| 10,849,554 B2 | 12/2020 | Shreim et al. |
| 10,856,750 B2 | 12/2020 | Indorf |
| D906,970 S | 1/2021 | Forrest et al. |
| D908,213 S | 1/2021 | Abdul-Hafiz et al. |
| 10,918,281 B2 | 2/2021 | Al-Ali et al. |
| 10,932,705 B2 | 3/2021 | Muhsin et al. |
| 10,932,729 B2 | 3/2021 | Kiani et al. |
| 10,939,878 B2 | 3/2021 | Kiani et al. |
| 10,956,950 B2 | 3/2021 | Al-Ali et al. |
| D916,135 S | 4/2021 | Indorf et al. |
| D917,046 S | 4/2021 | Abdul-Hafiz et al. |
| D917,550 S | 4/2021 | Indorf et al. |
| D917,564 S | 4/2021 | Indorf et al. |
| D917,704 S | 4/2021 | Al-Ali et al. |
| 10,987,066 B2 | 4/2021 | Chandran et al. |
| 10,991,135 B2 | 4/2021 | Al-Ali et al. |
| D919,094 S | 5/2021 | Al-Ali et al. |
| D919,100 S | 5/2021 | Al-Ali et al. |
| 11,006,867 B2 | 5/2021 | Al-Ali |
| D921,202 S | 6/2021 | Al-Ali et al. |
| 11,024,064 B2 | 6/2021 | Muhsin et al. |
| 11,026,604 B2 | 6/2021 | Chen et al. |
| D925,597 S | 7/2021 | Chandran et al. |
| D927,699 S | 8/2021 | Al-Ali et al. |
| 11,076,777 B2 | 8/2021 | Lee et al. |
| 11,114,188 B2 | 9/2021 | Poeze et al. |
| D933,232 S | 10/2021 | Al-Ali et al. |
| D933,233 S | 10/2021 | Al-Ali et al. |
| D933,234 S | 10/2021 | Al-Ali et al. |
| 11,145,408 B2 | 10/2021 | Sampath et al. |
| 11,147,518 B1 | 10/2021 | Al-Ali et al. |
| 11,185,262 B2 | 11/2021 | Al-Ali et al. |
| 11,191,484 B2 | 12/2021 | Kiani et al. |
| D946,596 S | 3/2022 | Ahmed |
| D946,597 S | 3/2022 | Ahmed |
| D946,598 S | 3/2022 | Ahmed |
| D946,617 S | 3/2022 | Ahmed |
| 11,272,839 B2 | 3/2022 | Al-Ali et al. |
| 11,289,199 B2 | 3/2022 | Al-Ali |
| RE49,034 E | 4/2022 | Al-Ali |
| 11,298,021 B2 | 4/2022 | Muhsin et al. |
| D950,580 S | 5/2022 | Ahmed |
| D950,599 S | 5/2022 | Ahmed |
| D950,738 S | 5/2022 | Al-Ali et al. |
| D957,648 S | 7/2022 | Al-Ali |
| 11,382,567 B2 | 7/2022 | O'Brien et al. |
| 11,389,093 B2 | 7/2022 | Triman et al. |
| 11,406,286 B2 | 8/2022 | Al-Ali et al. |
| 11,417,426 B2 | 8/2022 | Muhsin et al. |
| 11,439,329 B2 | 9/2022 | Lamego |
| 11,445,948 B2 | 9/2022 | Scruggs et al. |
| D965,789 S | 10/2022 | Al-Ali et al. |
| D967,433 S | 10/2022 | Al-Ali et al. |
| 11,464,410 B2 | 10/2022 | Muhsin |
| 11,504,058 B1 | 11/2022 | Sharma et al. |
| 11,504,066 B1 | 11/2022 | Dalvi et al. |
| D971,933 S | 12/2022 | Ahmed |
| D973,072 S | 12/2022 | Ahmed |
| D973,685 S | 12/2022 | Ahmed |
| D973,686 S | 12/2022 | Ahmed |
| D974,193 S | 1/2023 | Forrest et al. |
| D979,516 S | 2/2023 | Al-Ali et al. |
| D980,091 S | 3/2023 | Forrest et al. |
| 11,596,363 B2 | 3/2023 | Lamego |
| 11,627,919 B2 | 4/2023 | Kiani et al. |
| 11,637,437 B2 | 4/2023 | Al-Ali et al. |
| D985,498 S | 5/2023 | Al-Ali et al. |
| 11,653,862 B2 | 5/2023 | Dalvi et al. |
| D989,112 S | 6/2023 | Muhsin et al. |
| D989,327 S | 6/2023 | Al-Ali et al. |
| 11,678,829 B2 | 6/2023 | Al-Ali et al. |
| 11,679,579 B2 | 6/2023 | Al-Ali |
| 11,684,296 B2 | 6/2023 | Vo et al. |
| 11,692,934 B2 | 7/2023 | Normand et al. |
| 11,701,043 B2 | 7/2023 | Al-Ali et al. |
| D997,365 S | 8/2023 | Hwang |
| 11,721,105 B2 | 8/2023 | Ranasinghe et al. |
| 11,730,379 B2 | 8/2023 | Ahmed et al. |
| D998,625 S | 9/2023 | Indorf et al. |
| D998,630 S | 9/2023 | Indorf et al. |
| D998,631 S | 9/2023 | Indorf et al. |
| D999,244 S | 9/2023 | Indorf et al. |
| D999,245 S | 9/2023 | Indorf et al. |
| D999,246 S | 9/2023 | Indorf et al. |
| 11,766,198 B2 | 9/2023 | Pauley et al. |
| D1,000,975 S | 10/2023 | Al-Ali et al. |
| 11,803,623 B2 | 10/2023 | Kiani et al. |
| 11,832,940 B2 | 12/2023 | Diab et al. |
| 2001/0034477 A1 | 10/2001 | Mansfield et al. |
| 2001/0039483 A1 | 11/2001 | Brand et al. |
| 2002/0010401 A1 | 1/2002 | Bushmakin et al. |

(56) References Cited

U.S. PATENT DOCUMENTS

| | | |
|---|---|---|
| 2002/0058864 A1 | 5/2002 | Mansfield et al. |
| 2002/0133080 A1 | 9/2002 | Apruzzese et al. |
| 2003/0013975 A1 | 1/2003 | Kiani |
| 2003/0018243 A1 | 1/2003 | Gerhardt et al. |
| 2003/0144582 A1 | 7/2003 | Cohen et al. |
| 2003/0156288 A1 | 8/2003 | Barnum et al. |
| 2003/0212312 A1 | 11/2003 | Coffin, IV et al. |
| 2004/0106163 A1 | 6/2004 | Workman, Jr. et al. |
| 2005/0055276 A1 | 3/2005 | Kiani et al. |
| 2005/0234317 A1 | 10/2005 | Kiani |
| 2006/0073719 A1 | 4/2006 | Kiani |
| 2006/0189871 A1 | 8/2006 | Al-Ali et al. |
| 2006/0241459 A1 | 10/2006 | Tai |
| 2007/0073116 A1 | 3/2007 | Kiani et al. |
| 2007/0180140 A1 | 8/2007 | Welch et al. |
| 2007/0244377 A1 | 10/2007 | Cozad et al. |
| 2008/0064965 A1 | 3/2008 | Jay et al. |
| 2008/0094228 A1 | 4/2008 | Welch et al. |
| 2008/0103375 A1 | 5/2008 | Kiani |
| 2008/0221418 A1 | 9/2008 | Al-Ali et al. |
| 2008/0247425 A1* | 10/2008 | Welford .......... H01S 3/113 372/10 |
| 2009/0000614 A1 | 1/2009 | Carrano |
| 2009/0036759 A1 | 2/2009 | Ault et al. |
| 2009/0093687 A1 | 4/2009 | Telfort et al. |
| 2009/0095926 A1 | 4/2009 | MacNeish, III |
| 2009/0141997 A1 | 6/2009 | Lee et al. |
| 2009/0247984 A1 | 10/2009 | Lamego et al. |
| 2009/0275844 A1 | 11/2009 | Al-Ali |
| 2009/0304033 A1* | 12/2009 | Ogilvy .......... H01S 3/08059 372/99 |
| 2010/0004518 A1 | 1/2010 | Vo et al. |
| 2010/0030040 A1 | 2/2010 | Poeze et al. |
| 2010/0099964 A1 | 4/2010 | O'Reilly et al. |
| 2010/0121163 A1 | 5/2010 | Vestel et al. |
| 2010/0222774 A1 | 9/2010 | Hegg et al. |
| 2010/0234718 A1 | 9/2010 | Sampath et al. |
| 2010/0270257 A1 | 10/2010 | Wachman et al. |
| 2011/0028806 A1 | 2/2011 | Merritt et al. |
| 2011/0028809 A1 | 2/2011 | Goodman |
| 2011/0040197 A1 | 2/2011 | Welch et al. |
| 2011/0082711 A1 | 4/2011 | Poeze et al. |
| 2011/0087081 A1 | 4/2011 | Kiani et al. |
| 2011/0118561 A1 | 5/2011 | Tari et al. |
| 2011/0137297 A1 | 6/2011 | Kiani et al. |
| 2011/0172498 A1 | 7/2011 | Olsen et al. |
| 2011/0172508 A1 | 7/2011 | Chickering, III et al. |
| 2011/0176127 A1 | 7/2011 | Kanda et al. |
| 2012/0046593 A1 | 2/2012 | Oraevsky et al. |
| 2012/0069860 A1* | 3/2012 | Inbar .......... H01S 3/09415 372/6 |
| 2012/0123231 A1 | 5/2012 | O'Reilly |
| 2012/0165629 A1 | 6/2012 | Merritt et al. |
| 2012/0165801 A1* | 6/2012 | Bragagna .......... H01S 3/0941 606/18 |
| 2012/0209084 A1 | 8/2012 | Olsen et al. |
| 2012/0226117 A1 | 9/2012 | Lamego et al. |
| 2012/0283524 A1 | 11/2012 | Kiani et al. |
| 2013/0023775 A1 | 1/2013 | Lamego et al. |
| 2013/0060147 A1 | 3/2013 | Welch et al. |
| 2013/0096405 A1 | 4/2013 | Garfio |
| 2013/0296672 A1 | 11/2013 | O'Neil et al. |
| 2013/0345921 A1 | 12/2013 | Al-Ali et al. |
| 2014/0049190 A1 | 2/2014 | Oh |
| 2014/0120167 A1 | 5/2014 | Lapotko et al. |
| 2014/0163353 A1 | 6/2014 | Razansky et al. |
| 2014/0166076 A1 | 6/2014 | Kiani et al. |
| 2014/0180160 A1 | 6/2014 | Brown et al. |
| 2014/0182385 A1 | 7/2014 | Oh et al. |
| 2014/0187973 A1 | 7/2014 | Brown et al. |
| 2014/0275871 A1 | 9/2014 | Lamego et al. |
| 2014/0275872 A1 | 9/2014 | Merritt et al. |
| 2014/0316217 A1 | 10/2014 | Purdon et al. |
| 2014/0316218 A1 | 10/2014 | Purdon et al. |
| 2014/0323897 A1 | 10/2014 | Brown et al. |
| 2014/0323898 A1 | 10/2014 | Purdon et al. |
| 2015/0005600 A1 | 1/2015 | Blank et al. |
| 2015/0011907 A1 | 1/2015 | Purdon et al. |
| 2015/0072337 A1 | 3/2015 | Lapotko et al. |
| 2015/0073241 A1 | 3/2015 | Lamego |
| 2015/0080754 A1 | 3/2015 | Purdon et al. |
| 2015/0099950 A1 | 4/2015 | Al-Ali et al. |
| 2015/0351841 A1 | 12/2015 | Whiteside et al. |
| 2016/0166185 A1 | 6/2016 | Liepmann et al. |
| 2016/0287141 A1 | 10/2016 | Sidlesky |
| 2016/0341747 A1 | 11/2016 | Ewert |
| 2016/0341945 A1 | 11/2016 | Ou et al. |
| 2017/0016827 A1 | 1/2017 | Gervais et al. |
| 2017/0024748 A1 | 1/2017 | Haider |
| 2017/0251974 A1 | 9/2017 | Shreim et al. |
| 2018/0000351 A1 | 1/2018 | Zharov |
| 2018/0242926 A1 | 8/2018 | Muhsin et al. |
| 2018/0247712 A1 | 8/2018 | Muhsin et al. |
| 2018/0344228 A1 | 12/2018 | Yelin |
| 2019/0320906 A1 | 10/2019 | Olsen |
| 2019/0345478 A1 | 11/2019 | Lapotko et al. |
| 2019/0388069 A1 | 12/2019 | Weber et al. |
| 2020/0060869 A1 | 2/2020 | Telfort et al. |
| 2020/0111552 A1 | 4/2020 | Ahmed |
| 2020/0113520 A1 | 4/2020 | Abdul-Hafiz et al. |
| 2020/0138368 A1 | 5/2020 | Kiani et al. |
| 2020/0163597 A1 | 5/2020 | Dalvi et al. |
| 2020/0253474 A1 | 8/2020 | Muhsin et al. |
| 2020/0253544 A1 | 8/2020 | Belur Nagaraj et al. |
| 2020/0275841 A1 | 9/2020 | Telfort et al. |
| 2020/0288983 A1 | 9/2020 | Telfort et al. |
| 2020/0329983 A1 | 10/2020 | Al-Ali et al. |
| 2020/0329993 A1 | 10/2020 | Al-Ali et al. |
| 2021/0022628 A1 | 1/2021 | Telfort et al. |
| 2021/0104173 A1 | 4/2021 | Pauley et al. |
| 2021/0117525 A1 | 4/2021 | Kiani et al. |
| 2021/0121582 A1 | 4/2021 | Krishnamani et al. |
| 2021/0161465 A1 | 6/2021 | Barker et al. |
| 2021/0236729 A1 | 8/2021 | Kiani et al. |
| 2021/0256835 A1 | 8/2021 | Ranasinghe et al. |
| 2021/0275101 A1 | 9/2021 | Vo et al. |
| 2021/0290072 A1 | 9/2021 | Forrest |
| 2021/0290080 A1 | 9/2021 | Ahmed |
| 2021/0290120 A1 | 9/2021 | Al-Ali |
| 2021/0290177 A1 | 9/2021 | Novak, Jr. |
| 2021/0290184 A1 | 9/2021 | Ahmed |
| 2021/0296008 A1 | 9/2021 | Novak, Jr. |
| 2021/0330228 A1 | 10/2021 | Olsen et al. |
| 2021/0386382 A1 | 12/2021 | Olsen et al. |
| 2021/0402110 A1 | 12/2021 | Pauley et al. |
| 2022/0039707 A1 | 2/2022 | Sharma et al. |
| 2022/0053892 A1 | 2/2022 | Al-Ali et al. |
| 2022/0071562 A1 | 3/2022 | Kiani |
| 2022/0096603 A1 | 3/2022 | Kiani et al. |
| 2022/0151521 A1 | 5/2022 | Krishnamani et al. |
| 2022/0218244 A1 | 7/2022 | Kiani et al. |
| 2022/0287574 A1 | 9/2022 | Telfort et al. |
| 2022/0296161 A1 | 9/2022 | Al-Ali et al. |
| 2022/0361819 A1 | 11/2022 | Al-Ali et al. |
| 2022/0379059 A1 | 12/2022 | Yu et al. |
| 2022/0392610 A1 | 12/2022 | Kiani et al. |
| 2023/0028745 A1 | 1/2023 | Al-Ali |
| 2023/0038389 A1 | 2/2023 | Vo |
| 2023/0045647 A1 | 2/2023 | Vo |
| 2023/0058052 A1 | 2/2023 | Al-Ali |
| 2023/0058342 A1 | 2/2023 | Kiani |
| 2023/0069789 A1 | 3/2023 | Koo et al. |
| 2023/0087671 A1 | 3/2023 | Telfort et al. |
| 2023/0110152 A1 | 4/2023 | Forrest et al. |
| 2023/0111198 A1 | 4/2023 | Yu et al. |
| 2023/0115397 A1 | 4/2023 | Vo et al. |
| 2023/0116371 A1 | 4/2023 | Mills et al. |
| 2023/0135297 A1 | 5/2023 | Kiani et al. |
| 2023/0138098 A1 | 5/2023 | Telfort et al. |
| 2023/0145155 A1 | 5/2023 | Krishnamani et al. |
| 2023/0147750 A1 | 5/2023 | Barker et al. |
| 2023/0210417 A1 | 7/2023 | Al-Ali et al. |
| 2023/0222805 A1 | 7/2023 | Muhsin et al. |
| 2023/0222887 A1 | 7/2023 | Muhsin et al. |

(56) References Cited

U.S. PATENT DOCUMENTS

| | | |
|---|---|---|
| 2023/0226331 A1 | 7/2023 | Kiani et al. |
| 2023/0284916 A1 | 9/2023 | Telfort |
| 2023/0284943 A1 | 9/2023 | Scruggs et al. |
| 2023/0301562 A1 | 9/2023 | Scruggs et al. |
| 2023/0346993 A1 | 11/2023 | Kiani et al. |
| 2023/0368221 A1 | 11/2023 | Haider |
| 2023/0371893 A1 | 11/2023 | Al-Ali et al. |
| 2023/0389837 A1 | 12/2023 | Krishnamani et al. |

OTHER PUBLICATIONS

Brusnichkin et al., "Determination of Various Hemoglobin Species with Thermal-Lens Spectrometry," Moscow University Chemistry Bulletin, vol. 64, Issue 1, Feb. 2009, pp. 45-54.

Conjusteau et al., "Metallic Nanoparticles as Optoacoustic Contrast Agents for Medical Imaging," SPIE Proceedings, vol. 6086, Photons Plus Ultrasound: Imaging and Sensing 2006: The Seventh Conference on Biomedical Thermoacoustics, Optoacoustics, and Acousto-optics, Mar. 6, 2006, in 9 pages.

Danysh et al., "The MUC1 Ectodomain: A Novel and Efficient Target for Gold Nanoparticle Clustering and Vapor Nanobubble Generation," Theranostics, 2, No. 8, Ivyspring International Publisher, 2012, pp. 777-787.

Lapotko et al., "Clusterization of Nanoparticles During their Interaction with Living Cells," Nanomedicine, vol. 2, No. 2, Apr. 2007, pp. 241-253.

Lapotko et al., "Elimination of Leukemic Cells from Human Transplants by Laser Nano-Thermolysis," SPIE Proceedings, vol. 6086, Photons Plus Ultrasound: Imaging and Sensing 2006: The Seventh Conference on Biomedical Thermoacoustics, Optoacoustics, and Acousto-optics, Mar. 6, 2006, in 8 pages.

Lapotko et al., "Lantcet: Novel Laser Nanotechnology for Graft Purging," Biology of Blood and Marrow Transplantation, Feb. 2006, in 2 pages.

Lapotko et al., "Laser Activated Nanothermolysis of Leukemia Cells Monitored by Photothermal Microscopy," SPIE Proceedings, vol. 5697, Photons Plus Ultrasound: Imaging and Sensing 2006: The Seventh Conference on Biomedical Thermoacoustics, Optoacoustics, and Acousto-optics, May 5, 2005, pp. 82-89.

Lapotko et al., "Laser Heating Diagnoses and Treats Cancerous Cells," SPIE Newsroom, The International Society for Optical Engineering, 2006, in 3 pages.

Lapotko et al., "Method of Laser Activated Nano-Thermolysis for Elimination of Tumor Cells," Cancer Letters, vol. 239, Issue 1, Jul. 28, 2006, pp. 36-45.

Lapotko, "Monitoring of Apoptosis in Intact Single Cells with Photothermal Microscope," Journal of the International Society for Advancement of Cytometry, vol. 58A, Issue 2, Apr. 2004, pp. 111-119.

Lapotko, "Optical Excitation and Detection of Vapor Bubbles Around Plasmonic Nanoparticles," Optics Express, vol. 17, Issue 4, Feb. 16, 2009, pp. 2538-2556.

Lapotko et al., "Photothermal and Photoacoustic Processes in Laser Activated Nano-Thermolysis of Cells," SPIE Proceedings, vol. 6437, Photons Plus Ultrasound: Imaging and Sensing 2007: The Eighth Conference on Biomedical Thermoacoustics, Optoacoustics, and Acousto-optics, Mar. 2007, in 13 pages.

Lapotko et al., "Photothermal Detection of Laser-Induced Damage in Single Intact Cells," Lasers in Surgery and Medicine, vol. 33, Issue 5, Dec. 2003, pp. 320-329.

Lapotko et al., "Photothermal Image Cytometry of Human Neutrophils," Journal of the International Society for Advancement of Cytometry, vol. 24, Issue 3, Jul. 1, 1996, pp. 198-203.

Lapotko et al., "Photothermal Response of Live Cells Depends Upon Cell Metabolic State," SPIE Proceedings, vol. 4618, Biomedical Optoacoustics III, Jun. 10, 2002, in 8 pages.

Lapotko et al., "Photothermal Time-Resolved Imaging of Living Cells," Lasers in Surgery and Medicine, vol. 31, Issue 1, Jul. 2002, pp. 53-63.

Lapotko et al., "Photothermolysis by Laser-Induced Microbubbles Generated Around Gold Nanorod Clusters Selectively Formed in Leukemia Cells," SPIE Proceedings, vol. 6856, Photons Plus Ultrasound: Imaging and Sensing 2008: The Ninth Conference on Biomedical Thermoacoustics, Optoacoustics, and Acousto-optics, Feb. 28, 2008, in 10 pages.

Lapotko, "Plasmonic Nanobubbles as Tunable Cellular Probes for Cancer Theranostics," Cancers, vol. 3, No. 1, 2011 pp. 802-840.

Lapotko, "Plasmonic Nanoparticle-Generated Photothermal Bubbles and their Biomedical Applications," Nanomedicine, vol. 4, No. 7, Oct. 2009, pp. 813-845.

Lapotko, "Nanophotonics and Theranostics: Will Light do the Magic?" Theranostics 2013, vol. 3, Issue 3, pp. 138-140.

Lapotko et al., "Nonstationary Heating and Phase Transitions in a Live Cell in Absorption of Laser Radiation," Heat Transfer Research, vol. 38, Issue 8, Jan. 2007, pp. 695-708.

Lapotko et al., "Selective Laser Nano-Thermolysis of Human Leukemia Cells with Microbubbles Generated Around Clusters of Gold Nanoparticles," Lasers in Surgery and Medicine, vol. 38, Issue 6, Jul. 2006, pp. 631-642.

Lapotko, "Therapy with Gold Nanoparticles and Lasers: What Really Kills the Cells?" Nanomedicine, vol. 4, No. 3, Apr. 2009, pp. 253-256.

Lukianova-Hleb et al., "All-in-one Processing of Heterogeneous Human Cell Grafts for Gene and Cell Therapy," Molecular Therapy—Methods & Clinical Development , vol. 3, Article 16012, 2016, in 8 pages.

Lukianova-Hleb et al., "Cell-Specific Multifunctional Processing of Heterogeneous Cell Systems in aSingle Laser Pulse Treatment," ACS Nano, vol. 6, Issue 12, Dec. 21, 2012, p. 10973-10981.

Lukianova-Hleb et al., "Cell-Specific Transmembrane Injection of Molecular Cargo with Gold Nanoparticle-Generated Transient Plasmonic Nanobubbles," Biomaterials, vol. 33, Issue 21, Jul. 2012, pp. 5441-5450.

Lukianova-Hleb et al., "Experimental Techniques for Imaging and Measuring Transient Vapor Nanobubbles," Applied Physics Letters, vol. 101, Dec. 2012, pp. 264102-1-264102-5.

Lukianova-Hleb et al., "Generation and Detection of Plasmonic Nanobubbles in Zebrafish," Nanotechnology, vol. 21, No. 22, Jun. 4, 2010, in 22 pages.

Lukianova-Hleb et al., "Hemozoin-Generated Vapor Nanobubbles for Transdermal Reagent andNeedle-Free Detection of Malaria," Proceedings of the National Academy of Sciences of the United States of America, vol. 111, No. 3, Jan. 21, 2014, pp. 900-905.

Lukianova-Hleb et al., "Improved Cellular Specificity of Plasmonic Nanobubbles versus Nanoparticles in Heterogeneous Cell Systems," PLoS One, vol. 7, Issue 4, Apr. 2012, in 10 pages.

Lukianova-Hleb et al., "Intraoperative Diagnostics and Elimination of Residual Micro-Tumours with Plasmonic Nanobubbles," Nature Nanotechnology, 2015, in 31 pages.

Lukianova-Hleb et al., "Influence of Transient Environmental Photothermal Effects on Optical Scattering by Gold Nanoparticles," Nano Letters, vol. 9, Issue 5, May 2009, pp. 2160-2166.

Lukianova-Hleb et al., "Laser Pulse Duration is Critical for the Generation of Plasmonic Nanobubbles," Langmuir, vol. 30, Issue 25, 2014, pp. 7425-7434.

Lukianova-Hleb et al., "Malaria Theranostics Using Hemozoin-Generated Vapor Nanobubbles," Theranostics, vol. 4, Issue 7, 2014, pp. 761-769.

Lukianova-Hleb et al., "Multifunctional Cell Processing with Plasmonic Nanobubbles," International Journal of Medical, Health, Biomedical, Bioengineering and Pharmaceutical Engineering, vol. 7, No. 11, 2013, pp. 677-681.

Lukianova-Hleb et al., "Plasmonic Nanobubbles Enhance Efficacy and Selectivity of Chemotherapy Against Drug-Resistant Cancer Cells," Advanced Materials, vol. 24, Issue 28, Jul. 24, 2012, pp. 3831-3837.

Lukianova-Hleb et al., "Plasmonic Nanobubbles for Intracellular Targeting and Gene Therapy," NTSI-Nanotech 2011, vol. 3, pp. 291-294.

Lukianova-Hleb et al., "Plasmonic Nanobubbles as Transient Vapor Nanobubbles Generated Around Plasmonic Nanoparticles," ACS Nano, vol. 4, Issue 4, Apr. 27, 2010, pp. 2109-2123.

(56) References Cited

OTHER PUBLICATIONS

Lukianova-Hleb et al., "Plasmonic Nanobubble-Enhanced Endosomal Escape Processes for Selective and Guided Intracellular Delivery of Chemotherapy to Drug-Resistant Cancer Cells," Biomaterials, vol. 33, Issue 6, Feb. 2012, pp. 1821-1826.

Lukianova-Hleb et al., "Plasmonic Nanobubbles Rapidly Detect and Destroy Drug-Resistant Tumors," Theranostics, vol. 2, No. 10, 2012, pp. 976-787.

Lukianova-Hleb et al., "Plasmonic Nanobubbles for Cell Theranostic," Proceedings of SPIE, 2012, vol. 8234, pp. 82341F-1-82341F-10.

Lukianova-Hleb et al., "Plasmonic Nanobubbles as Tunable Theranostic Agents," NSTI-Nanotech 2011, vol. 3, pp. 367-370.

Lukianova-Hleb et al., "Plasmonic Nanobubbles: Tunable and Transient Probes for Cancer Diagnosis, Therapy and Theranostics," NSTI-Nanotech 2010, vol. 3, 2010 in 5 pages.

Lukianova-Hleb et al., "Rainbow Plasmonic Nanobubbles: Synergistic Activation of Gold Nanoparticle Clusters," Journal of Nanomedicine & Nanotechnology, vol. 2, Issue 104, Jan. 1, 2011, in 21 pages.

Lukianova-Hleb et al., "Safety and Efficacy of Quadrapeutics Versus Chemoradiation in Head and Neck Carcinoma Xenograft Model," American Journal of Cancer Research, vol. 5, Issue 12, 2015, pp. 3534-3547.

Lukianova-Hleb et al., "Selective Gene Transfection of Individual Cells In Vitro with Plasmonic Nanobubbles," Journal of Controlled Release, vol. 152, Issue 2, Jun. 10, 2011, pp. 286-293.

Lukianova-Hleb et al., "Selective and Self-Guided Micro-Ablation of Tissue with Plasmonic Nanobubbles," Journal of Surgical Research, vol. 166, Issue 1, Mar. 2011, pp. e3-e13.

Lukianova-Hleb et al., "Short Laser Pulse-Induced Irreversible Photothermal Effects in Red Blood Cells," Lasers in Surgery and Medicine, vol. 43, Issue 3, Mar. 2011, pp. 249-260.

Lukianova-Hleb et al., "Transdermal Diagnosis of Malaria Using Vapor Nanobubbles," Emerging Infectious Diseases, vol. 21, No. 7, Jul. 2015, pp. 1122-1127.

Lukianova-Hleb et al., "Transient Enhancement and Spectral Narrowing of the Photothermal Effect of Plasmonic Nanoparticles Under Pulsed Excitation," Advanced Materials, vol. 25, Issue 5, Feb. 6, 2013, pp. 772-776.

Lukianova-Hleb et al., "Transient Photothermal Spectra of Plasmonic Nanobubbles," Langmuir, vol. 28, Issue 10, Feb. 2012, pp. 4858-4866.

Lukianova-Hleb et al., "Tunable Plasmonic Nanobubbles for Cell Theranostics," Nanotechnology, vol. 21, No. 8, Feb. 26, 2010, in 19 pages.

Lukianova-Hleb et al., "Tunable Plasmonic Nanoprobes for Theranostics of Prostate Cancer," Theranostics, vol. 1, 2011, pp. 3-17.

Potkin et al., "The Influence of Heterocyclic Compound-Pamam Dendrimer Complexes on EvokedElectrical Responses in Slices of Hypoxic Brain Tissue," Cellular & Molecular Biology Letters, vol. 19, 2014, pp. 243-248.

Vasiliev et al., "Bubble Generation in Micro-Volumes of 'nonofluids'," International Journal of Heat and Mass Transfer, vol. 52, Issues 5-6, Feb. 2009, pp. 1534-1539.

\* cited by examiner

PULSED MICRO-CHIP LASER FOR MALARIA DETECTION

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57. This application is a continuation of U.S. patent application Ser. No. 17/662,559, filed May 9, 2022, which is a continuation of U.S. patent application Ser. No. 16/742,247, filed Jan. 14, 2020, which claims the priority benefit of U.S. Provisional Application No. 62/793,247, filed Jan. 16, 2019, the entirety of which is incorporated herein by reference.

FIELD

The present application relates generally to the field of detection of malaria parasites in a patient's body, in particular, with the use of laser-induced transient vapor nanobubbles.

BACKGROUND

Malaria is a widespread and infectious disease that can cause serious illness and/or death in humans. A patient can be infected when a malaria parasite infects cells of the patient, also known as a host. The parasite can produce hemozoin (Hz), which are nanocrystals formed when the parasite digests the hemoglobin in the host's red blood cells. Malaria-infected red blood cells or other body tissue infected by malaria parasites contain Hz nanocrystals.

Current malaria diagnosis techniques include, for example, rapid diagnostic tests (RDTs), microscopy, and polymerase chain reaction (PCR). These diagnosis techniques analyze a patient's blood samples. RDT analyzes the proteins in the blood to look for presence of malaria parasites and is approved by the World Health Organization (WHO). Microscopy uses stain of a thick blood slide, such as with a 200 to 500 white blood cell count, to determine malaria parasite density and gametocyte counts. Microscopy is also WHO-approved for malaria diagnosis. PCR analyzes DNAs in the blood to determine presence of malaria parasites.

Malaria can be treated and/or prevented by administration of antimalarial drugs, such as quinine, chloroquine, atovaquone/proguanil, and others.

SUMMARY

Current malaria diagnosis and treatment generally employ invasive techniques which are costly, time-consuming, and have low accuracy. The diagnosis and treatment of malaria can require separate procedures. Current malaria diagnosis techniques also may not detect the Hz nanocrystals without an active and/or live malaria parasite, and/or tissue-sequestered malaria parasites.

Laser-induced transient vapor nanobubbles can be used to diagnose and/or treat malaria in a noninvasive, efficient, and reproducible manner. The transient vapor nanobubbles can be generated around malaria-specific nanoparticles (such as the Hz nanocrystals, with or without an active malaria parasite, and/or other malaria-specific nanoparticles that can be introduced into the host red blood cells) when laser pulses are applied to those nanoparticles. The laser pulses can cause rapid heating of the malaria-specific nanoparticles, but not of uninfected red blood cells or other host tissues. Liquid (such as water) around the malaria-specific nanoparticles can rapidly evaporate, leading to the generation of a transient vapor nanobubble. The generation of transient vapor nanobubbles can be detected by optical and/or acoustic detectors.

In order to use transient vapor nanobubbles to detect and/or treat malaria noninvasively, the laser pulses must penetrate a patient's skin and reach the malaria-specific nanoparticles despite attenuation of the laser pulses energy by the patient's body tissue (particularly by the melanin layer in the skin) as the laser pulses travel deeper under the skin. Example malaria sensors based on laser-induced transient vapor nanobubble technology are described in U.S. application Ser. No. 16/213,923, filed Dec. 7, 2018 and titled "APPARATUS FOR DIAGNOSING AND/OR TREATING MALARIA," the entirety of which is incorporated herein by reference and should be considered part of the disclosure.

Malaria is a mosquito-borne infectious disease and known as a cause for poverty. Malaria outbreak tends to happen in tropical regions and/or other places having a rugged environment. As the malaria sensors may need to be used in places having a rugged environment, a reliable, rugged and/or compact pulsed laser can be desirable. A rugged environment can pose challenges such as limited healthcare resources, low levels of sanitation, extreme weather conditions (such as the tropical weather), and/or being in a remote location with low accessibility. For a pulsed laser reaching underneath a patient's skin to generate photo-thermal transient vapor nanobubbles around the malaria-specific nanoparticles for malaria detection and/or treatment, a pulsed laser needs to deliver laser pulses of several hundred picoseconds in duration (such as less than about 300 ps), and several tens of microjoule in energy (such as greater than about 20 µJ at the wavelength range of about 670 nm to about 675 nm). The pulsed laser also needs to operate under field conditions, such as in a rugged environment, to deliver, preferably reliably in repeated use, with the above-described parameters.

The above-described parameters of the laser pulse can be achieved with lasers having an optical parametric amplifier (OPA) and appropriate pulsed laser as a pump source. Lasers that can deliver pulses in a several tens of picoseconds duration can be amplified mode-locked oscillators. The duration also can be stretched up to several hundreds of picoseconds. The above-described parameters of the laser pulse can also be achieved with a single longitudinal mode laser delivering pulses of several nanoseconds, which can be compressed using a stimulated Brillouin scattering (SBS) effect. However, lasers of such approaches can be bulky, expensive, and/or may operate only under laboratory conditions and thus may not be suitable for use under the field conditions.

A pulsed micro-laser ("microchip") can be more compact and less expensive than the lasers described above. Microchip pulsed laser is available for the above-described parameters required, but the currently available microchip lasers use an actively Q-switch component. Active Q-switch components are available as off-the-shelf products (such as Standa-Q1SH671), which are frequency doubled Nd:YVO4 based actively Q-switched lasers lasing at a fundamental wavelength of 1064 nm. Frequency doubling as used in the present disclosure has the plain meaning as understood by an ordinary person skilled in the art, such as a phenomenon wherein an input wave in a nonlinear material generates a wave with twice the optical frequency (and thus half the wavelength) of the input wave. However, microchip lasers with an active Q-switch component can still be complex, expensive, and/or unreliable under the field conditions.

The present disclosure provides embodiments of a pulsed laser that remedies one or more of the problems described and/or other problems. The pulsed laser can generate laser pulses of the above-described parameter under the field conditions, preferably reliably in repeated use. The pulsed laser embodiments described herein can have a frequency doubled passively Q-switched microchip laser with the desired and/or wanted wavelength at about 1340 nm to about 1350 nm. Passively Q-switched microchip lasers can be less expensive, more compact, and/or more robust than the aforementioned lasers. Because of the shorter cavity length due to the more compact size of a frequency doubled passively Q-switched microchip laser, embodiments of the pulsed laser disclosed herein can generate pulses with a higher peak power as a result of higher energy in conjunction with shorter pulse duration in the range of hundreds of picoseconds. The higher peak power in the generated laser pulses can be sufficient to generate the photo-thermal transient vapor nanobubbles around the malaria-specific nanoparticles for malaria detection and/or treatment. The passively Q-switched microchip laser embodiments disclosed herein can include suppression techniques for unwanted wavelengths in addition to using anti-reflective coatings for the unwanted wavelengths.

A passively Q-switched microchip laser configured for generating transient vapor nanobubbles around malaria-specific nanoparticles in a human can comprise a laser cavity bound by a reflector and an optical coupler; a gain element located in the cavity, the gain element having a first axis, a gain element surface that is generally perpendicular to the first axis, and an inclined gain element surface that is at an acute angle to the first axis, the perpendicular gain element surface being adjacent to one of the reflector or the optical coupler; a saturable absorber element in the cavity, the saturable absorber element having a second axis, a saturable absorber element surface that is generally perpendicular to the second axis, and an inclined saturable absorber element surface that is at an acute angle to the second axis, the perpendicular saturable absorber element surface being adjacent to another one of the reflector or the optical coupler, wherein, in response to pumping energy at a predetermined pumping wavelength, the gain element can be configured to produce simulated emission of at least a wanted wavelength and an unwanted wavelength, wherein a simulated emission cross-section of the unwanted wavelength is greater than a simulated emission cross-section of the wanted wavelength, wherein the saturable absorber element can be configured to output a pulsed laser beam substantially of the wanted wavelength, wherein the reflector and the optical coupler cam be anti-reflective of the unwanted wavelength, and the inclined surfaces of the gain element and the saturable absorber element can each be configured to direct light of the unwanted wavelength away from the first and/or second axis to reduce feedback of the unwanted wavelength along the first and/or second axis.

The system can include one or more of the following features: the pulsed laser beam can have a duration less than about 300 picoseconds; the pulsed laser beam can have an energy of at least about 20 microjoule; the pulse laser beam can have a wavelength of between 670 nm to about 675 nm; the inclined surface of the saturable absorber element can be reflective or highly reflective of the pump wavelength so that the saturable absorber element is protected from bleaching by pump radiation; the inclined surfaces of the gain element and the saturable absorber element can be anti-reflective of the wanted wavelength; the inclined surfaces of the gain element and the saturable absorber element can be separated by a gap, wherein at least a portion of light of the unwanted wavelength in the gap can be reflected away from the first and/or second axis to increase losses in the cavity; the pumping energy can be delivered into the cavity from the reflector or along a length of the cavity toward the inclined surface of the saturable absorber element; the pumping energy can be double-passed in the gain element to increase excitation of the gain element; the inclined surface of the saturable absorber element can be reflective or highly reflective of the unwanted wavelength; the first and second axes can be substantially collinear; the first and second axes can be offset from each other; the inclined surfaces of the gain element and the saturable absorber element are generally parallel; the first axis can be at an angle with second axis; the inclined surfaces of the gain element and the saturable absorber element can be generally not parallel; slopes of the inclined surfaces of the gain element and the saturable absorber element can extend away from each other so that light travels through a longer section of the gain element followed by a longer section of the saturable absorber element, or through a shorter section of the gain element followed by a shorter section of the saturable absorber element; the gain element and the saturable absorber element can each comprise a doped part and an undoped part, the doped part comprising a generally uniform cross-section normal to the first axis and/or the second axis; further comprising an exo-cavity element; the exo-cavity element can be located between a pump and the cavity along a length of the cavity, the exo-cavity element configured to isolate feedback of the unwanted wavelength from pump shaping optics; the exo-cavity element can be located on an opposite side of the gain element from a pump, the exo-cavity element configured to reflect back pump radiation into the cavity; the perpendicular surface of the gain element can comprise a two-wavelength coating for the wanted and unwanted wavelengths, the perpendicular surface of the gain element having an unspecified reflectivity for the pump wavelength; the system can comprise an intra-cavity element between the gain element and the saturable absorber element, the intra-cavity element configured to focus pump radiation into the gain element; the reflector can be at or next to the perpendicular gain element surface and the optical coupler can be at or next to the perpendicular saturable absorber element surface; and/or the reflector can be at or next to the perpendicular saturable absorber element surface and the optical coupler can be at or next to the perpendicular gain element surface.

A passively Q-switched microchip laser configured for generating transient vapor nanobubbles around malaria-specific nanoparticles in a human can comprise a laser cavity bound by a reflector and an optical coupler, the laser cavity having an optical axis; a gain element located in the cavity, the gain element having a gain element surface that is generally perpendicular to the optical axis, and an inclined gain element surface that is at an acute angle to the optical axis, the perpendicular gain element surface being adjacent to the reflector; a saturable absorber element in the cavity and adjacent to the gain element, the saturable absorber element having a saturable absorber element surface that is generally perpendicular to the optical axis, and an inclined saturable absorber element surface that is at an acute angle to the optical axis, the perpendicular saturable absorber element surface being adjacent to the optical coupler, wherein the inclined surfaces of the gain element and the saturable absorber element are generally parallel and separated by a predetermined distance; and an exo-cavity element located next to the perpendicular gain element surface and substantially collinear with the optical axis, the exo-cavity element configured to isolate feedback of an unwanted wavelength from pump shaping optics; wherein, in response to pumping energy at a predetermined pumping wavelength, the gain element can be configured to produce simulated emission of at least a wanted wavelength and the unwanted wavelength, wherein a simulated emission cross-section of the unwanted wavelength can be greater than a simulated emission cross-section of the wanted wavelength, wherein the saturable absorber element can be configured to output a pulsed laser beam substantially of the wanted wavelength, wherein the reflector and the optical coupler can be anti-reflective of the unwanted wavelength, and the inclined surfaces of the gain element and the saturable absorber element can each be configured to direct light of the unwanted wavelength away from the optical axis to reduce feedback of the unwanted wavelength along the optical axis and/or to increase losses in the cavity.

A passively Q-switched microchip laser configured for generating transient vapor nanobubbles around malaria-specific nanoparticles in a human can comprise: a laser cavity bound by a reflector and an optical coupler and having a laser cavity axis; a gain element and a saturable absorber element located in the cavity, the gain element and the saturable absorber element each having a first surface adjacent to one of the reflector or the optical coupler, the gain element and the saturable absorber element each having a second surface adjacent to another one of the reflector or the optical coupler, one or both of the second surfaces of the gain element and the saturable absorber element being inclined relative to the laser cavity axis; wherein, in response to pumping energy at a predetermined pumping wavelength, the gain element can be configured to produce simulated emission of at least a first wavelength and a second wavelength, wherein a simulated emission cross-section of the second wavelength can be greater than a simulated emission cross-section of the first wavelength, wherein the saturable absorber element can be configured to output a pulsed laser beam substantially of the first wavelength, and wherein the reflector and the optical coupler are configured to suppress the second wavelength.

The laser can include one or more of the following features: the reflector and the optical coupler can be anti-reflective of the second wavelength; the second gain element and saturable absorber element surfaces can be each configured to direct light of the second wavelength away from the laser cavity axis to reduce feedback of the second wavelength along the laser cavity second axis; the pulsed laser beam can have a duration less than about 300 picoseconds; the pulsed laser beam can have an energy of at least about 20 microjoule; the pulse laser beam can have a wavelength of between 670 nm to about 675 nm; the second surface of the saturable absorber element can be reflective or highly reflective of the pump wavelength so that the saturable absorber element is protected from bleaching by pump radiation; the second surfaces of the gain element and saturable absorber element can be anti-reflective of the first wavelength; the second surfaces of the gain element and saturable absorber element can be separated by a gap, wherein at least a portion of light of the second wavelength in the gap can be reflected away from the laser cavity axis to increase losses in the cavity; the pumping energy can be delivered into the laser cavity from the reflector or along a length of the cavity toward the second surface of the saturable absorber element; the pumping energy can be double-passed in the gain element to increase excitation of the gain element; the second surface of the saturable absorber element can be reflective or highly reflective of the second wavelength; the gain element can be at an angle with the saturable absorber element; or the second surfaces of the gain element and saturable absorber element can be at an angle with each other; slopes of the second surfaces of the gain element and saturable absorber element can extend away from each other so that light travels through a longer section of the gain element followed by a longer section of the saturable absorber element, or through a shorter section of the gain element followed by a shorter section of the saturable absorber element; the reflector can be at or next to the first gain element surface and the optical coupler can be at or next to the first saturable absorber element surface; or the reflector can be at or next to the first saturable absorber element surface and the optical coupler can be at or next to the first gain element surface.

A laser light generator device configured for generating transient vapor nanobubbles around malaria-specific nanoparticles in a human can comprise any of the example passively Q-switched microchip lasers described above; a pump coupled to the passively Q-switched microchip laser via a pump fiber; and an output fiber coupling the passively Q-switched microchip laser and one or more malaria detection sensors.

The device can include one or more of the following features: the device can comprise pump shaping optics between the pump fiber and the passively Q-switched microchip laser; the device can comprise second harmonic generation and filtering elements coupling the passively Q-switched microchip laser to the output fiber; and/or the device can be configured to sequentially switch the outputted pulsed laser beam among a plurality of optical fibers in the one or more malaria detection sensors.

BRIEF DESCRIPTION OF THE DRAWINGS

Various embodiments are depicted in the accompanying drawings for illustrative purposes and may not be drawn to scale, and should in no way be interpreted as limiting the scope of the embodiments. In addition, various features of different disclosed embodiments can be combined to form additional embodiments, which are part of this disclosure. In the drawings, similar elements have reference numerals with the same last two digits.

FIG. 1A illustrates schematically basic components of a laser.

FIG. 1B illustrates schematically energy levels of particles relating to generation of a laser beam.

FIG. 2A illustrates schematically an example passively Q-switched micro-chip laser.

FIG. 2B illustrates schematically example energy levels of a passively Q-switched micro-chip laser.

FIG. 3A illustrates schematically an example passively Q-switched micro-chip laser.

FIG. 3B illustrates schematically an example passively Q-switched micro-chip laser.

FIG. 4 illustrates schematically an example passively Q-switched micro-chip laser.

FIG. 5A illustrates schematically an example passively Q-switched micro-chip laser.

FIG. 5B illustrates schematically an example passively Q-switched micro-chip laser.

FIG. 6A illustrates schematically an example passively Q-switched micro-chip laser.

DETAILED DESCRIPTION

Although certain embodiments and examples are described below, this disclosure extends beyond the specifically disclosed embodiments and/or uses and obvious modifications and equivalents thereof. Thus, it is intended that the scope of this disclosure should not be limited by any particular embodiments described below.

Overview of Laser Technology

Figure 1A:
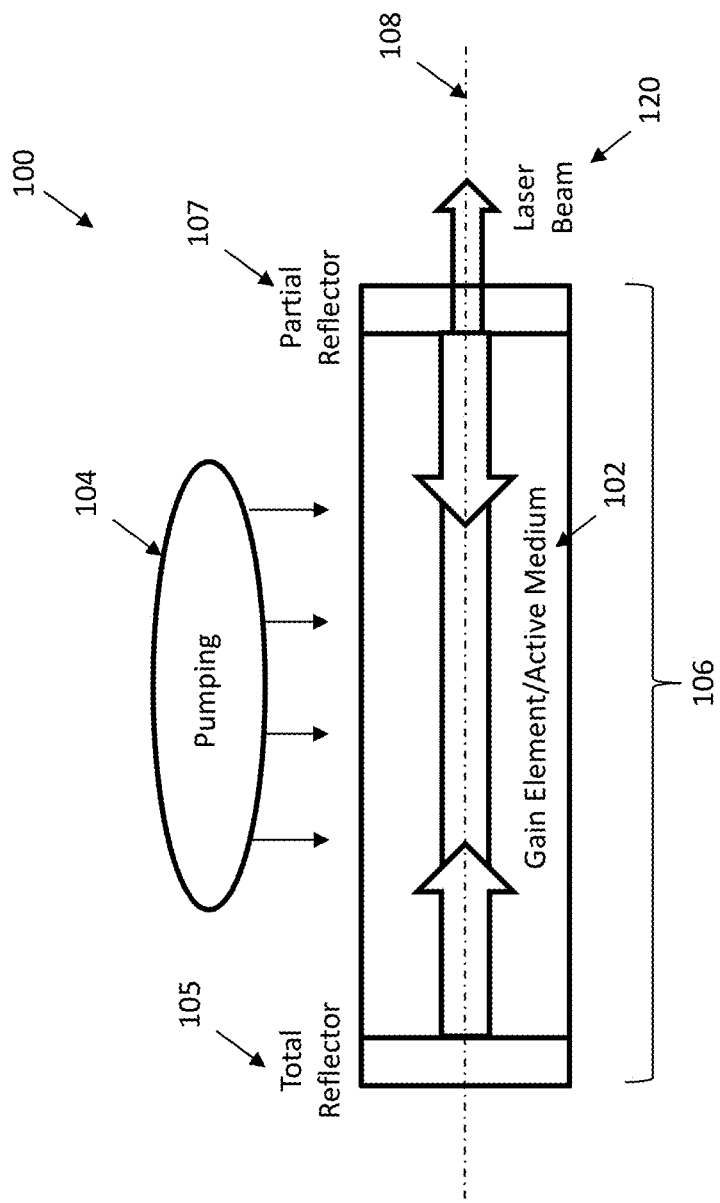

FIG. 1A illustrates schematically an example laser 100, which includes a gain element (also known as gain medium or active medium) 102 with energy levels configured to support laser action, and an energy pump 104 in order to establish a population inversion. The gain element 102 can be located in an optical cavity or optical resonator 106, which can maintain the gain of the laser 100.

Figure 1B:
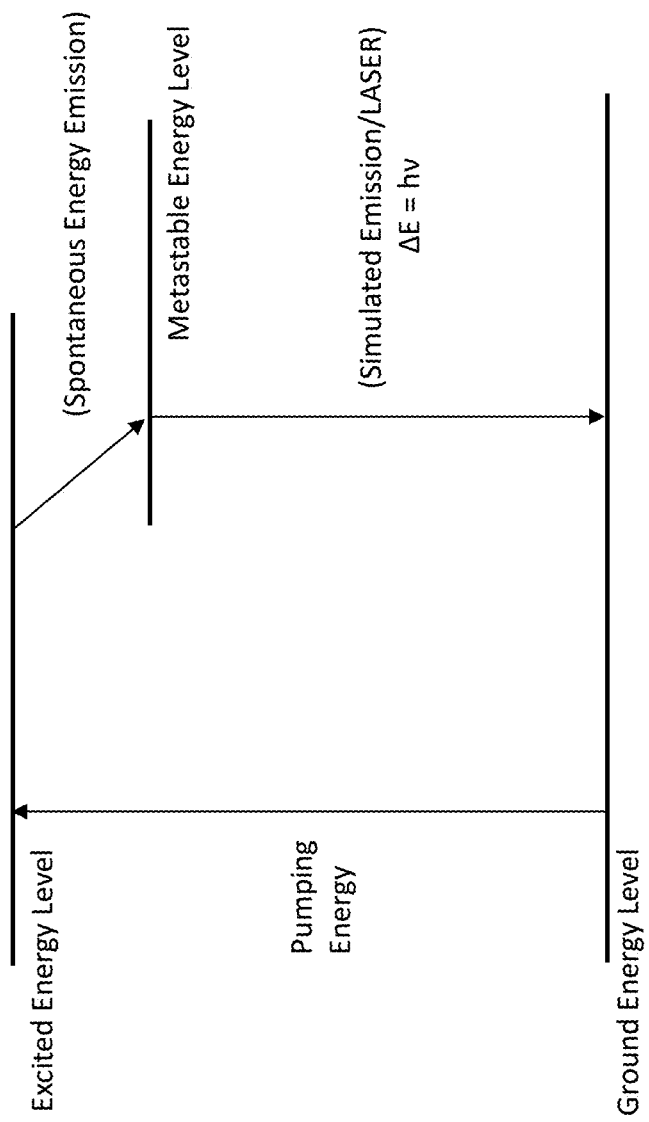

The gain element 102 can produce gain and subsequent generation of laser light. The gain element 102 can be a crystal, solid, liquid, semiconductor, or gas medium and can be pumped by the energy pump 104 to a higher energy state. The gain element material has a metastable state that supports stimulated emission. Laser light generation can be based on 3- or 4-level energy level systems, depending on the type of gain element used. FIG. 1B illustrates a 3 level energy level system. As shown in FIG. 1B, the gain element 102 can be pumped from a ground level to an excited level, which decays rapidly to a metastate level through spontaneous emission, and further decays from the metastate level to the ground level through stimulated emission (also known as lasing). The light of stimulated emission is coherent and can be focused to a spot. The laser light or laser beam 120 generated by the laser 100 can have an energy that is the difference between the metastate level and the ground level, $\Delta E$. The wavelength of the laser beam emitted through simulated emission can be calculated based on the equation $\Delta E = h\nu$, where h is the Planck's constant and $\nu$ is the frequency of the laser beam.

The pump 104 can provide energy to excite elements such as the atoms, electrons, ions or molecules in the gain element 102 to higher energy levels such as shown in FIG. 1B. Under an equilibrium state, higher energy levels are much less populated than the lower energy levels. One of the requirements of laser action is population inversion, which can involve having a larger population of the elements in the gain element 102 in the higher levels than in the lower levels. The energy pump 104 can establish a population inversion in the gain element 102. The pump 104 can be based on optical, electrical, thermal or chemical techniques, depending on the type of the gain element used.

The optical cavity or resonator 106 can be formed by bounding the gain element 102 by two reflectors or mirrors 105, 107. Light travels in both directions along the cavity axis 108, bouncing back and forth between the two reflectors 105, 107. The light reflects back on itself on the reflectors 105, 107 so that as light passes through the gain medium repeatedly, the light is amplified each time (known as feedback) before it is emitted from an output aperture or lost to diffraction or absorption. The optical resonator 106 can produce gain in the gain element 102 to overcome the losses due to, for example, photons straying away from the active medium 102, and/or losses inside the active medium 102 due to absorption and/or scattering. The optical resonator 106 can also provide directionality to the laser beam 120 along an optical axis 108. Photons which are either not of the correct frequency (and thus not of the correct energy) or do not travel along the optical axis 108 are lost. On one end of the active medium 102, the mirror 105 can be a total reflector. On an opposite end of the active medium 102, the mirror 107 can be partially reflecting and partially transmissive, also known as an output coupler. The laser beam 120 can exit the cavity 106 from the output coupler 107, which is partially transmissive.

Figure 2A:
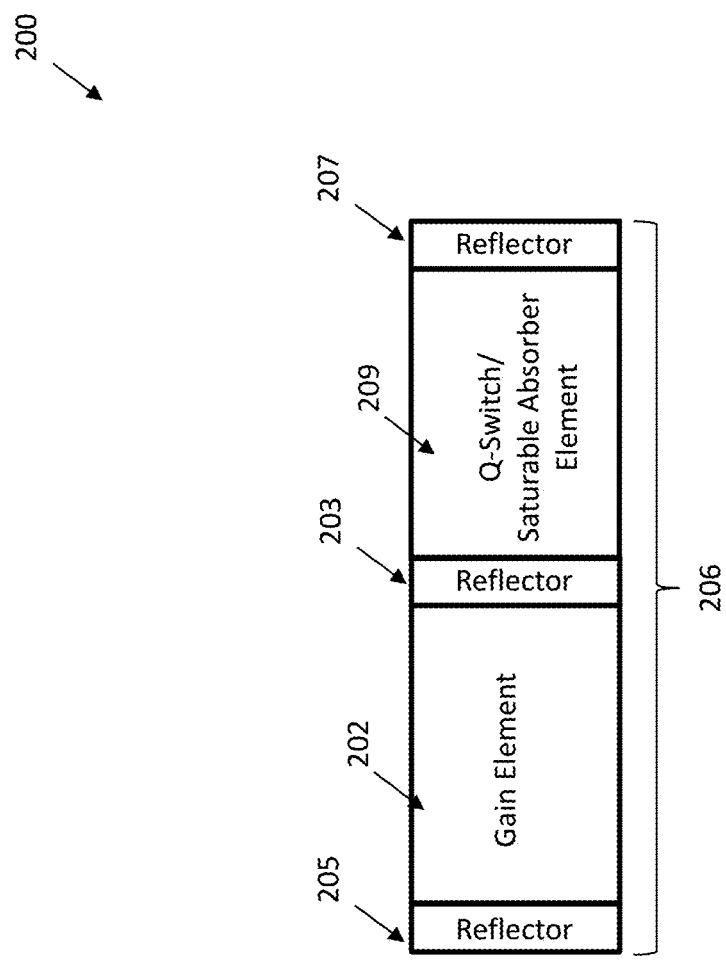

FIG. 2A illustrates schematically a microchip pulsed laser 200. The microchip pulsed laser 200 can include a gain element 202 and a Q-switch 209 bound by the mirrors or reflectors 205, 207, forming an optical cavity 206. The gain element 202 and the Q-Switch 209 can be separated by another mirror or reflector 203. Q switching is a method for obtaining energetic pulses from lasers by modulating intracavity losses. Including a Q-switch in the laser can allow the pulse duration to be in the nanosecond range. The energy of the pulse generated with a Q-switched microchip laser, such as the laser 200, can be higher than the saturation energy of the gain element 202.

Q switching can be achieved using active Q-Switch components or passive Q-Switch components. For active Q switching, an active control element modulates the intracavity losses. A laser pulse is formed shortly after an electrical trigger signal from the active control element arrives. Having an active control element (and the associated electronics) can make the pulsed laser more complex, more expensive, and/or reduces the reliability of the laser under the field conditions than having passive Q-switching components.

Figure 2B:
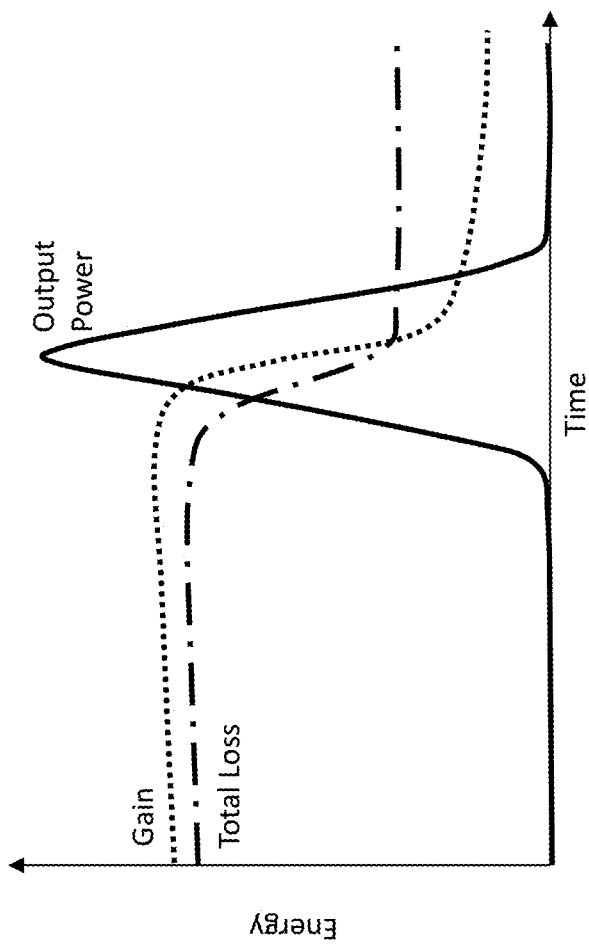

Passive Q-switching (also known as self Q-switching) can be achieved with a saturable absorber element 209 that automatically modulates the intra-cavity losses. As shown in FIG. 2B, a laser pulse, as indicated by a spike, is formed as soon as the energy stored in the gain element 202 (and thus the gain) has reached a sufficiently high level. The saturable absorber element 209 can be cheaper and less complex than an active Q-switch element.

Passively Q-switched microchip lasers disclosed herein can be either monolithic or non-monolithic. When the passively Q-switched microchip lasers are monolithic, the amplifying laser medium or gain element, and the saturable absorbable element form a single component. The formation of a single component can be, for example, due to molecular adhesion and/or epitaxial growth. The cavity mirrors can be directly placed on the single component. Non-monolithic passively Q-switched microchip lasers have at least one part of the cavity that cannot maintain structural integrity without external mechanical support. The mechanical support can be a combination of external object and adhesive material (such as when the elements are glued to an external object), purely mechanical (such as being sustained by friction), or purely adhesive (such as being glued together).

The gain element 202 can include crystals. The crystals in the gain element 202 of the passively Q-switched microchip laser 200 can have a fundamental wavelength at 1064 nm. Many laser gain elements can amplify light of more than one wavelength. For example, Nd: YVO4 can amplify light having a wavelength of 1342 nm in addition to photons having a wavelength of 1064 nm.

However, the gain at the sub-optimal wavelengths (which is the wavelength of interest for malaria detection applications) is lower than the gain at the fundamental wavelength. As described above, the wavelength necessary for generating transient vapor nanobubbles around malaria-specific nanoparticles is between about 1340 nm to about 1350 nm, which are sub-optimal wavelengths of the crystals in the gain element 202. A problem with current passively Q-switched microchip lasers working at sub-optimal wavelengths is that the laser beam at the sub-optimal wavelengths may not meet the required parameters for applications in malaria detection. For example, the energy of the laser light at the sub-optimal wavelengths may be too low and/or the pulse duration may be too long for applications in malaria detection. In order for the laser pulses to meet the requirement for malaria detection applications, the energy of the laser pulses at the sub-optimal wavelengths may need to be increased, and/or the pulse duration may need to be shortened.

The laser pulse output performance parameters (such as pulse duration and/or energy) of passively Q-switched lasers can depend on the design of the microchip laser cavity. Factors of the cavity that can affect the laser pulse output parameters include, but are not limited to, a length of the optical path in the gain element and/or the saturable absorber element, a gain magnitude in the gain element, saturable and non-saturable losses, output coupling, and/or a length of the cavity. The pulse duration is proportional to the cavity length and inversely proportional to the losses. The pulse energy is directly proportional to the pumped energy volume and to the losses.

Accordingly, one way to increase the energy of pulses of the sub-optimal wavelengths is to increase the pumped energy volume, such as by increasing a cross-sectional area of the pump beam. This approach can be limited by various unwanted instabilities caused by the appearance of additional transversal cavity modes that would not be present in a narrower pump beam.

Another way to increase the pulse energy is to increase total losses in the cavity, which in turn requires a higher initial gain in the gain element. Under this approach, a longer cavity is need to due to an increased length in the gain element to produce a higher initial gain. As a result, the output pulses have a longer duration, although the increased pulse duration can then be compensated by increasing the total losses using output coupling. In short, increasing the energy per pulse while maintaining the pulse duration (or vice versa) would require increasing the gain in the gain element.

The increase in the gain of the gain element can be limited and may not deliver the combination of the parameters required for malaria detection applications. The fundamental wavelength with a higher gain typically dominates in the laser cavity unless measures to suppress the fundamental wavelength are introduced. In most types of laser cavities, the fundamental wavelength is suppressed by introducing anti-reflective coatings for the fundamental wavelength, while keeping properties of the coatings favorable for the desired wavelength (for example, for the sub-optimal wavelength of 1342 nm). When the gain of the gain element is increased for the sub-optimal wavelength, the effect of exponential relative gain increase for the fundamental wavelength can eventually overcome the suppression of the unwanted fundamental wavelength provided by the anti-reflective coatings.

Specifically, the gain coefficient in the gain element depends on the density of excited ions and the probability of stimulated emission (also known as stimulated emission cross-section). Stimulated emission cross-section is wavelength dependent, while the density of exited ions is wavelength independent. In conjunction with an exponential overall gain dependency on the gain coefficient, the ratio of overall gains for different wavelengths is exponentially dependent on the excitation level. As a result, certain increases of the overall gain at sub-optimal wavelengths can lead to an even higher gain increase for the fundamental wavelength. In some instances, depending on the reflectivity of the mirrors 203, 205, 207 of FIG. 2A, lasing at the unwanted wavelength of 1064 nm can begin once the gain reaches about 166, whereas the gain for the desired wavelength of 1342 nm can be less than 3 at the same time, as the simulated emission cross-section of the wanted, sub-optimal wavelengths can be about 5 times smaller than the simulated emission cross-section of the fundamental wavelength.

In addition, using the laser 200 as an example, as the reflector surfaces in the laser 200 are generally parallel to one another, reflection of light along the cavity axis can add up to increase feedback to a high gain active medium. The parallel surfaces can also lead to resonant modes, which can result in an increased reflection from anti-reflective coating. The probability of resonant modes being present can also be increased when the gain element crystal increases in temperature.

The parameters of the output coupler and the saturable absorber element in the laser 200 may also not be favorable for outputting pulses of high energy and short duration. For example, the laser pulse energy can be increased and/or the pulse duration can be reduced in the laser 200 by increasing a modulation depth of the saturable absorbable element 209. The modulation depth is the maximum change in absorption (or reflectivity) by the saturable absorber element that can be induced by incident light of a given wavelength. In addition, the pulse duration can be shortened by increasing the transmission of the output coupler 207. However, as the parameters of the output coupler 207 and the saturable absorber elements 209 are related, generally the transmission of the output coupler 207 needs to be similar to the modulation depth of the saturable absorber 209. As a result, increasing the transmission of the output coupler 207 is in tension with increasing the modulation depth of the saturable absorber element 209.

In conclusion, relying solely on anti-reflective coatings with reduced reflection for the unwanted wavelengths fail to provide sufficient suppression of the unwanted wavelengths when higher energy and shorter pulse duration is demanded, such as in the malaria detection application.

Overview of Example Microchip Lasers Suitable for Malaria Detection

It can be desirable for passively Q-switched microchip lasers to include suppression techniques for the unwanted fundamental wavelength in addition to anti-reflective coatings, and/or to increase the pulse energy and/or shorten the pulse duration of a sub-optimal wavelength to deliver the required combination of the laser pulse parameters for malaria detection applications. The passively Q-switched microchip lasers also include other components that a person skilled in the art would understand to be included in such devices based on the disclosure herein, for example but not limited to, heat sinks or other thermal regulation structures. Such components are not discussed in this disclosure in detail for brevity.

The present disclosure provides unwanted fundamental wavelength suppression techniques, such as inclined surfaces with specific coatings on each surface and/or arranged in specific spatial orders. The inclined surfaces do not form the laser cavity or introduce additional elements. The inclined surfaces as disclosed herein are aimed and optimized for the suppression of unwanted, or unwanted and dominating, wavelengths.

The suppression techniques disclosed herein can also increase the pulse energy and/or shorten the pulse duration of the wanted, or wanted and sub-optimal, wavelengths by lowering the reflectivity of the output coupler and the transmission of the saturable absorber element of the wanted wavelengths. Higher energy and shorter pulses can be obtained despite the increase in cavity length due to a longer gain element and a longer saturable absorber. Although the pump to lasing efficiency may be lowered by the increased cavity length, the reduction in efficiency can be compensated by providing a more powerful pump.

The techniques disclosed herein can increase the output pulse energy and decrease the pulse duration for sub-optimal pulse wavelength by one or more of the following features and obvious variations thereof based on the disclosure herein: having inclined surfaces that can suppress optical feedback of unwanted wavelengths from internal surfaces along a laser cavity axis; having inclined surfaces that can reflect unwanted wavelengths away from the laser cavity axis, thus increasing losses along the laser cavity axis; having inclined surfaces that can be used as mirrors to pump the cavity from inside the cavity; double-passing the pump to increase excitation of gain element; protecting the saturable absorber element from bleaching by the pump radiation to increase the lifetime of the laser; having a folding mirror that can work as a filter for unwanted wavelengths to increase losses for unwanted wavelength; having two-wavelength coatings that can replace triple-wavelength coatings (for the pumping, lasing and wanted wavelengths) to reduce the complexity of coatings and/or improve parameters on important specifications (for example, reflectivity for unwanted wavelengths); and/or having additional elements (intra-cavity and/or exo-cavity) that can act as a part of the pump shaping optics.

Examples of a passively Q-switched microchip laser with additional unwanted wavelength suppression techniques, such as for malaria detection applications, are described below with reference to FIGS. 3A to 9. The passively Q-switched microchip lasers described below can be non-monolithic or monolithic. It should be appreciated from the disclosure herein that different features of the passively Q-switched microchip laser embodiments disclosed below are for illustration purposes, and any feature, structure, or component that is described and/or illustrated in one passively Q-switched microchip laser embodiment in this specification can be modified, and/or used with or instead of any feature, structure, or component that is described and/or illustrated in any other passively Q-switched microchip laser embodiments in this specification. Additionally, one or more of the features described for the illustrative embodiments herein can be excluded from these and other embodiments.

Figure 3A:
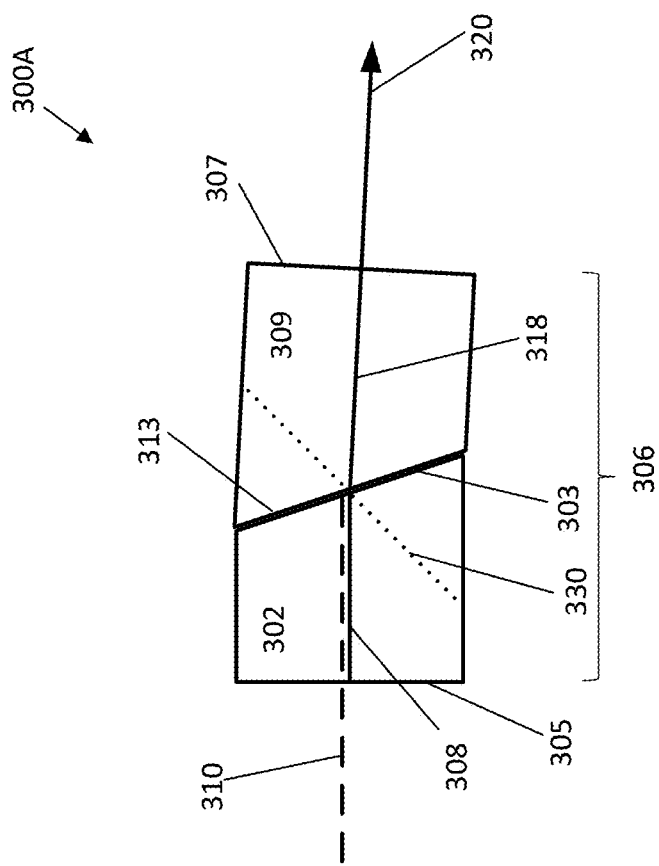

FIG. 3A illustrates a passively Q-switched microchip laser 300A having a laser cavity 306 bound by a reflector 305 and an optical coupler 307. A gain element 302 can be located in the cavity 306. The gain element 302 can be solid crystals. The gain element 302 can have a first axis 308.

The gain element 302 can have a first, non-inclined gain element surface, which can optionally be generally perpendicular to the first axis 308. The first axis 308 can be along a central longitudinal axis of the gain element 302. In FIG. 3A, the reflector 305 is located on the first surface of the gain element 302. For example, the reflector 305 can be coated into the first surface of the gain element 302. In other embodiments and throughout the disclosure where the reflector is coated onto a surface, the reflector can include a separate mirror placed adjacent to the surface. The gain element 302 can have a second, inclined gain element surface that is opposite the first surface. The inclined surface of the gain element 302 can be at an angle (for example, an acute angle) to the first axis 308. The inclined gain element surface can also include a reflector 303, such as a coating on the inclined gain element surface.

The laser 300A can also include a saturable absorber element 309 in the cavity 306 adjacent the gain element 302. The saturable absorber element 309 can have a second axis 318. The second axis 318 can be along a central longitudinal axis of the saturable absorber element 309. The saturable absorber element 309 can have a first, non-inclined surface, which can optionally be generally perpendicular to the second axis 318. The optical coupler 307 can be located on the first surface of the saturable absorber element 309. The saturable absorber element 309 can also have a second, inclined surface that is opposite the first surface. The inclined surface can be at an angle (for example, an acute angle) to the second axis 318. The inclined saturable absorber element surface can include a reflector 313, such as a coating on the inclined saturable absorber element surface.

As shown in FIG. 3A, the inclined surfaces of the gain element 302 and the saturable absorber element 309 can face each other, and the first surfaces of the gain element 302 and the saturable absorber element 309 can face away from each other. The inclined surfaces of the gain element 302 and the saturable absorber element 309 can be near each other or mechanically coupled to each other. The close proximity of the two inclined surfaces can result in a shorter cavity 306. In the laser 300A, the inclined surfaces of the gain element 302 and the saturable absorber element 309 can be generally parallel such that the first and second axes 308, 318 of the gain element 302 and the saturable absorber element 309 can be generally collinear, for example, at an angle less than about 10 degree, or less than about 5 degree of each other.

The inclined surfaces of the gain element 302 and the saturable absorber element 309 need not be parallel to each other.

The laser 300A can be optically pumped at a predetermined pump wavelength. The pump wavelength can be different from the fundamental wavelength and/or sub-optimal wavelengths of the gain element crystals. A pumping beam path, as shown by a dashed line 310, can be directed to the cavity 306 from the reflector 305 end. The reflector 305 can be anti-reflective or substantially anti-reflective of the pump wavelength so that substantially all of the pump beam travel through the gain element 302 toward the inclined surface of the gain element 302. The reflector 303 can be reflective or highly reflective of the pump wavelength. The reflector 313 can also be reflective or highly reflective of the pump wavelength. The reflectors 303 and 313 can thus protect the saturable absorber element 309 from bleaching by the pump radiation.

Energy from the pump can produce gain and subsequent simulated emission of a fundamental and unwanted wavelength (such as about 1064 nm) and sub-optical and wanted wavelengths (such as from about 1340 nm to 1350 nm) in the gain element 302. The reflector 305 can be anti-reflective of the unwanted wavelength. The optical coupler 307 can also be anti-reflective of the unwanted wavelength. The reflectors 303, 313 can be anti-reflective or have low reflectivity for the unwanted wavelength. Light of the fundamental and unwanted wavelength, upon reaching the non-inclined and/or inclined surfaces of the gain element 302 can be suppressed by the anti-reflective reflectors 303, 305, 307, 313 by reducing feedback of the unwanted wavelength.

In addition, as anti-reflective coatings cannot let 100% of light pass through, in particular, anti-reflective coating may not be sufficiently transparent at the unwanted wavelength, a small portion (for example, as low as about 0.25% or about 0.1%) of light of the unwanted wavelength can still be reflected into the gain element 302 by the reflector 303, as shown by the dotted line 330, away from the first axis 308, therefore reducing feedback of the unwanted wavelength along the first axis 308. As described above, light that does not travel along the laser cavity axis is lost and increasing the losses in the cavity can increase the laser pulse energy. In the saturable absorber element 309, the anti-reflective reflector 313 can also suppress the unwanted wavelengths in the saturable absorber element 309 by reflecting a portion of the unwanted wavelengths away from the second axis 318, as shown by the dotted line 330.

The reflector 305 can be a total reflector, or highly reflective of the wanted wavelengths. The optical coupler 307 can be partially reflective or have a specified reflectivity (for example, 60%, 50%, 40%, or others) of the wanted wavelengths. The reflectors 303, 313 can be anti-reflective of the wanted wavelength. As a result, the wanted wavelengths can be amplified along the first and second axes 308, 318 without being affected by the inclined surfaces of the gain element 302 and the saturable absorber element 309. A laser beam of the wanted wavelength, as illustrated by the arrow 320, can be outputted from the optical coupler 307 that is on the saturable absorber element 309 side.

Figure 3B:
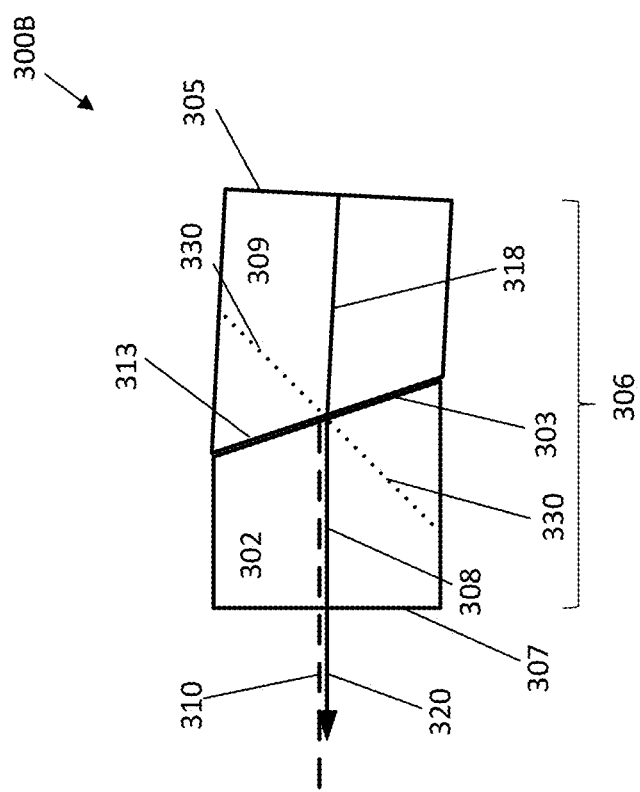

FIG. 3B illustrates a laser 300B that can have any of features of the laser 300A, except as described below. The same or similar features in the laser 300A and the laser 300B share the same reference numbers.

In FIG. 3B, the total reflector 305 is on the saturable absorber element 309 side, and the output coupler 307 is on the gain element 302 side. Specifically, the total reflector 305 is adjacent to the perpendicular surface of the saturable absorber element 309 and the output coupler 307 is adjacent to the perpendicular surface of the gain element 302.

As shown by the dashed line 310, the pump beam can still enter the laser cavity 306 on the gain element 302 side. The pump beam passes the output coupler 307 and travels toward the reflector 305. The laser beam of wanted wavelengths, as shown by the arrow 320, can exit the laser cavity 306 on the gain element 302 side.

The reflectivity of the surfaces in FIGS. 3A and 3B for the wanted, pump, and unwanted wavelengths is summarized in Table 1 below. "AR" denotes anti-reflection (minimal reflection possible); "HR" denotes high reflectivity (maximum reflection possible); "PR" denotes preferably high reflectivity (wherein higher reflectivity is preferable to lower reflectivity) or preferably having reflectivity; "LR" denotes preferably low reflectivity (wherein lower reflectivity is preferable to higher reflectivity); "% R" denotes specified reflectivity for example, 60%, 50%, 40%, or others); and "UR" denotes undefined reflectivity (where reflectivity for a certain wavelength is not applicable).

TABLE 1

| Surface (Ref. No.) | Reflectivity for Wavelengths | | |
|---|---|---|---|
| | Wanted (Lasing) | Pump | Unwanted (Parasitic) |
| 305 | HR | AR | AR |
| 303 | AR | PR or HR | AR or LR |
| 313 | AR | HR or PR | AR or LR |
| 307 | % R | UR | AR |

Figure 4:
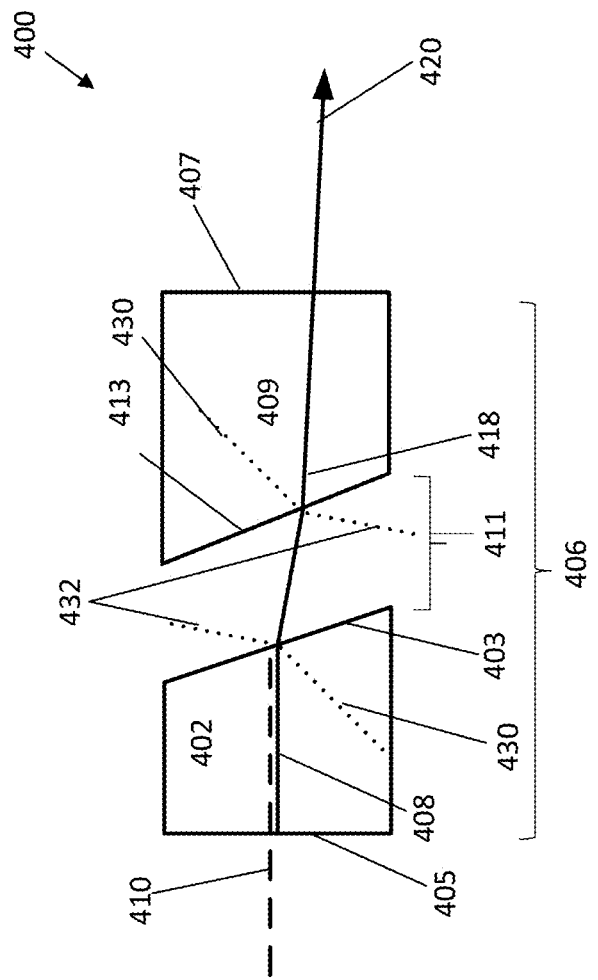

FIG. 4 illustrates schematically an example laser 400 incorporating features of the laser 300A. The reference numbers of the same or similar features in the laser 300A and the laser 300B share the same last two digits. Accordingly, features of the laser 400 can be incorporated into features of the laser 300A and features of the laser 300A can be incorporated into features of the laser 400.

The passively Q-switched microchip laser 400 can have a laser cavity 406 bound by a total reflector 405 and an optical coupler 407. A gain element 402 can be located in the cavity 406. The gain element 402 can have a first axis 408.

The gain element 402 can have a first gain element surface, which can optionally be generally perpendicular to the first axis 408. The reflector 405 is located on the first surface of the gain element 402. The gain element 402 can have a second, inclined gain element surface that is opposite the first surface. The inclined surface of the gain element 402 can be at an angle to the first axis 408. The inclined gain element surface can also include a reflector 403, such as a coating on the inclined gain element surface.

The laser 400 can also include a saturable absorber element 409 in the cavity 406. The saturable absorber element 409 can have a second axis 418. The saturable absorber element 409 can have a first surface, which can optionally be generally perpendicular to the second axis 418. The optical coupler 407 can be located on the first surface of the saturable absorber element 409. It is also possible to have the total reflector 405 on the saturable absorber element 409 side and the optical coupler 407 on the gain element 402 side. The saturable absorber element 409 can also have a second, inclined surface that is opposite the first surface. The inclined surface can be at an angle to the second axis 418. The inclined saturable absorber element surface can include a reflector 413, such as a coating on the inclined saturable absorber element surface.

As shown in FIG. 4, the inclined surfaces of the gain element 402 and the saturable absorber element 409 can face each other, and the first surfaces of the gain element 402 and the saturable absorber element 409 can face away from each other. The inclined surfaces of the gain element 402 and the saturable absorber element 409 can be separated by a gap 411. The inclined surfaces of the gain element 402 and the saturable absorber element 409 can be generally parallel (for example, at an angle less than about 10 degree, or less than about 5 degree). The first and second axes 408, 418 of the gain element 402 and the saturable absorber element 409 can be generally collinear. The inclined surfaces of the gain element 402 and the saturable absorber element 409 need not be parallel to each other.

A pump beam path, as shown by a dashed line 410, can be directed to the cavity 406 from the total reflector 405 end. The total reflector 405 can be anti-reflective or substantially anti-reflective of the pump wavelength so that substantially all of the pump beam travel through the gain element 402 toward the inclined surface of the gain element 402. The reflector 403 can be reflective or highly reflective of the pump wavelength. The reflector 413 can also be reflective or highly reflective of the pump wavelength. The reflectors 403 and 413 can thus protect the saturable absorber element 409 from bleaching by the pump radiation.

Energy from the pump can produce gain and subsequent simulated emission of a fundamental and unwanted wavelength (such as about 1064 nm) and sub-optical and wanted wavelengths (such as from about 1340 nm to 1350 nm) in the gain element 402. The total reflector 405 can be anti-reflective of the unwanted wavelength. The optical coupler 407 can also be anti-reflective of the unwanted wavelength. The reflector 403 can be anti-reflective or have low reflectivity for the unwanted wavelength. Light of the fundamental and unwanted wavelength, upon reaching the non-inclined and/or inclined surfaces of the gain element 402 can be suppressed by the anti-reflective reflectors 403, 405, 407, 413, which can reduce feedback of the unwanted wavelengths. In addition, a small portion (for example, as low as about 0.25% or about 0.1%) of light of the unwanted wavelength can still be reflected by the reflectors 403, 413, as shown by the dotted line 430, away from the first axis 408 and/or the second axis 418, which can increase total losses in the cavity 406.

In the laser 400, the reflectors 413 can be reflective or have high reflectivity of the unwanted wavelength. In the gap 411, light of the unwanted wavelength incident on the inclined reflector 413 can be reflected away from the second axis 418, as indicated by the dotted line 432. The gap 411 allows the reflector 413 to be highly reflective or reflective of the unwanted wavelength without potentially increasing amplified spontaneous emission. In addition, although the reflector 403 is anti-reflective or have low reflectivity of the unwanted wavelength, the reflector 403 can still reflect a small portion of the light in the gap that is incident on the inclined reflector 403 away from the first axis 408. Because of the gap 411, the reflected light 432 of the unwanted wavelength travels into the atmosphere rather than into the gain element 402 or the saturable absorbable element 409, which can further reduce or suppress feedback of the unwanted wavelength along the axes 408, 418.

The total reflector 405 can be highly reflective of the wanted wavelength. The optical coupler 407 can be partially reflective or have a specified reflectivity (for example, 60%, 50%, 40%, or others) of the wanted wavelength. The reflectors 403, 413 can be anti-reflective of the wanted wavelength. At the gap 411, light of the wanted wavelengths can be amplified along the first and second axes 408, 418, being bent from the first axis 408 toward a slightly offset and generally parallel second axis 418 due to refraction. A laser beam of the wanted wavelength, as illustrated by the arrow 420, can be outputted from the optical coupler 407.

The reflectivity of the surfaces in FIG. 4 for the wanted, pump, and unwanted wavelengths is summarized in Table 2 below.

TABLE 2

| Surface | Reflectivity for Wavelengths | | |
|---|---|---|---|
| (Ref. No.) | Wanted (Lasing) | Pump | Unwanted (Parasitic) |
| 405 | HR | AR | AR |
| 403 | AR | PR or HR | AR or LR |
| 413 | AR | HR or PR | HR or PR |
| 407 | % R | UR | AR |

Figure 5A:
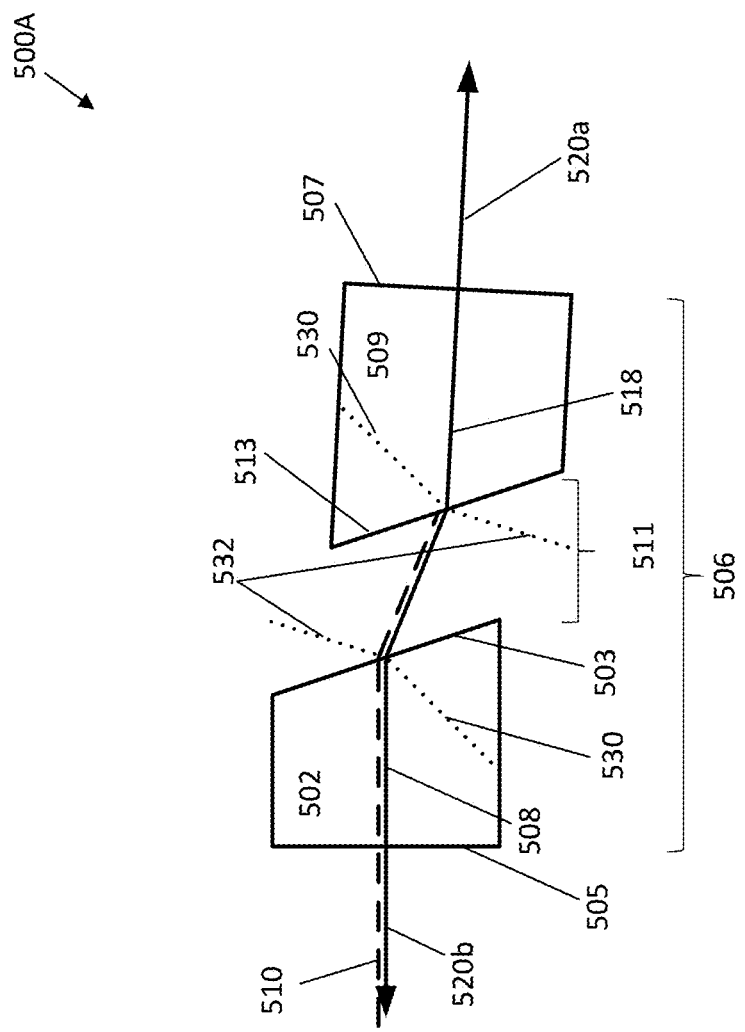

Turning to FIG. 5A, an example laser 500A can have any of features of the laser 400 except as described below. The reference numbers of the same or similar features in the laser 400 and the laser 500A share the same last two digits. Accordingly, features of the laser 500A can be incorporated into features of the laser 400 and features of the laser 400 can be incorporated into features of the laser 500A.

The passively Q-switched microchip laser 500A can have a laser cavity 506 bound by a reflector 505 and a reflector 507. A gain element 502 can be located in the cavity 506. The gain element 502 can have a first axis 508. The gain element 502 can have a first gain element surface, which can optionally be generally perpendicular to the first axis 508. The reflector 505 is located on the first surface of the gain element 502. The gain element 502 can have a second, inclined gain element surface that is opposite the first surface. The inclined surface of the gain element 502 can be at an angle to the first axis 508. The inclined gain element surface can also include a reflector 503, such as a coating on the inclined gain element surface.

The laser 500A can also include a saturable absorber element 509 in the cavity 506. The saturable absorber element 509 can have a second axis 518. The saturable absorber element 509 can have a first surface, which can optionally be generally perpendicular to the second axis 518. The mirror 507 can be located on the first surface of the saturable absorber element 509. The saturable absorber element 509 can also have a second, inclined surface that is opposite the first surface. The inclined surface can be at an angle to the second axis 518. The inclined saturable absorber element surface can include a reflector 513, such as a coating on the inclined saturable absorber element surface.

As shown in FIG. 5A, the inclined surfaces of the gain element 502 and the saturable absorber element 509 can face each other, and the first surfaces of the gain element 502 and the saturable absorber element 509 can face away from each other. The inclined surfaces of the gain element 502 and the saturable absorber element 509 can be separated by a gap 511. The inclined surfaces of the gain element 502 and the saturable absorber element 509 can be generally parallel to each other. The first and second axes 508, 518 of the gain element 502 and the saturable absorber element 509 can be generally parallel and offset from each other. The amount of offset can depend on a width of the gap 511 and/or the amount of bending of the light when the light travels from the gain element 502 into the gap 511 (which can comprise air and thus having a lower density than the crystal gain element 502). The inclined surfaces of the gain element 502 and the saturable absorber element 509 need not be parallel to each other.

A pump beam path, as shown by a dashed line 510, can be directed to the cavity 506 from the reflector 505 end. The reflector 505 can be anti-reflective or substantially anti-reflective of the pump wavelength so that substantially all of the pump beam travels through the gain element 502 toward the inclined surface of the gain element 502. The reflector 503 can be reflective or have low reflectivity of the pump wavelength. The reflector 513 can also be reflective or highly reflective of the pump wavelength. As a result, the pumping beam incident on the reflector 503 travels to the reflector 513 and is reflected back into the gain element 502. This double-passing of the pump beam can increase excitation of the gain element 502. At the same time, the reflectivity of the pump wavelength at the reflector 513 can protect the saturable absorber element 509 from bleaching by the pump radiation.

Energy from the pump can produce gain and subsequent simulated emission of a fundamental and unwanted wavelength (such as about 1064 nm) and sub-optical and wanted wavelengths (such as from about 1340 nm to 1350 nm) in the gain element 502. The reflector 505 can be anti-reflective of the unwanted wavelength. The reflector 507 can also be anti-reflective of the unwanted wavelength. The reflector 503 can be anti-reflective or have low reflectivity for the unwanted wavelength. Light of the fundamental and unwanted wavelengths, upon reaching the inclined surface of the gain element 502 can be suppressed by the anti-reflective reflector 503, which can reduce feedback of the unwanted wavelength as substantially all of the light of the unwanted wavelength exits the gain element 502 and travels toward the inclined surface of the saturable absorber element 509. In addition, a small portion (for example, as low as about 0.25% or about 0.1%) of light of the unwanted wavelength in the gain element 502 can be reflected by the reflector 503, as shown by the dotted line 530, away from the first axis 508, which can increase total losses in the cavity 506.

In the laser 500A, the reflector 513 can be reflective or have high reflectivity of the unwanted wavelength. In the gap 511, light of the unwanted wavelength incident on the inclined reflector 513 can be reflected away from the second axis 508, as indicated by the dotted line 532. In the gap 511, a small portion of light of the unwanted wavelength incident on the inclined mirror 503 can also be reflected in a direction away from the first axis 508, as indicated by the dotted line 532. Because of the gap 511, the reflected light 532 of the unwanted wavelength travels into the atmosphere rather than into the gain element 502 or the saturable absorbable element 509, which can further reduce or suppress feedback of the unwanted wavelength along the first and/or second axis 508, 518.

The reflector 513 can also suppress the unwanted wavelengths by reflecting light of the unwanted wavelengths in the saturable absorber element 509 away from the second axis 518, as shown by the dotted line 530. The reflector 503 can also reflect a small portion of light of the unwanted wavelengths in the gain element 502 away from the first axis 508, as shown by the dotted line 530.

In some embodiments, the reflector 505 can be highly reflective of the wanted wavelength, functioning as the total reflector of the wanted wavelength, and the reflector 507 can be partially reflective or have a specified reflectivity (for example, 60%, 50%, 40%, or others) of the wanted wavelength, functioning as the output coupler. In some embodiments, the reflector 507 can be highly reflective of the wanted wavelength, functioning as the total reflector of the wanted wavelength, and the reflector 505 can be partially reflective or have a specified reflectivity of the wanted wavelength, functioning as the optical coupler. The reflectors 503, 513 can be anti-reflective of the wanted wavelength. As a result, the wanted wavelengths can be amplified along the first and second axes 508, 518 with the light of the wanted wavelengths being bent at the inclined surfaces of the gain element 502 and the saturable absorber element 509 from the first axis 508 to the generally parallel but offset second axis 518. When the reflector 505 is the total reflector and the mirror 507 is the output coupler, a laser beam of the wanted wavelength, as illustrated by the arrow 520a, can be outputted from the reflector 507 that is on the saturable absorber element 509 side. When the reflector 507 is the total reflector and the reflector 505 is the output coupler, a laser beam of the wanted wavelength, as illustrated by the arrow 520b, can be outputted from the reflector 505 that is on the gain element 502 side.

The reflectivity of the surfaces in FIG. 5A for the wanted, pump, and unwanted wavelengths is summarized in Table 3 below.

TABLE 3

| Surface | Reflectivity for Wavelengths | | |
|---|---|---|---|
| (Ref. No.) | Wanted (Lasing) | Pump | Unwanted (Parasitic) |
| 505 | 520a: HR<br>520b: % R | AR | AR |
| 503 | AR | PR or LR | AR or LR |
| 513 | AR | HR or PR | HR or PR |
| 507 | 520a: % R<br>520b: HR | UR | AR |

Figure 5B:
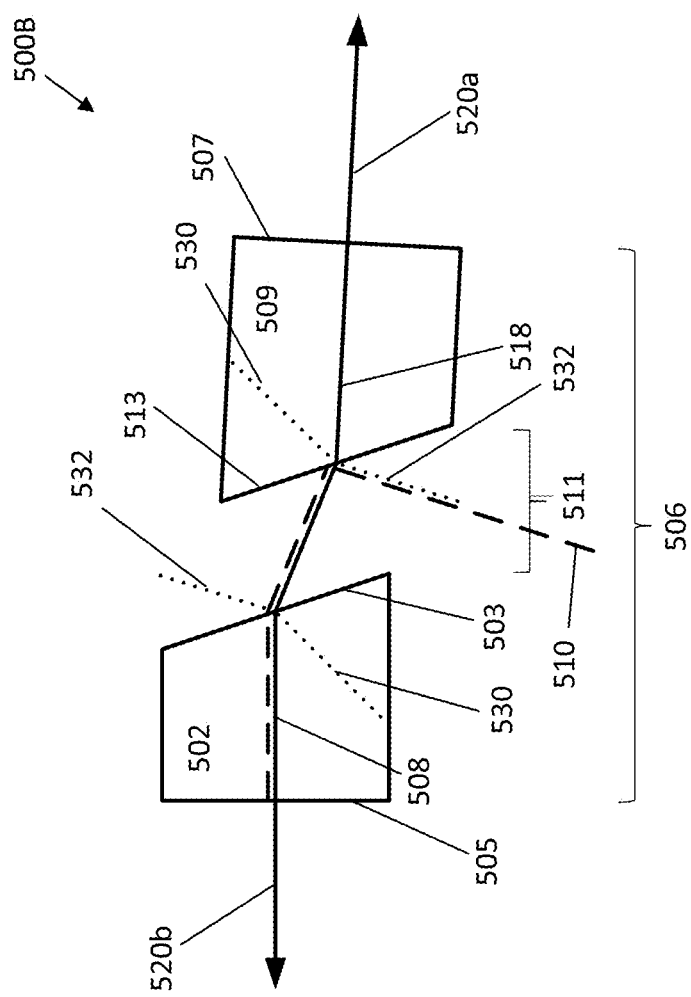

FIG. 5B illustrates a laser 500B that has features of the laser 500A, except as described below. The same or similar features in the laser 500A and the laser 500B share the same reference numbers.

In FIG. 5B, the pump can be directed from the uncoated sides of the laser cavity 506 rather than from the reflector 505 side. A pump beam path, as shown by a dashed line 510, can be directed from inside the cavity 506 to the reflector 513. The reflector 513 can be highly reflective of the pump wavelength so that substantially all of the pump beam in the gap 511 can be reflected by the inclined surface of the saturable absorber element 509 toward the inclined surface of the gain element 502. The reflector 503 can be reflective or have low reflectivity of the pump wavelength. The pump beam incident on the reflector 503 can travels to the reflector 505, which can be highly reflective or at least reflective of the pump wavelength.

As a result, light of the pump wave length can be reflected back into the gain element 502 and double passing of the pump beam can be achieved. This double-passing of the pump beam can increase excitation of the gain element 502. At the same time, the reflectivity of the pump wavelength at the reflector 513 can protect the saturable absorber element 509 from bleaching by the pump radiation.

The reflectivity of the surfaces in FIG. 5B for the wanted, pump, and unwanted wavelengths is summarized in Table 4 below.

TABLE 4

| Surface | Reflectivity for Wavelengths | | |
|---|---|---|---|
| (Ref. No.) | Wanted (Lasing) | Pump | Unwanted (Parasitic) |
| 505 | 520a: HR<br>520b: % R | HR or PR | AR |
| 503 | AR | AR | LR or UR |
| 513 | AR | HR | PR or UR |
| 507 | 520a: % R<br>520b: HR | UR | AR |

Figure 6A:
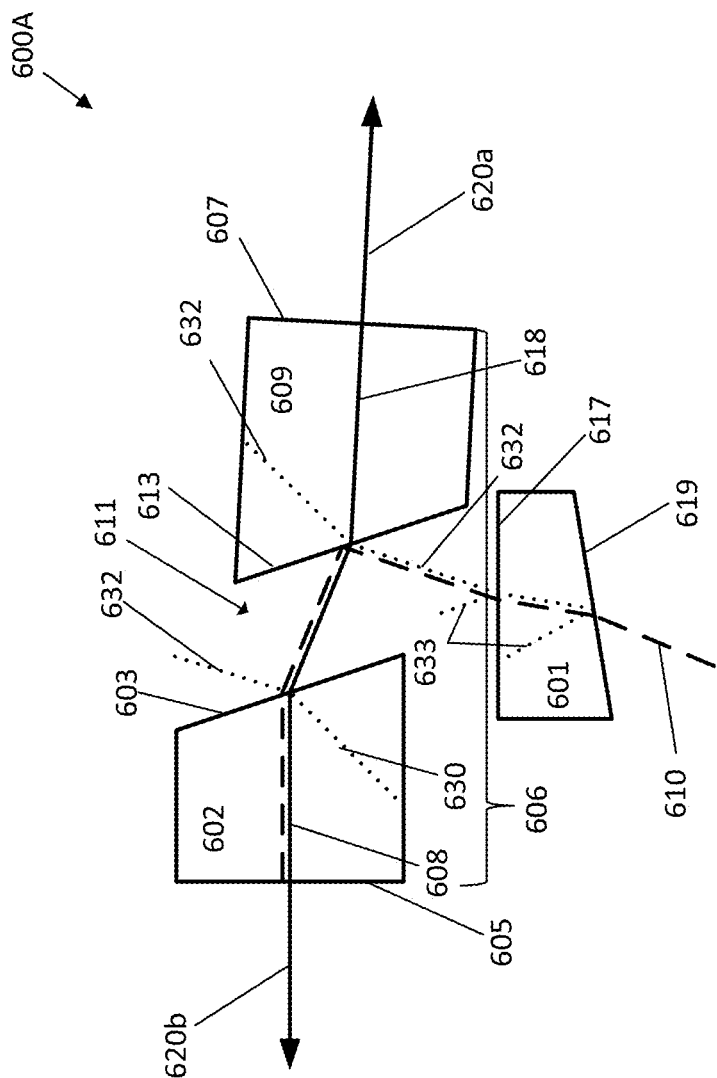
FIG. 6B illustrates schematically an example passively Q-switched micro-chip laser.
FIG. 6C illustrates schematically an example passively Q-switched micro-chip laser.

Turning to FIG. 6A, an example laser 600A can have features of the laser 500B except as described below. The reference numbers of the same or similar features in the laser 500B and the laser 600A share the same last two digits. Accordingly, features of the laser 500B can be incorporated into features of the laser 600A and features of the laser 600A can be incorporated into features of the laser 500B.

The passively Q-switched microchip laser 600A can have a laser cavity 606 bound by a reflector 605 and a reflector 607. A gain element 602 can be located in the cavity 606. The gain element 602 can have a first axis 608. The gain element 602 can have a first gain element surface, which can optionally be generally perpendicular to the first axis 608. The reflector 605 is located on the first surface of the gain element 602. The gain element 602 can have a second, inclined gain element surface that is opposite the first surface. The inclined surface of the gain element 602 can be at an angle to the first axis 608. The inclined gain element surface can also include a reflector 603, such as a coating on the inclined gain element surface.

The laser 600A can also include a saturable absorber element 609 in the cavity 606. The saturable absorber element 609 can have a second axis 618. The saturable absorber element 609 can have a first surface, which can optionally be generally perpendicular to the second axis 618. The reflector 607 can be located on the first surface of the saturable absorber element 609. The saturable absorber element 609 can also have a second, inclined surface that is opposite the first surface. The inclined surface can be at an angle to the second axis 618. The inclined saturable absorber element surface can include a reflector 613, such as a coating on the inclined saturable absorber element surface.

As shown in FIG. 6A, the inclined surfaces of the gain element 602 and the saturable absorber element 609 can face each other, and the first surfaces of the gain element 602 and the saturable absorber element 609 can face away from each other. The inclined surfaces of the gain element 602 and the saturable absorber element 609 can be separated by a gap 611. The inclined surfaces of the gain element 602 and the saturable absorber element 609 can be generally parallel to each other. The first and second axes 608, 618 of the gain element 602 and the saturable absorber element 609 can be generally parallel and offset from each other. The amount of offset can depend on the amount of bending of the light when the light travels from the gain element 602 into the gap 611. The inclined surfaces of the gain element 602 and the saturable absorber element 609 need not be parallel to each other.

A pump beam path, as shown by a dashed line 610, can be directed into the gap 611 of the cavity 606 and can first reach the reflector 613. The laser 600A can include an exo-cavity folding and/or deflecting element 601. The folding and/or deflecting element 601 can be located outside the cavity 606. The pump beam can be deflected before entering the gap 611 of the cavity 606. The folding and/or deflecting element 601 can have a coated first surface 617 and a coated second surface 619. The coated first and second surfaces 617, 619 can be anti-reflective of the pump wavelength. The first surface 617 can be highly reflective or at least reflective of the unwanted wavelength. The second surface 619 can be optionally reflective of the unwanted wavelength. As shown in FIG. 6A, the folding and/or deflecting 601 can have a generally flat first surface 617 and a generally flat second surface 619. The generally flat second surface 619 can be inclined relative to the first surface 617.

Figure 8A:
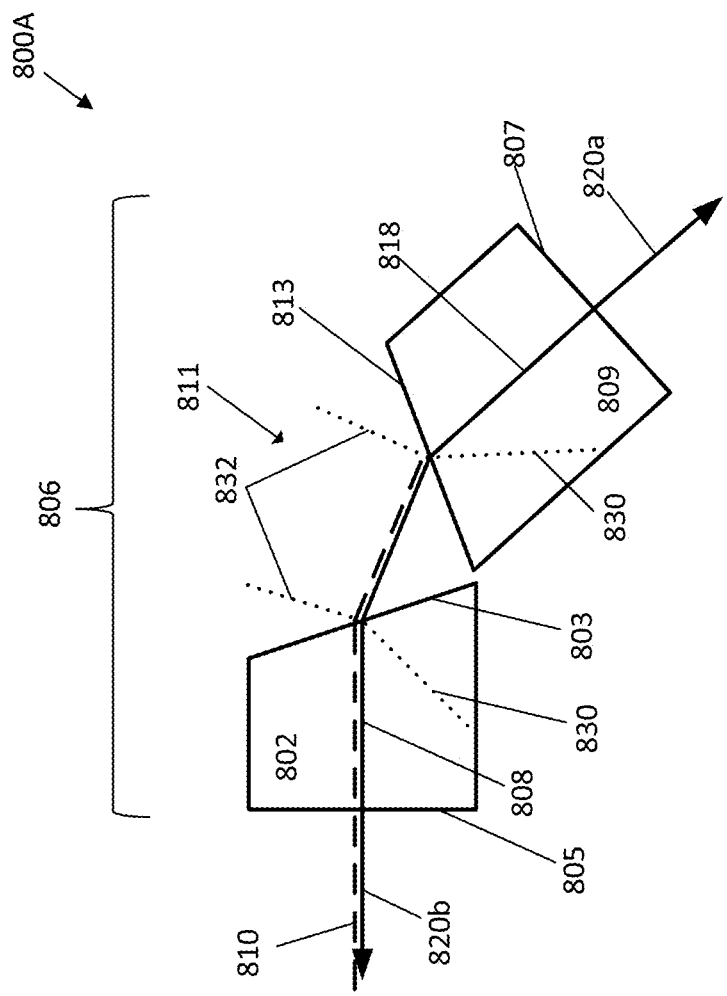
FIG. 8A illustrates schematically an example passively Q-switched micro-chip laser.

As indicated by the dotted lines 633, the first surface 617 and/or the second surface 619 of the folding and/or deflecting element 601 can deflect, and thereby isolate, feedback of the unwanted wavelengths from the pump shaping optics (see FIG. 8A). The pump shaping optics are configured to delivery and shape the pump beam to the lasers disclosed herein. The angle between the first and second surfaces 617, 619 can allow the reflected unwanted wavelengths as indicated by the dotted lines 633 be generally parallel to each other, in spite of the light being bent at the gap 611 and first surface 617 interface.

The reflector 613 can be highly reflective of the pump wavelength so that substantially all of the pump beam in the gap 611 can be reflected by the inclined surface of the saturable absorber element 609 toward the inclined surface of the gain element 602. The reflector 613 can protect the saturable absorber element 609 from bleaching by the pump radiation. Double passing of the pump beam can be achieved by the reflector 605 being highly reflective or at least reflective of the pump wavelength.

The reflectivity of the surfaces in FIG. 6A for the wanted, pump, and unwanted wavelengths is summarized in Table 5 below.

TABLE 5

| Surface | Reflectivity for Wavelengths | | |
|---|---|---|---|
| (Ref. No.) | Wanted (Lasing) | Pump | Unwanted (Parasitic) |
| 605 | 520a: HR<br>520b: % R | HR or PR | AR |
| 603 | AR | AR | LR or UR |
| 613 | AR | HR | PR or UR |
| 607 | 520a: % R<br>520b: HR | UR | AR |
| 617 | UR | AR | HR or PR |
| 619 | UR | AR | PR or UR |

Figure 6B:
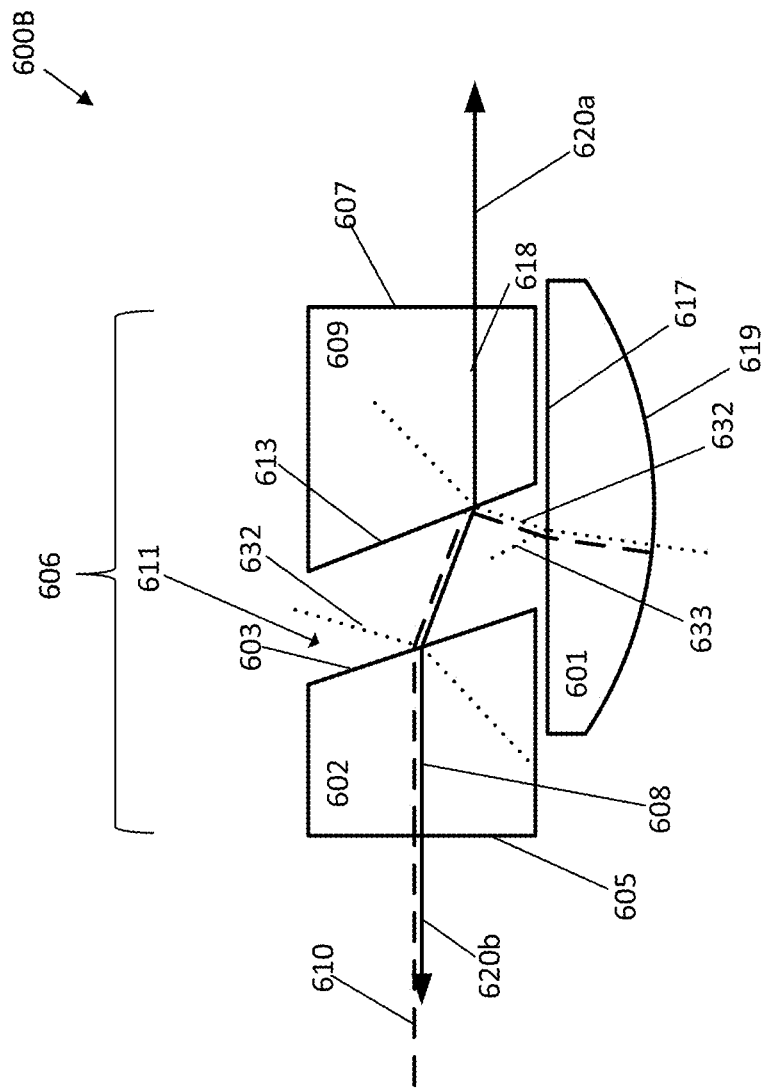

FIG. 6B illustrates an example laser 600B can have features of the laser 600A except as described below. The same or similar features in the laser 600A and the laser 600B share the same reference numbers. Accordingly, features of the laser 600A can be incorporated into features of the laser 600B and features of the laser 600B can be incorporated into features of the laser 600A.

In the laser 600B, the exo-cavity folding and/or deflecting element 601 can be coupled to the cavity 606 via adhesion. The folding and/or deflecting element 601 can have a flat first surface 617 and a curved or dome-shaped second surface 619. The folding and/or deflecting element 601 can be positioned such that light incident on the curved second surface 619 from inside the folding and/or deflecting element 601 is normal to the curved second surface 619. As a result, light incident on the curved second surface 619 can be reflected along its incoming path (such as the pump beam) and/or continue past the second surface 619 undeflected (such as the unwanted wavelength).

In the laser 600B, the pump beam can be introduced from the reflector 605 side of the cavity, with the reflector 605 being anti-reflective of the pump wavelength. Double passing of the pump beam can be achieved by the coated flat surface 617 being anti-reflective of the pump wavelength and the coated curved surface 619 being highly reflective of the pump wavelength. The folding and/or deflecting element 601 can thus reflect back the pump beam along its incoming path into the cavity 606. The reflected pump beam can be redirected into the gain element 602 by the highly reflective reflector 613.

The first surface 617 can be highly reflective or at least reflective of the unwanted wavelength so that the first surface 617 can reflect or deflect the unwanted wavelength into the gap 611 to increase the total losses in the cavity 606. The second surface 619 can be anti-reflective of the unwanted wavelength. Light of the unwanted wavelength can incident on the second surface 619 can exit the folding and/or deflecting element 601 undeflected, which can increase total losses in the cavity 606. The second surface 619 needs not reflect the unwanted wavelength in the laser 600B as the pump shaping optics are located adjacent the reflector 605 rather than adjacent the second surface 619.

The reflectivity of the surfaces in FIG. 6B for the wanted, pump, and unwanted wavelengths is summarized in Table 6 below.

TABLE 6

| Surface | Reflectivity for Wavelengths | | |
|---|---|---|---|
| (Ref. No.) | Wanted (Lasing) | Pump | Unwanted (Parasitic) |
| 605 | 520a: HR<br>520b: % R | AR | AR |
| 603 | AR | AR | LR or UR |
| 613 | AR | HR | PR or UR |
| 607 | 520a: % R<br>520b: HR | UR | AR |
| 617 | UR | AR | HR or PR |
| 619 | UR | HR | AR |

Figure 6C:
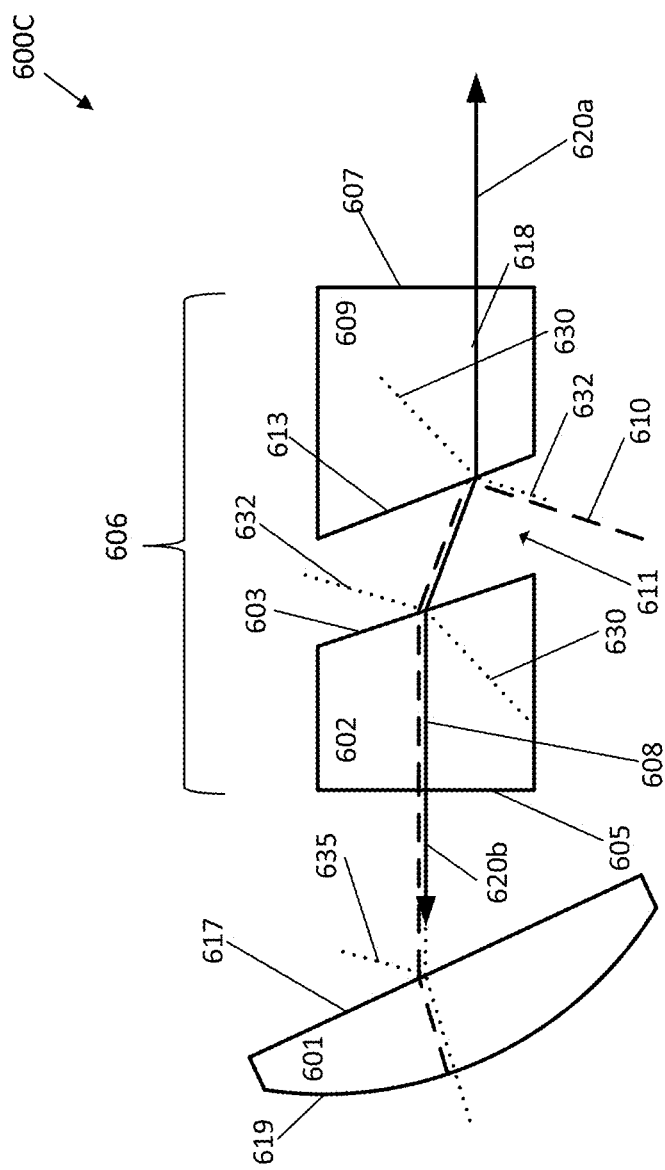

Turning to FIG. 6C, an example laser 600C can have features of the lasers 600A, 600B except as described below. The same or similar features in the lasers 600A, 600B, 600C share the same reference numbers. Accordingly, features of the lasers 600A, 600B, 600C can be incorporated into one another.

In the laser 600C, the exo-cavity folding and/or deflecting element 601 can be located next to the reflector 605 and the gain element 602. The folding and/or deflecting element 601 can have a flat first surface 617 and an opposing curved or dome-shaped second surface 619, the first surface 617 facing the reflector 605. The folding and/or deflecting element 601 can be positioned such that light incident on the curved second surface 619 from inside the folding and/or deflecting element 601 is normal to the curved second surface 619. As a result, light incident on the curved second surface 619 can be reflected along its incoming path (such as the pump wavelength) and/or continue past the second surface 619 undeflected (such as the unwanted wavelengths). The position of the folding and/or deflecting element 601 can depend on the amount of bending of the light traveling across the air and element 601 interface. The flat first surface 617 can be inclined relative to the first axis 608 and/or the second axis 618.

The pump beam can be initially directed to the inclined reflector 613 and reflected toward the inclined surface 603, which is anti-reflective of the pump wavelength, similar to the laser 600A. In the laser 600C, the reflector 605 can have low reflectivity or even unspecified reflectivity of the pump wavelength. With the first surface 617 being anti-reflective of the pump wavelength and the second surface 619 being highly reflective of the pump wavelength, the folding and/or deflecting element 601 can reflect back or re-image the pump beam transmitted through the reflector 605 to achieve double-passing of the pump radiation through the gain element 602. Accordingly, the reflector 605 in the laser 600C can have a two-wavelength coating (wanted and unwanted wavelengths) instead of a triple-wavelength coating (wanted, unwanted, and pump wavelengths). The two-wavelength coating can reduce complexity of the coatings and/or improve parameters on other specifications, such as the reflectivity for the unwanted wavelength.

The first surface 617 can be highly reflective or at least reflective of the unwanted wavelength so that the first surface 617 can reflect or deflect the unwanted wavelength into the gap 611 to increase the total losses in the cavity 606. The second surface 619 can be anti-reflective of the unwanted wavelength. Light of the unwanted wavelength incident on the second surface 619 can exit the folding and/or deflecting element 601 undeflected, which can increase total losses in the cavity 606. The second surface 619 needs not reflect the unwanted wavelength in the laser 600C as the pump shaping optics are located adjacent the gap 611 rather than adjacent the reflector 605.

The first surface 617 can also be highly reflective of the wanted wavelength. When the reflector 605 is acting as the output coupler and the reflector 607 is acting as the total reflector, the folding and/or deflecting element 601 can also act as a steering mirror for the generated laser beam as indicated by the arrow 620b. The inclined first surface 617 can deflect the generated laser beam 620b, for example, toward an output fiber (see, for example, FIG. 10A) coupled to the laser 600C.

The reflectivity of the surfaces in FIG. 600C for the wanted, pump, and unwanted wavelengths is summarized in Table 7 below.

TABLE 7

| Surface | Reflectivity for Wavelengths | | |
|---|---|---|---|
| (Ref. No.) | Wanted (Lasing) | Pump | Unwanted (Parasitic) |
| 605 | 620a: HR<br>620b: % R | LR or UR | AR |
| 603 | AR | AR | LR or UR |
| 613 | AR | HR | PR or UR |
| 607 | 620a: % R<br>620b: HR | UR | AR |
| 617 | HR | AR | HR or PR |
| 619 | UR | HR | AR |

Figure 7A:
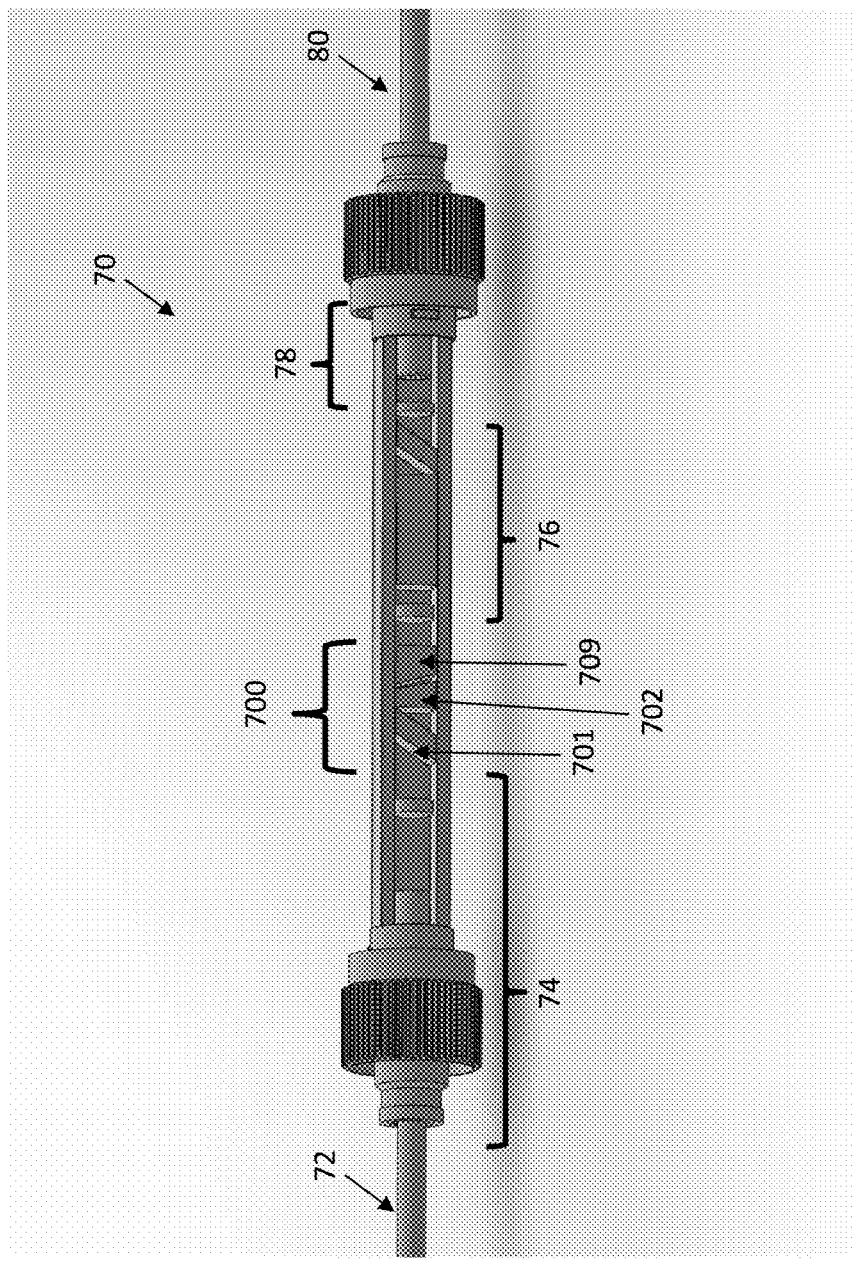
FIG. 7A illustrates an example laser incorporating a passively Q-switched micro-chip laser.

FIG. 7A illustrates a laser system 70 having a passively Q-switched microchip laser 700, which can have a combination of certain features of the lasers 600A, 600B, 600C. The reference numbers of the same or similar features in the lasers 600A, 600B, 600C, 700 share the same last two digits. Accordingly, features of the lasers 600A, 600B, 600C, 700 can be incorporated into one another.

As shown in FIG. 7A, the laser system 70 can have pump shaping optics 74 coupling a pump fiber 72 to the laser 700 on the side of an exo-cavity folding and/or deflecting element 701 and the gain element 702. Second harmonic generation and filtering elements 76 can be coupled to the laser 700 on the side of the saturable absorber element 709.

The second harmonic generation and filtering elements 76 can be coupled via beam delivery optics 78 into an output fiber 80.

Figure 7B:
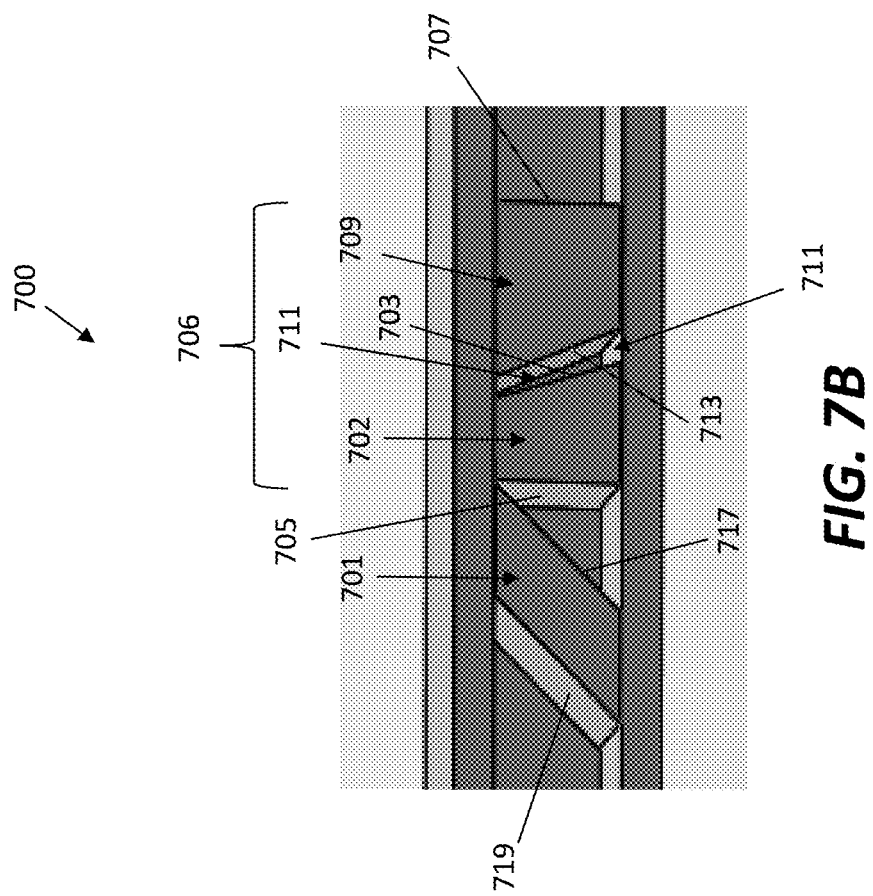
FIG. 7B illustrates an exploded view of the passively Q-switched micro-chip laser in the laser of FIG. 7A.

FIG. 7B illustrates an enlarged view of the laser 700, which can include the exo-cavity folding and/or deflecting element 701, the gain element 702, and the saturable absorber element 709. The exo-cavity folding and/or deflecting element 701 can be adjacent to the reflector 705 and the gain element 702. The gain element 702 can have an inclined surface with one or more coatings 703 on the opposite side of the reflector 705. The saturable absorber element 709 can have an inclined surface with one or more coatings 713 that is separated from the inclined surface of the gain element 702 by a gap 711. The saturable absorber element 709 can have a first surface, which can optionally be perpendicular to a longitudinal axis of the laser 700 and a second, inclined surface. The first surface of the saturable absorber element 709 can include the output coupler 707. The reflectivity of the wanted, unwanted, and/or pump wavelengths of the surfaces 717, 718, 705, 703, 713, 707 can be of any of the lasers 600A, 600B, 600C, or variants thereof. For example, the surfaces 705, 703, 707 can be anti-reflective of the unwanted wavelengths. The surfaces 713 can be anti-reflective or highly reflective of the unwanted wavelength. The inclined surfaces 703, 717 can suppress feedback from internal surfaces along a cavity axis, and/or reflect the unwanted wavelengths to increase losses in the cavity 706. The surface 713 can also be highly reflective of the pump wavelength to protect the saturable absorber element 709 from bleaching by the pump radiation.

The inclined surface of the gain element 702 and the saturable absorber element 709 can be generally parallel (for example, at less than about 10 degree, or at less than about 5 degree). The first and second surfaces 717, 718 of the folding and/or deflecting element 701 can also be inclined. The exo-cavity folding and/or deflecting element 701, the gain element 702, and the saturable absorber element 709 can be generally collinear to form an in-line laser 700. The in-line laser 700 can improve the compactness, and/or portability of the laser system 70. The inclined surfaces of the gain element 702 and the saturable absorber element 709 need not be parallel to each other.

The coatings and/or spatial arrangement of the elements in the laser 700 can increase the output pulse energy and decreasing pulse duration for sub-optimal (desired) pulse wavelengths, and/or improve the lifetime of the laser 700 by having one or more of the features described above.

Figure 8B:
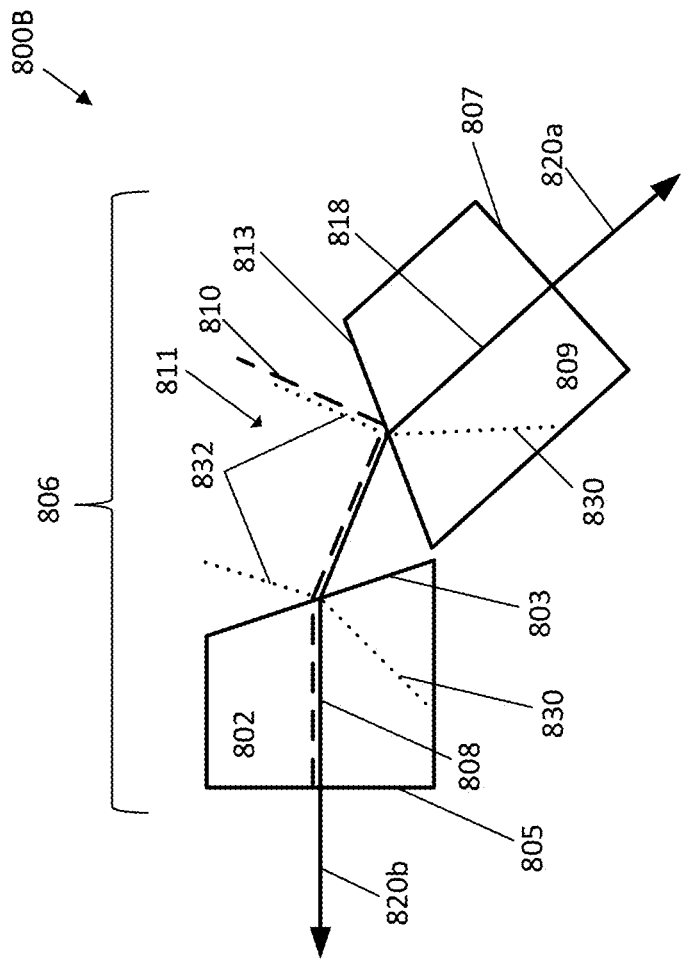
FIG. 8B illustrates schematically an example passively Q-switched micro-chip laser.

Turning to FIGS. 8A and 8B, an example passively Q-switched microchip laser 800A can have any of features of the lasers 500A, and an example passively Q-switched microchip laser 800B can have any of features of the lasers 500B, except as described below. The reference numbers of the same or similar features of 500A, 500B, 800A, 800B share the same last two digits.

In FIG. 8A, the pump beam as indicated by the dashed line 810 is introduced from the reflector 805 side and double-passing of the pump beam can be achieved by the reflector 813 being highly reflective or reflective of the pump wavelength. The reflectivity of the surfaces in FIG. 800A for the wanted, pump, and unwanted wavelengths can be the same as the corresponding surfaces in FIG. 500A.

In FIG. 8B, the pump beam as indicated by the dashed line 810 is introduced into the gap 811 to the highly reflective reflector 813 and double-passing of the pump beam can be achieved by the reflector 805 being highly reflective or reflective of the pump wavelength. The reflectivity of the surfaces in FIG. 800B for the wanted, pump, and unwanted wavelengths can be the same as the corresponding surfaces in FIG. 500B.

In the lasers 800A and 800B, the inclined surface (and thus the reflector 813) of the saturable absorber element 809 is not generally parallel to the inclined surface (and thus the reflector 803) of the gain element 802. The saturable absorber element 809 is flipped about its axis 818 compared to the saturable absorber element 509. While in the lasers 500A, 500B, light travels through a longer portion of the gain element 502 followed by a shorter portion of the saturable absorber element and vice versa, in the lasers 800A, 800B, light travels through a longer portion of the gain element 502 followed by a longer portion of the saturable absorber element 809, and light travels through a shorter portion of the gain element 802 followed by a shorter portion of the saturable absorber element 809. The lasers 800A, 800B can have more symmetry for the oscillating beam of light because light of less gain (through the shorter portion of the gain element 802) encounters less absorption (through the shorter portion of the saturable absorber element 809) and vice versa. The amount of increased symmetry can be greater for larger angles of inclination of the inclined surfaces of the gain element 802 and the saturable absorber element 809.

Figure 8C:
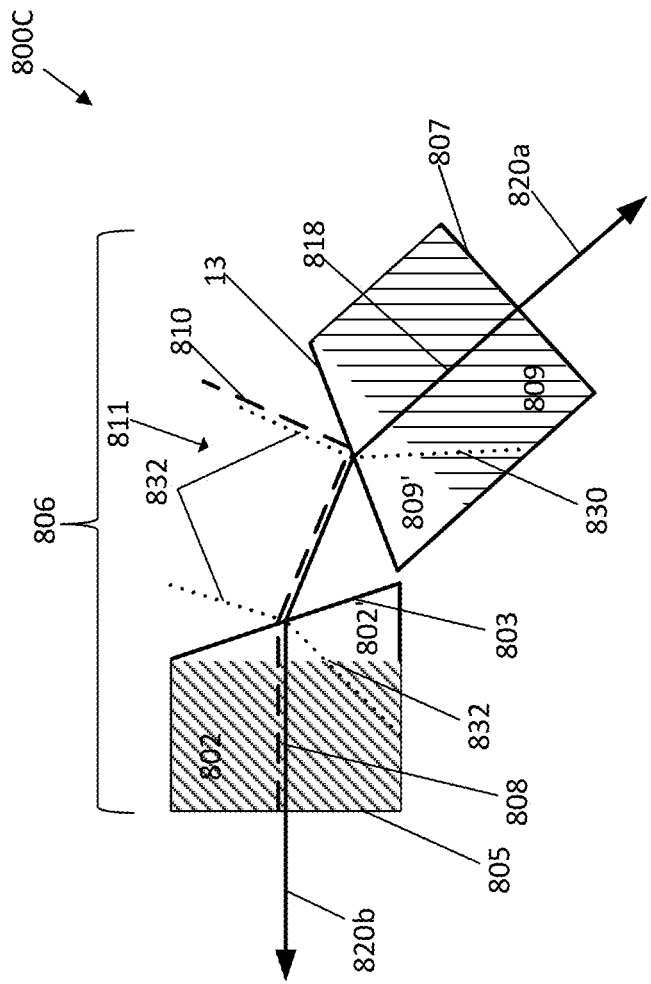
FIG. 8C illustrates schematically an example passively Q-switched micro-chip laser.

In FIG. 8C, an example passively Q-switched microchip laser 800C can have any of features of the laser 800B, except as described below. The same or similar features of the systems 800B, 800C share the same reference numbers.

In the system 800C, the gain element 802 and the saturable absorber element 809 can each include partially doped crystals. The doped portions are illustrated as the shaded areas in the gain element 802 and the saturable absorber element 809 and the undoped portions, which are the portions that cannot produce gain, are illustrated as the unshaded areas. As shown in FIG. 8C, the doped portions can be, but need not be, generally rectangular, and the undoped portions can occupy a remainder 802' of the gain element or a remainder 809' of the saturable absorber element. The remainder 802', 809' can include the inclined surface. The partially doped gain element and/or saturable absorber element can improve the uniformity of the laser beam output indicated by the arrow 820a or 802b, while still allowing the inclined surfaces to suppress feedback from internal surfaces along the first and second axes 808, 818, and/or reflect the unwanted wavelengths to increase losses in the cavity 806. The partial doping features can be incorporated into any of the gain elements and/or saturable absorber elements having an inclined surface as described herein to improve uniformity in the laser beam output.

Figure 9:
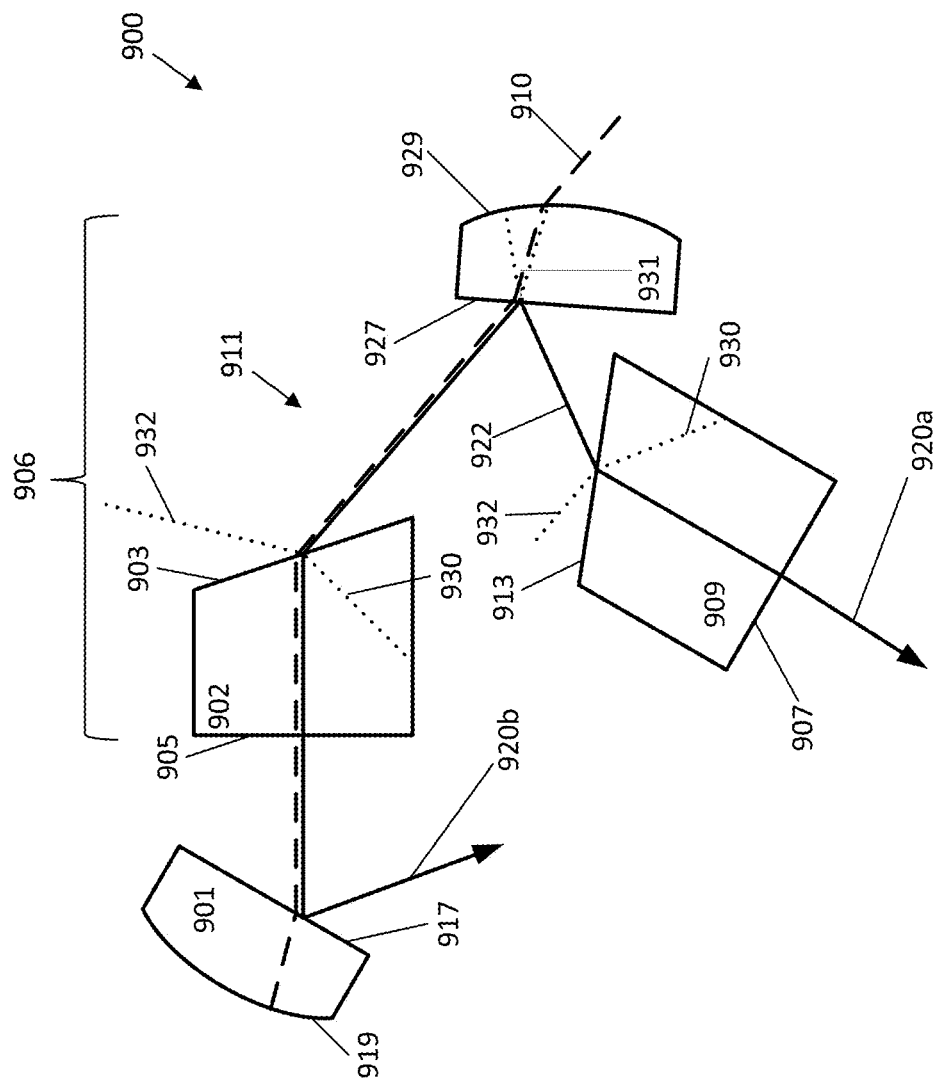
FIG. 9 illustrates schematically an example passively Q-switched micro-chip laser.

Turning to FIG. 9, an example passively Q-switched microchip laser 900 can incorporate a combination of one or more features of the lasers described above. The reference numbers of the same or similar features of the laser described above and the laser 900 share the same last two digits.

The laser 900 can include an exo-cavity folding and/or deflecting element 901 have the same or similar features as the exo-cavity folding and/or deflecting element 601 in FIG. 6C. The laser 900 can also include a gain element 902 and a saturable absorber element 909, with the saturable absorber element 909 rotated relative to the position of the saturable absorber element 609 in FIG. 6C. In some embodiments, the gain element 902 and the saturable absorber element 909 can also be arranged similar to the gain element 802 and the saturable absorber element 809 in FIG. 8B, that is, light travels through a shorter portion of the gain element 902 followed by a shorter portion of the saturable absorber element 909 and vice versa.

The laser 900 can further include an intra-cavity folding and/or deflecting element 931 located between the inclined surface (and reflector 903) of the gain element 902 and the inclined surface (and reflector 913) of the saturable absorber element 909. The intra-cavity folding and/or deflecting element 931 can have a first coated surface 927 and an opposing second coated surface 929. The first surface 927 can be generally flat. The second surface 929 can be curved or dome-shaped. The first surface 927 can be facing the gap 911 between the gain element 902 and the saturable absorber element 909. The second surface 929 can be facing away from the gap 911.

The intra-cavity folding and/or deflecting element 931 can be positioned so that the flat first surface 927 can deflect or reflect light of the wanted wavelengths between the mirror 903 and the mirror 913. The first surface 927 and the second surface 929 can be anti-reflective of the pump wavelength to allow a pump beam entering the laser cavity 906 from the second surface 929 side of the intra-cavity folding and/or deflecting element 931 to be directed to the gain element 902. The intra-cavity folding and/or deflecting element 931 can act as a lens for focusing the pump beam to the inclined surface of the gain element 902. The reflectors 905 and 903 of the gain element 902 and the first surface 917 of the exo-cavity folding and/or deflecting element 901 can be anti-reflective of the pump wavelength. The second surface 919 of the exo-cavity folding and/or deflecting element 901 can be highly reflective of the pump wavelength to allow double-passing of the pump wavelength in the gain element 902. The second surface 919 of the exo-cavity folding and/or deflecting element 901 being highly reflective of the pump wavelength can allow the reflector 905 to be two-wavelength coated rather than triple-wavelength coated as described above, as any leaked pump beam can be reflected and re-imaged back by the second surface 918.

The intra-cavity folding and/or deflecting element 931 can be optionally positioned to also allow Brewster angle (a special angle of incidence that produces a 90 degree angle between the reflected and refracted light ray) to be employed to avoid anti-reflective coating on certain surfaces, such as the inclined surface of the saturable absorber element 909

The first surface 917 of the exo-cavity folding and/or deflecting element 901 can also act as a steering mirror for a laser beam of the wanted wavelengths as indicated by the arrow 620b, which can be produced when the reflector 905 is functioning as the output coupler and the mirror 907 is functioning as the total reflector of the wanted wavelengths.

The reflectivity of the surfaces in FIG. 900 for the wanted, pump, and unwanted wavelengths is summarized in Table 8 below.

TABLE 8

| Surface (Ref. No.) | Reflectivity for Wavelengths | | |
|---|---|---|---|
| | Wanted (Lasing) | Pump | Unwanted (Parasitic) |
| 905 | 920a: HR 920b: % R | LR or UR | AR |
| 903 | AR | AR | LR or UR |
| 913 | AR | HR | PR or UR |
| 907 | 920a: % R 920b: HR | UR | AR |
| 927 | HR | AR | AR |
| 929 | UR | AR | AR |

TABLE 8-continued

| Surface (Ref. No.) | Reflectivity for Wavelengths | | |
|---|---|---|---|
| | Wanted (Lasing) | Pump | Unwanted (Parasitic) |
| 917 | HR | AR | HR or PR |
| 919 | UR | HR | AR |

Examples of Laser Generator for Malaria Detection

Figure 10A:
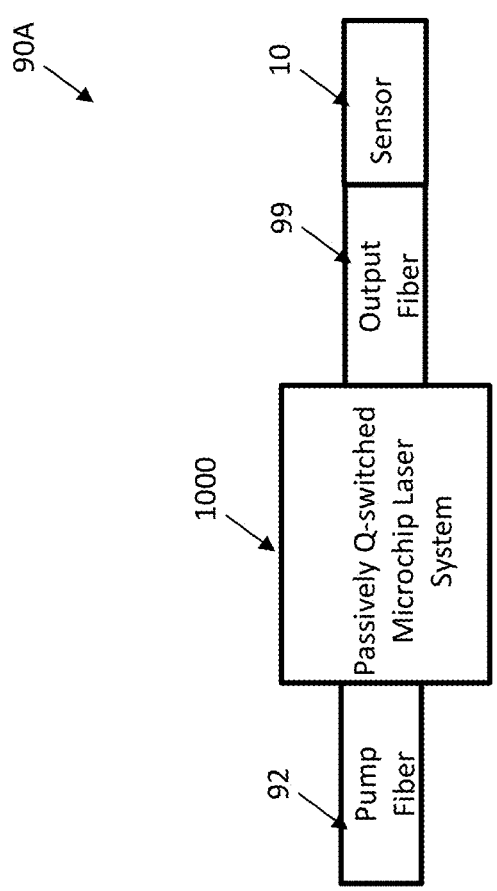
FIG. 10A illustrates schematically an example laser operably coupled to a malaria sensor.
Figure 10B:
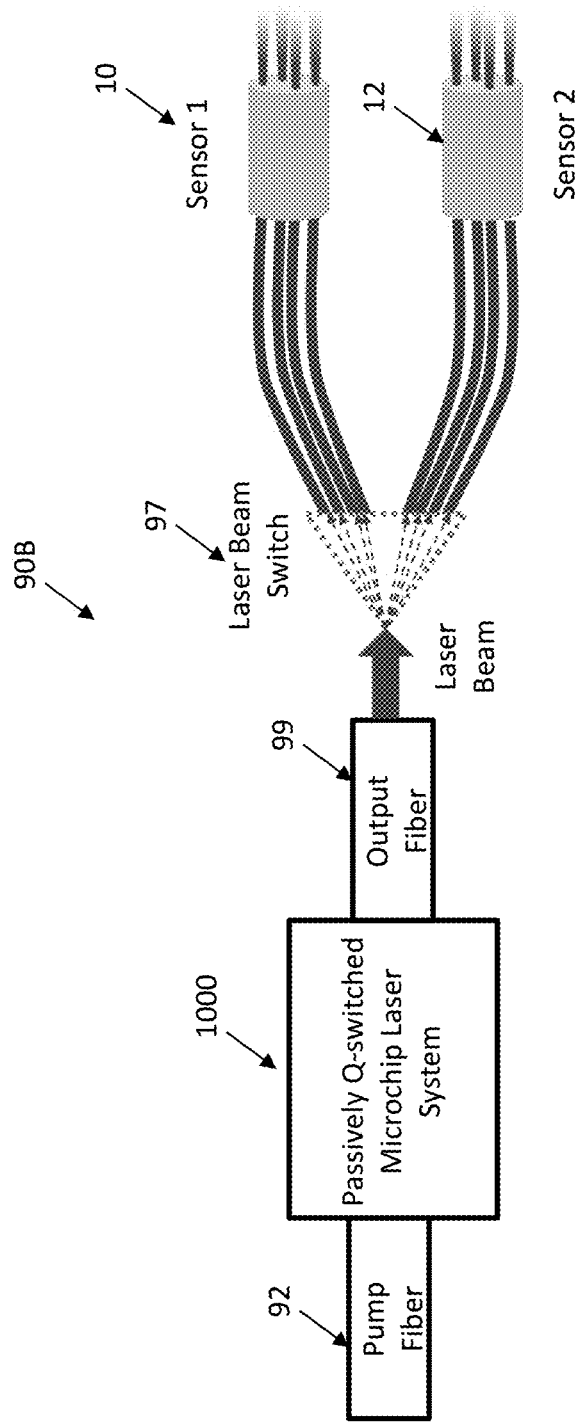
FIG. 10B illustrates schematically an example laser operably coupled to more than one malaria sensor.

FIGS. 10A and 10B illustrate a laser-based malaria detection system 90A, 90B having a passively Q-switched microchip laser 1000 which can be any of the lasers described above or a laser having combinations of one or more features of the lasers described above and/or obvious variations thereof based on the disclosure herein. As shown in FIGS. 10A and 10B, the system 90A, 90B can have a pump fiber 92 coupled to the laser 1000 on one side of the laser 1000 and an output fiber coupled 88 coupled to the laser 1000 on an opposite side of the laser 1000. The system 90A, 90B can also have pump shaping optics coupling the pump fiber 92 to the laser 1000. The system 90A, 90B can also have second harmonic generation and filtering elements coupled via beam delivery optics into the output fiber 99.

In FIG. 10A, the laser beam from the output fiber 99 can be directed to a malaria detection sensor 10, as such described in U.S. application Ser. No. 16/213,923. In FIG. 10B, the laser beam from the output fiber 99 can be directed to a first malaria detection sensor 10 and/or a second malaria detection sensor 12. The first and second malaria detection sensors 10, 12 can be applied to different measurement locations on a test subject, including but not limited to the hand, the ankle, the base of the tongue, or others. For example, the first malaria detection sensor 10 can be applied to a test subject's ankle, and the second malaria detection sensor 12 can be applied to the test subject's arm. The output fiber 99 can also be coupled to more than two malaria detection sensors.

Figure 10C:
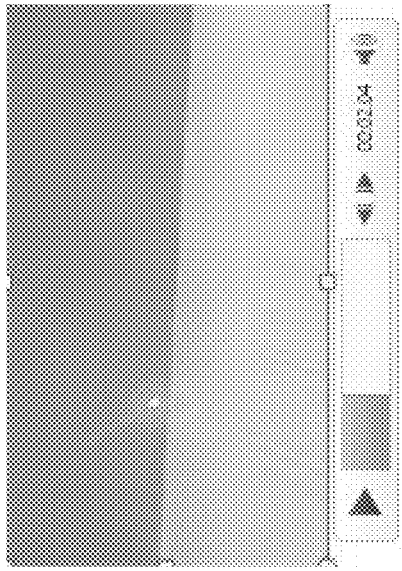
FIG. 10C-10E illustrates example sequential emissions of laser pulses using example lasers disclosed herein.
Figure 10E:
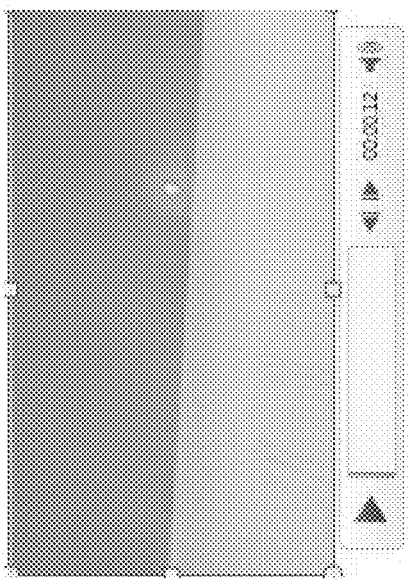
Figure 10D:
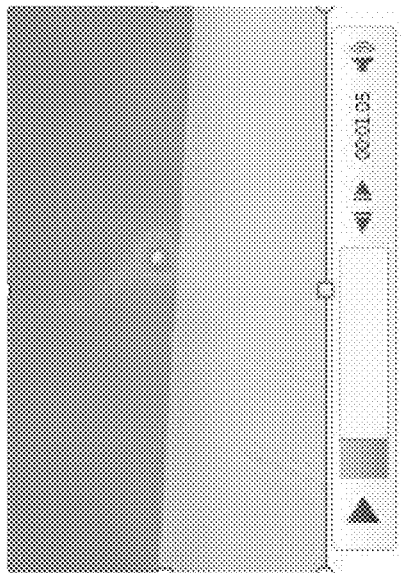

As shown in FIG. 10B, the first and/or second malaria detection sensors 10, 12 can each have a plurality of optical fibers, such as four optical fibers. Detailed descriptions of a malaria detection sensor having a plurality of optical fibers and acoustic detectors are disclosed in U.S. application Ser. No. 16/213,923. The pulsed laser beam generated by the system 90B can be sent to different sensors coupled to the output fiber 99 via laser switching 97. Laser switching can be accomplished by a multiplex unit configured to send pulses to one of the plurality of malaria detection sensors coupled to the output fiber 99. FIG. 10C illustrates example successive laser pulses produced by an example passively Q-switched microchip laser disclosed herein. The laser system 90B can allow four zones within each of the two measurement locations to which the first and second sensors 10, 12 are applied to be probed by sequentially switching the laser beam generated by the passively Q-switched microchip laser 1000.

Figure 11A:
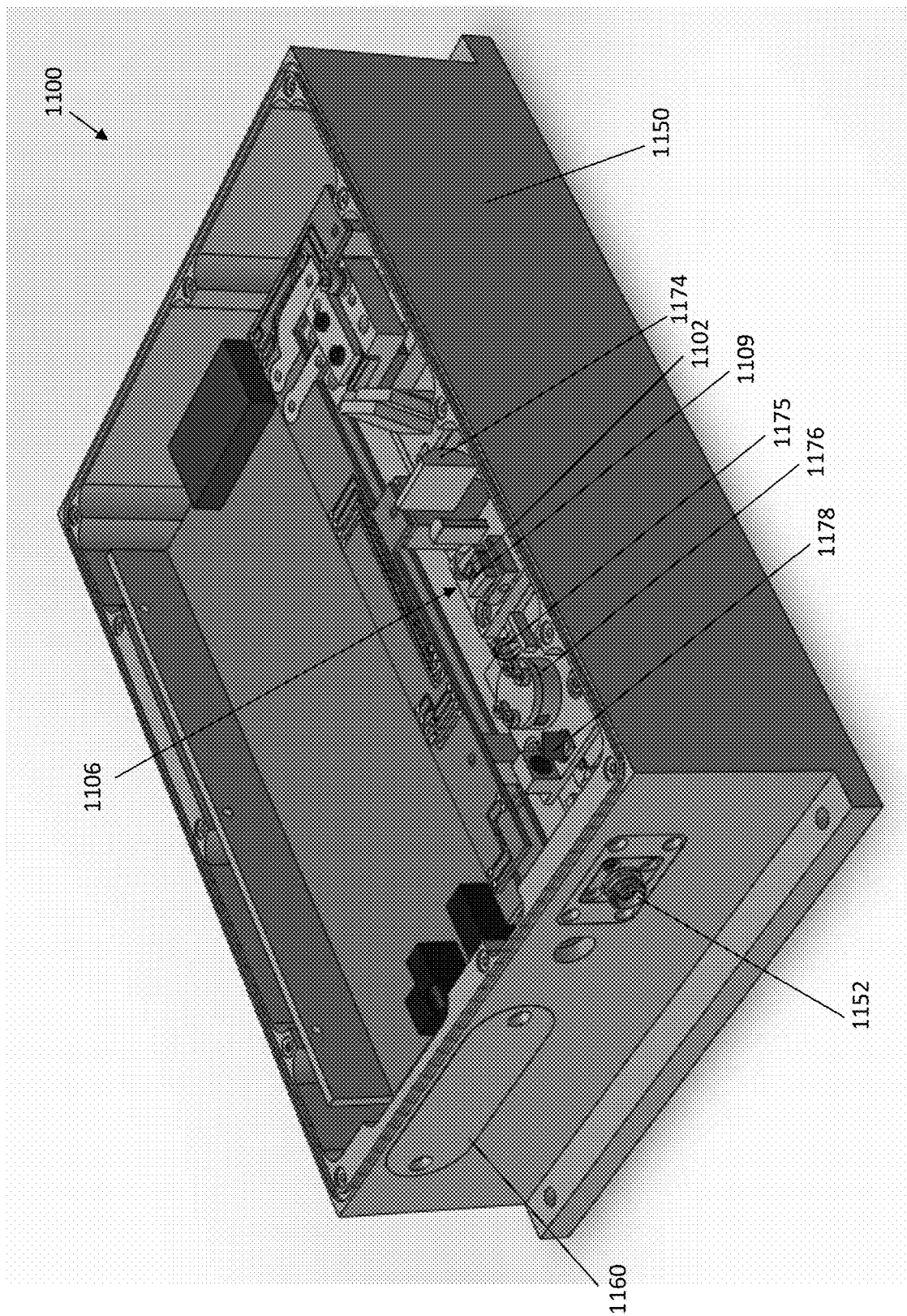
FIGS. 11A-11B illustrate perspective views of an example laser generator with a passively Q-switched microchip laser.
Figure 11B:
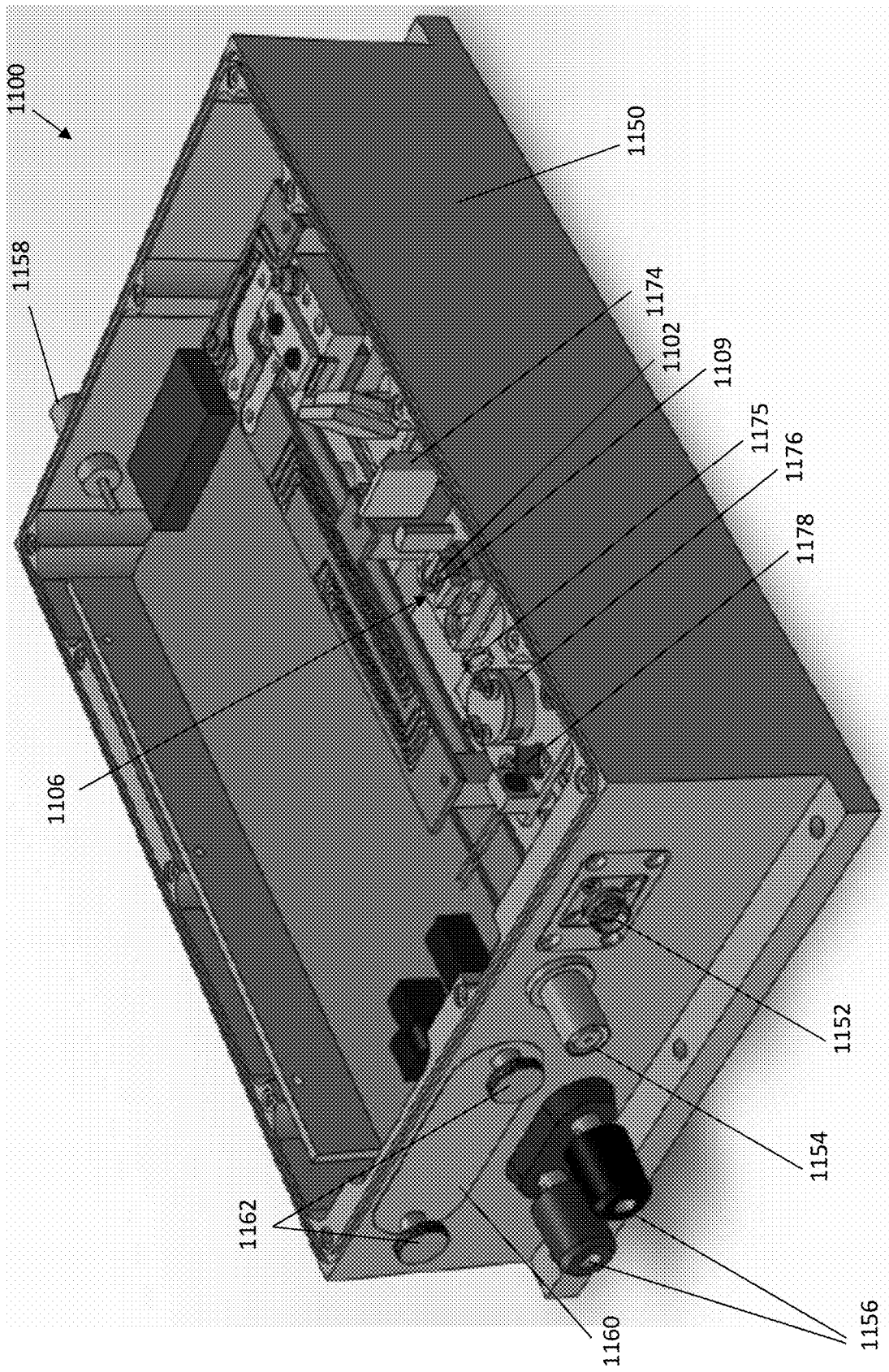
Figure 11C:
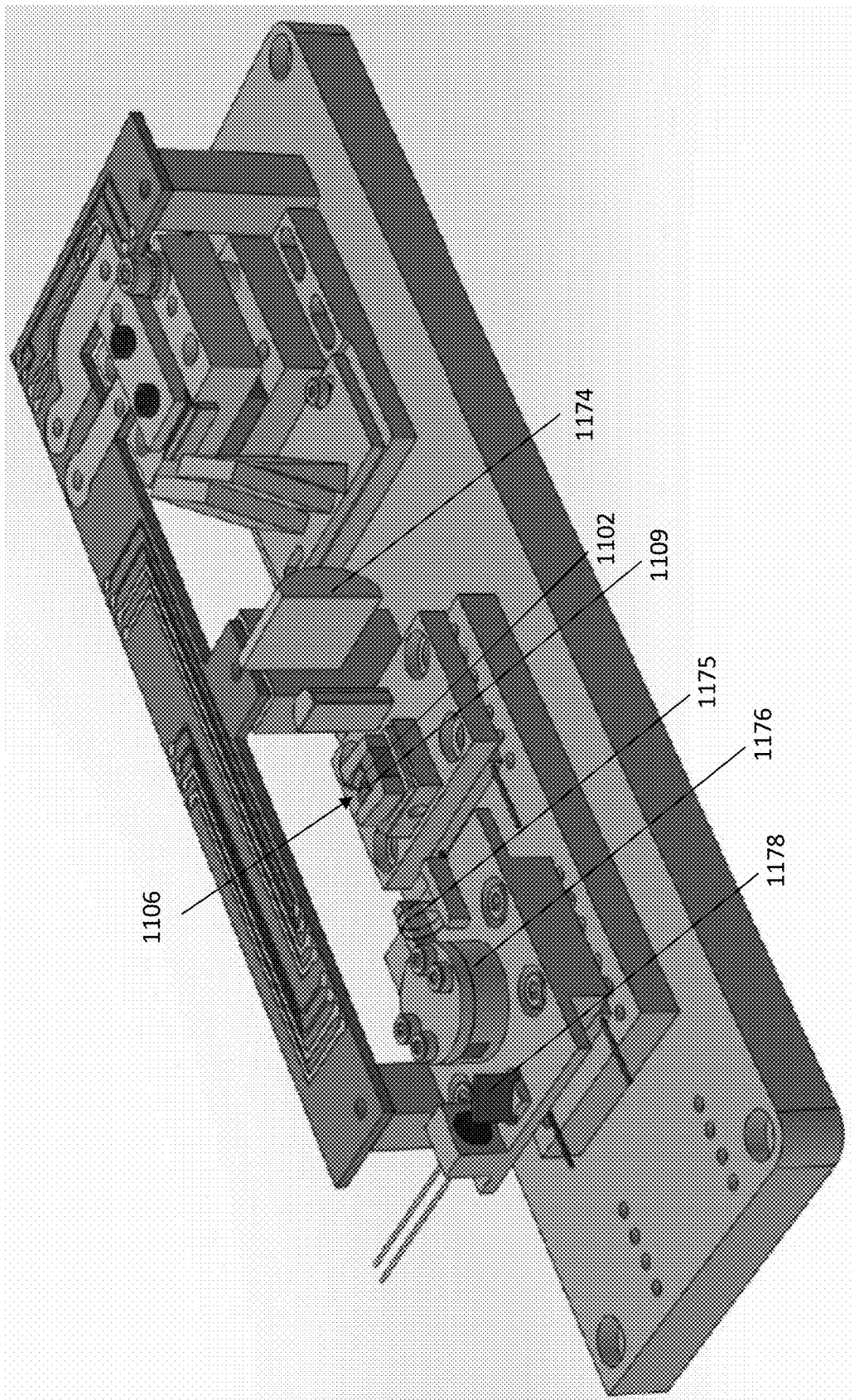
FIG. 11C illustrates a perspective view of certain internal components of the laser generator of FIGS. 11A and 11B.

FIGS. 11A-11C illustrate an example laser generator 1100, which can include the passively Q-switched microchip laser system 1000 of FIGS. 10A and 10B, and can provide laser pulses to the malaria detection sensor 10.

The laser generator 1100 can have a housing 1150. In FIGS. 11A and 11B, the top cover of the housing 1150 is not shown so as to illustrate internal components of the generator 1100. The size and/or shape of the housing 1150 can vary, although the housing 1150 can be configured to allow the laser generator 1100 to be suitable for being placed on a table top, and/or for portability, for example, by being able to fit into luggage cases and/or airline overhead bins. The housing 1150 can be watertight or at least substantially impermeable to water, moisture, and/or the like. Connection ports on the housing 1150 can be sealed to be watertight or at least substantially impermeable to water, moisture, and/or the like.

The housing 1150 can enclose any of the passively Q-switched microchip lasers disclosed herein or obvious variations thereof based on the disclosure herein. As shown in FIGS. 11A-11C, the laser generator 1100 can include pump shaping optics 1174, a laser cavity 1106 including a gain element 1102 and a saturable absorber element 1109, and second harmonic generation and filtering elements 1176. The pump shaping optics 1174 can couple a pump fiber (see e.g. FIG. 12, 1272) to the laser cavity 1106 on the side of the gain element 1102. The second harmonic generation and filtering elements 1176 can be coupled to the laser cavity 1106 on the side of the saturable absorber element 1109. A lens 1175 can be positioned between the laser cavity 1106 and the second harmonic generation and filtering elements 1176. The second harmonic generation and filtering elements 1176 can be coupled via beam delivery optics 1178 into an output fiber, such as the example output fibers disclosed herein.

As shown in FIGS. 11A and 11B, the housing 1150 can include a port 1152 for coupling to the output fiber. The housing 1150 can include other ports, for example, as shown in FIG. 11B but not limited to, a photodiode output port 1154 (for example, a BNC connector or the like) for detection triggering to catch the fraction of the light during the laser pulse, a power input 1156 (which can, for example, accept either power plus or bare wires), and an ON/OFF switch 1158 of the laser generator 1100.

Laser parameters of the laser generator 1100 can be adjusted. In some embodiments, the parameters can be adjusted using a controller (for example, a computer) via USB ports (or other types of data ports) on the housing 1150 of the generator 1100. The USB ports can be hidden by a control panel seal 1160 shown in FIGS. 11A and 11B. The laser generator can optionally include its own control panel for adjusting the laser parameters. The control panel seal 1160 can provide sealing against water, moisture, and/or the like. For example, the control panel seal 1160 can include a rubber or otherwise deformable and conformable material to provide sealing of the USB ports or a control panel. In some embodiments, the control panel seal 1160 can be secured onto the housing 1150 by a plurality (for example, two or more) screws 1162.

Figure 12A:
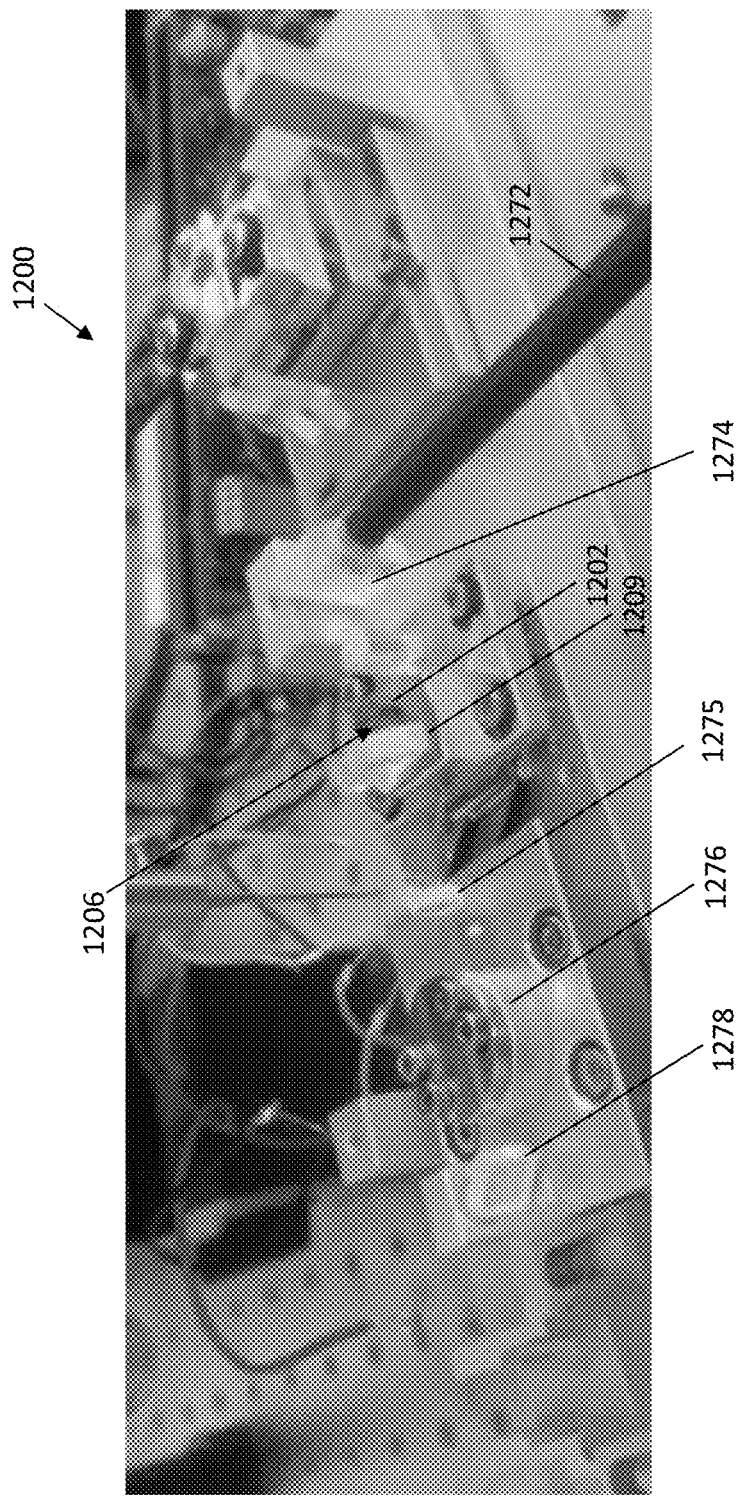
FIG. 12A illustrates a perspective view of a passively Q-switched microchip laser.
Figure 12B:
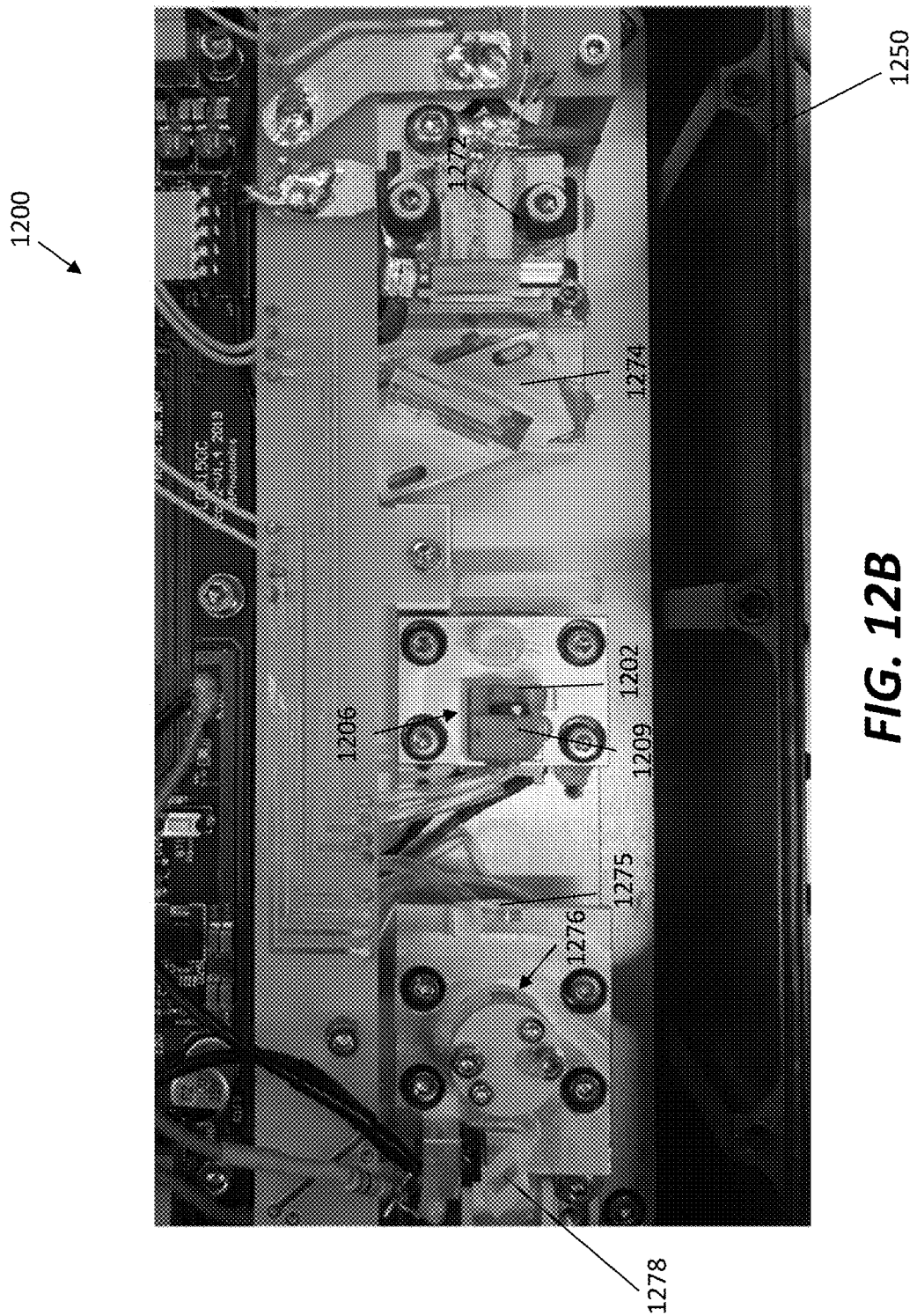
FIG. 12B illustrates a top view of the passively Q-switched microchip laser of FIG. 12A.

FIGS. 12A-12B illustrate an example passively Q-switched microchip laser 1200, which can be part of the laser generator 1100 of FIGS. 11A-11B and be enclosed in a housing 1250. The passively Q-switched microchip laser 1200 can have any configurations disclosed herein or obvious variations thereof based on the disclosure herein. Features of the passively Q-switched microchip laser 1200 can be incorporated into features of the passively Q-switched microchip laser in FIGS. 11A-11C and features of the passively Q-switched microchip laser in FIGS. 11A-11C can be incorporated into features of the passively Q-switched microchip laser 1200.

The laser 1200 can include pump shaping optics 1274, a laser cavity 1206 including a gain element and a saturable absorber element, and second harmonic generation and filtering elements 1276. The pump shaping optics 1274 can couple a pump fiber 1272 to the laser cavity 1206 on the side of the gain element 1202. The second harmonic generation and filtering elements 1276 can be coupled to the laser cavity 1206 on the side of the saturable absorber element 1209. A lens 1275 can be positioned between the laser cavity 1206 and the second harmonic generation and filtering elements 1276. The second harmonic generation and filtering elements 1276 can be coupled via beam delivery optics 1278 into an output fiber.

Terminology

Terms of orientation used herein, such as "proximal," "distal," "radial," "central," "longitudinal," and "end" are used in the context of the illustrated embodiment. However, the present disclosure should not be limited to the illustrated orientation. Indeed, other orientations are possible and are within the scope of this disclosure. Terms relating to circular shapes as used herein, such as diameter or radius, should be understood not to require perfect circular structures, but rather should be applied to any suitable structure with a cross-sectional region that can be measured from side-to-side. Terms relating to shapes generally, such as "circular" or "spherical" or "semi-circular" or "hemisphere" or any related or similar terms, are not required to conform strictly to the mathematical definitions of circles or spheres or other structures, but can encompass structures that are reasonably close approximations.

Conditional language, such as "can," "could," "might," or "may," unless specifically stated otherwise, or otherwise understood within the context as used, is generally intended to convey that certain embodiments include, while other embodiments do not include, certain features, elements, and/or steps. Thus, such conditional language is not generally intended to imply that features, elements, and/or steps are in any way required for one or more embodiments or that one or more embodiments necessarily include logic for deciding, with or without user input or prompting, whether these features, elements, and/or steps are included or are to be performed in any particular embodiment.

The terms "approximately," "about," and "substantially" as used herein represent an amount close to the stated amount that still performs a desired function or achieves a desired result. For example, in some embodiments, as the context may permit, the terms "approximately", "about", and "substantially" may refer to an amount that is within less than or equal to 10% of the stated amount. The term "generally" as used herein represents a value, amount, or characteristic that predominantly includes or tends toward a particular value, amount, or characteristic. As an example, in certain embodiments, as the context may permit, the term "generally parallel" can refer to something that departs from exactly parallel by less than or equal to 15 degrees.

While a number of variations of the disclosure have been shown and described in detail, other modifications, which are within the scope of this disclosure, will be readily apparent to those of skill in the art based upon this disclosure. It is also contemplated that various combinations or sub-combinations of the specific features and aspects of the embodiments may be made and still fall within the scope of the disclosure. Accordingly, it should be understood that various features and aspects of the disclosed embodiments can be combined with or substituted for one another in order to form varying modes of the disclosed.

Furthermore, certain features that are described in this disclosure in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations, one or more features from a claimed combination can, in some cases, be excised from the combination, and the combination may be claimed as a subcombination or variation of a subcombination.

Features, materials, characteristics, or groups described in conjunction with a particular aspect, embodiment, or example are to be understood to be applicable to any other aspect, embodiment or example described in this section or elsewhere in this specification unless incompatible therewith. All of the features disclosed in this specification (including any accompanying claims, abstract and drawings) may be combined in any combination, except combinations where at least some of such features and/or steps are mutually exclusive. The protection is not restricted to the details of any foregoing embodiments. The protection extends to any novel one, or any novel combination, of the features disclosed in this specification (including any accompanying claims, abstract and drawings), or to any novel one, or any novel combination so disclosed.

For purposes of this disclosure, certain aspects, advantages, and novel features are described herein. Not necessarily all such advantages may be achieved in accordance with any particular embodiment. Thus, for example, those skilled in the art will recognize that the disclosure may be embodied or carried out in a manner that achieves one advantage or a group of advantages as taught herein without necessarily achieving other advantages as may be taught or suggested herein.

Some embodiments have been described in connection with the accompanying drawings. The figures are not drawn to scale where appropriate, but such scale should not be limiting, since dimensions and proportions other than what are shown are contemplated and are within the scope of the disclosed invention. Distances, angles, etc. are merely illustrative and do not necessarily bear an exact relationship to actual dimensions and layout of the devices illustrated. Components can be added, removed, and/or rearranged. Further, the disclosure herein of any particular feature, aspect, method, property, characteristic, quality, attribute, element, or the like in connection with various embodiments can be used in all other embodiments set forth herein. Additionally, any methods described herein may be practiced using any device suitable for performing the recited steps.

Although this invention has been disclosed in the context of certain embodiments and examples, the scope of this disclosure extends beyond the specifically disclosed embodiments to other alternative embodiments and/or uses of the invention and obvious modifications and equivalents thereof. Any system, method, and device described in this application can include any combination of the preceding features described in this and other paragraphs, among other features and combinations described herein, including features and combinations described in subsequent paragraphs. While several variations of the invention have been shown and described in detail, other modifications, which are within the scope of this invention, will be readily apparent to those of skill in the art based upon this disclosure. It is also contemplated that various combinations or sub-combinations of the specific features and aspects of the embodiments may be made and still fall within the scope of the invention. Various features and aspects of the disclosed embodiments can be combined with, or substituted for, one another in order to form varying modes of the disclosed invention. Thus, it is intended that the scope of the present invention herein disclosed should not be limited by the particular disclosed embodiments described above, but should be determined only by a fair reading of the claims that follow.

What is claimed is:

1. A passively Q-switched microchip laser configured for generating transient vapor nanobubbles around malaria-specific nanoparticles in a human, the laser comprising:
   a laser cavity bound by a reflector and an optical coupler;
   a gain element located in the laser cavity, the gain element having a first axis, a first gain element surface, and a second gain element surface, the first gain element surface being adjacent to one of the reflector or the optical coupler;
   a saturable absorber element in the laser cavity, the saturable absorber element having a second axis, a first saturable absorber element surface, and a second saturable absorber element surface, the first saturable absorber element surface being adjacent to another one of the reflector or the optical coupler,
   wherein, in response to pumping energy at a predetermined pumping wavelength, the gain element is configured to produce simulated emission of at least a first wavelength and a second wavelength, wherein a simulated emission cross-section of the second wavelength is greater than a simulated emission cross-section of the first wavelength, wherein the second wavelength is a fundamental wavelength,
   wherein the passively Q-switched microchip laser further comprises one or more fundamental wavelength suppression features such that the saturable absorber element is configured to output a pulsed laser beam substantially of the first wavelength.

2. The laser of claim 1, wherein the pulsed laser beam has a duration less than about 300 picoseconds.

3. The laser of claim 1, wherein the pulsed laser beam has an energy of at least about 20 microjoule.

4. The laser of claim 1, wherein the pumping wavelength is between 670 nm to 675 nm.

5. The laser of claim 1, wherein the one or more fundamental wavelength suppression features comprise the second gain element surface being at an angle to the first axis.

6. The laser of claim 5, wherein the one or more fundamental wavelength suppression features further comprise the second saturable absorber element surface being at an angle to the second axis.

7. The laser of claim 1, wherein the first and second axes are substantially collinear.

8. The laser of claim 1, wherein the first and second axes are offset from each other.

9. The laser of claim 1, wherein the second gain element surface and the second saturable absorber element surface are generally parallel.

10. The laser of claim 1, wherein the first axis is at an angle with the second axis.

11. The laser of claim 1, wherein the second gain element surface and the second saturable absorber element surface are at an angle with each other.

12. The laser of claim 1, wherein the one or more fundamental wavelength suppression features comprise an exo-cavity element.

13. The laser of claim 12, wherein the exo-cavity element is located on an opposite side of the gain element from a pump, the exo-cavity element configured to reflect back pump radiation into the cavity.

14. The laser of claim 12, wherein the exo-cavity element is located next to the first gain element surface and substantially collinear with an optical axis of the laser cavity, the exo-cavity element configured to isolate feedback of a first wavelength from pump shaping optics.

15. The laser of claim 12, further comprising an intra-cavity element between the gain element and the saturable absorber element, the intra-cavity element configured to focus pump radiation into the gain element.

16. The laser of claim 1, wherein the first gain element surface is perpendicular to the first axis.

17. The laser of claim 1, wherein the first saturable absorber element surface is perpendicular to the second axis.

18. A laser generator device outputting laser pulse(s) configured to generate transient vapor nanobubbles around malaria-specific nanoparticles in a human or ex vivo, the device comprising:

the passively Q-switched microchip laser of claim 1;

a laser pump coupled to the passively Q-switched microchip laser via a pump fiber; and an output fiber coupling the passively Q-switched microchip laser and one or more malaria detection sensors.

19. The laser generator device of claim 18, further comprising second harmonic generation and filtering elements coupling the passively Q-switched microchip laser to the output fiber.

20. The laser generator device of claim 18, wherein the device is configured to sequentially switch the outputted pulsed laser beam among a plurality of optical fibers in the one or more malaria detection sensors.

* * * * *